United States Patent
Jeon et al.

(10) Patent No.: US 10,461,265 B2
(45) Date of Patent: Oct. 29, 2019

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Aram Jeon, Suwon-si (KR); Ohyun Kwon, Suwon-si (KR); Yoonhyun Kwak, Seoul (KR); Kum Hee Lee, Suwon-si (KR); Kyuyoung Hwang, Anyang-si (KR); Sangdong Kim, Seoul (KR); Byoungki Choi, Hwaseong-si (KR); Hyeonho Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 409 days.

(21) Appl. No.: 15/091,603

(22) Filed: Apr. 6, 2016

(65) Prior Publication Data
US 2017/0033300 A1 Feb. 2, 2017

(30) Foreign Application Priority Data
Jul. 27, 2015 (KR) .......... 10-2015-0106105

(51) Int. Cl.
*H01L 51/00* (2006.01)
*C09K 11/06* (2006.01)
(Continued)

(52) U.S. Cl.
CPC ........ *H01L 51/0085* (2013.01); *C07F 15/004* (2013.01); *C09K 11/06* (2013.01);
(Continued)

(58) Field of Classification Search
CPC ...... H01L 51/0084–0092; C09K 11/06; C09K 2211/1029; C09K 2211/1044;
(Continued)

(56) References Cited

U.S. PATENT DOCUMENTS

2002/0134984 A1* 9/2002 Igarashi ................ C09K 11/06
257/79
2007/0034863 A1* 2/2007 Fortte ................. C07F 15/0033
257/40
(Continued)

FOREIGN PATENT DOCUMENTS

CN 103130841 A * 6/2013
JP 2002100420 A * 4/2002
(Continued)

*Primary Examiner* — William E McClain
(74) *Attorney, Agent, or Firm* — Cantor Colburn LLP

(57) ABSTRACT

An organometallic compound represented by Formula 1:

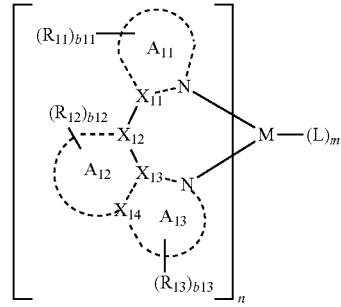

Formula 1 wherein, in Formula 1, groups and variables are the same as described in the specification.

19 Claims, 1 Drawing Sheet

(51) Int. Cl.
 *C07F 15/00* (2006.01)
 *H01L 51/50* (2006.01)
(52) U.S. Cl.
 CPC ............... *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/5016* (2013.01)
(58) Field of Classification Search
 CPC .... C09K 2211/1088; C09K 2211/1092; C09K 2211/185; C07F 15/004
 See application file for complete search history.

(56) References Cited

U.S. PATENT DOCUMENTS

| | | | | |
|---|---|---|---|---|
| 2011/0284799 | A1* | 11/2011 | Stoessel | C07F 1/00 252/301.16 |
| 2013/0009118 | A1* | 1/2013 | Stoessel | H01L 51/0085 252/519.21 |
| 2015/0280147 | A1* | 10/2015 | Wesemann | C09K 11/06 252/301.16 |

FOREIGN PATENT DOCUMENTS

| | | |
|---|---|---|
| WO | 2010-086089 A1 | 8/2010 |
| WO | 2012-169548 A1 | 12/2012 |

* cited by examiner

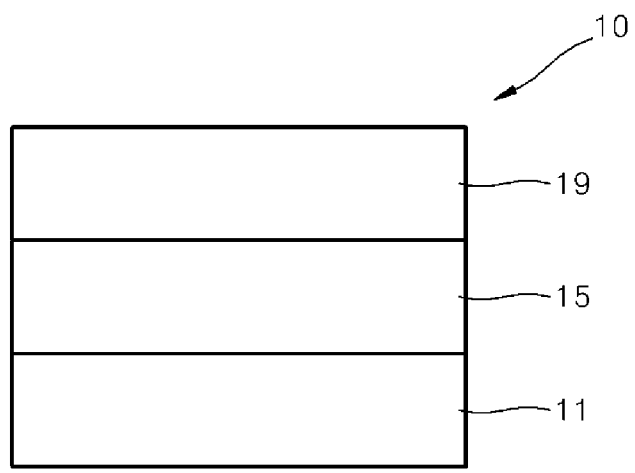

ORGANOMETALLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0106105, filed on Jul. 27, 2015, in the Korean Intellectual Property Office, the content of which is incorporated herein in its entirety by reference.

BACKGROUND

1. Field

The present disclosure relates to an organometallic compound and an organic light-emitting device including the organometallic compound.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state to thereby generate light.

Different types of organic light emitting devices are known. However, there still remains a need in OLEDs having low driving voltage, high efficiency, high brightness, and long lifespan.

SUMMARY

Provided are an organometallic compound and an organiclight-emitting device including the organometallic compound.

Additional aspects will be set forth in part in the description which follows and, in part, will be apparent from the description, or may be learned by practice of the presented exemplary embodiments.

According to an aspect of an exemplary embodiment, there is provided an organometallic compound represented by Formula 1:

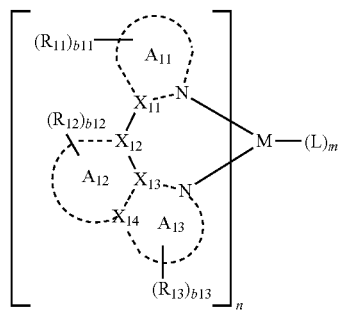

Formula 1 wherein, in Formula 1,

M is selected from a first-row transition metal of the Periodic Table of Elements, a second-row transition metal of the Periodic Table of Elements, and a third-row transition metal of the Periodic Table of Elements;

$X_{11}$ and $X_{14}$ are each independently selected from C and N;

$X_{12}$ and $X_{13}$ are C;

$A_{11}$ and $A_{13}$ are each independently selected from $C_1$-$C_{20}$ heterocyclic groups;

$A_{12}$ is selected from a $C_5$-$C_{20}$ cyclic group and a $C_1$-$C_{20}$ heterocyclic group;

$R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_3$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), and —N($Q_1$)($Q_2$), wherein $R_{11}$ and $R_{12}$ are optionally linked to each other to form a saturated or unsaturated ring; and $Q_1$ to $Q_3$ are each independently selected from a hydrogen, a deuterium, a substituted or unsubstituted $C_1$-$C_{20}$ alkyl group, a substituted or unsubstituted $C_6$-$C_{20}$ aryl group, a substituted or unsubstituted monovalent non-aromatic condensed polycyclic group, and a substituted or unsubstituted monovalent non-aromatic condensed heteropolycyclic group;

n is selected from 1 2, and 3;

L is selected from a monodentate ligand and a bidentate ligand; and m is selected from 0, 1, 2, 3, and 4.

According to an aspect of another exemplary embodiment, an organic light-emitting device includes:

a first electrode;

a second electrode; and an organic layer disposed between the first electrode and the second electrode, wherein the organic layer includes an emission layer and at least one organometallic compound represented by Formula 1.

BRIEF DESCRIPTION OF THE DRAWING

These and/or other aspects will become apparent and more readily appreciated from the following description of the exemplary embodiments, taken in conjunction with the accompanying drawings in which:

FIG. 1 is a schematic view illustrating a structure of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Rather, these embodiments are provided so that this disclosure will be thorough and complete, and will fully convey the effects and features of the present disclosure and ways to implement the present disclosure will fully convey the concept of the invention to those skilled in the art, Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. In the drawings, like reference numerals denote like elements throughout, and thus redundant description thereof will be omitted.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or," As used herein, the terms such as "comprising", "including", "having", or the like are intended to indicate the existence of the features regions, integers, steps, operations, components, and/or elements disclosed in the specification, and are not intended to preclude the possibility that one or more other features or elements may exist or may be added.

It will also be understood that when an element such as a layer, a region or a component is referred to as being "on" another layer or element, it can be directly on the other layer or element, or intervening layers, regions, or components may also be present. In contrast, when an element is referred to as being "directly on" another element, there are no intervening elements present, In the drawings, the sizes of elements are exaggerated or reduced for ease of description. The size or thickness of each element shown in the drawings are arbitrarily illustrated for better understanding or ease of description, and thus the present disclosure is not limited thereto.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value, As used herein, the term "organic layer" refers to a single layer and/or a plurality of layers disposed between first and second electrodes of an organic light-emitting device, A material in the "organic layer" is not limited to an organic material.

According to an aspect of the present disclosure, there is provided an organometallic compound represented by Formula 1:

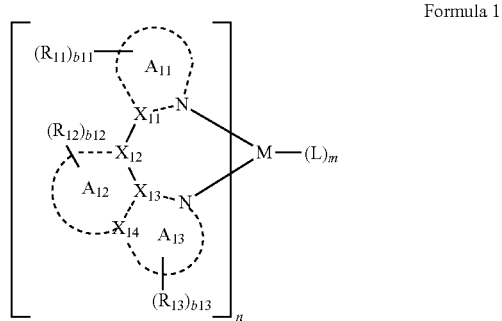

Formula 1

In Formula 1, M may be selected from a first-row transition metal of the Periodic Table of Elements, a second-row transition metal of the Periodic Table of Elements, and a third-row transition metal of the Periodic Table of Elements.

For example, in Formula 1, M may be selected from iridium (Ir), platinum (Pt), osmium (Os), ruthenium (Ru), rhodium (Rh), palladium (Pd), copper (Cu), silver (Ag), gold (Au), titanium (Ti), zirconium (Zr), hafnium (Hf), europium (Eu), terbium (Tb), and thulium (Tm), but is not limited thereto.

In some embodiments, in Formula 1, M may be selected from Ir, Pt, Os, Ti, Zr, Hf, Eu, Tb, and Tm, but is not limited thereto. In some other embodiments, in Formula 1, M may be selected from Ir, Pt, and Os, but is not limited thereto. For example, in Formula 1, M may be Ir, but is not limited thereto.

In Formula 1, $X_{11}$ and $X_{14}$ may be each independently selected from a carbon atom (C) and a nitrogen atom (N). For example, in Formula 1, $X_{11}$ and $X_{14}$ may be C, but are not limited thereto.

In Formula 1, $X_{12}$ and $X_{13}$ may be C.

In Formula 1, $A_{11}$ and $A_{13}$ may be each independently selected from $C_1$-$C_{20}$ heterocyclic groups. For example, in Formula 1, $A_{11}$ and $A_{13}$ may be each independently selected from a pyrrole, an imidazole, a pyrazole, a thiazole, an isothiazole, an oxazole, an soxazole, a triazole, a pyridine, a thiazine, an oxazine, a pyrazine, a pyrimidine, a quinoline, an isoquinoline, a benzoquinoline, a quinoxaline, a quinazoline, a naphthyridine, an indole, a benzimidazole, a benzothiazole, a benzisothiazole, a benzoxazole, a benzisoxazole, a benzothiazine, a benzoxazine, and a triazine, but are not limited thereto.

In some embodiments, in Formula 1, $A_{11}$ and $A_{13}$ may be each independently selected from a pyrrole, an imidazole, a pyrazole, a thiazole, an isothiazole, an oxazole, an isoxazole, a triazole, a pyridine, a thiazine, an oxazine, a pyrazine, a pyrimidine, a quinoline, an isoquinoline, an indole, a benzimidazole, a benzothiazole, a benzisothiazole, a benzoxazole, a benzisoxazole, a benzothiazine, a benzoxazine, and a triazine, but are not limited thereto.

In some embodiments, in Formula 1, $A_{11}$ may be selected from a pyridine, a pyrazine, a pyrimidine, a quinoline, and an isoquinoline, but is not limited thereto. In some other embodiments, in Formula 1, $A_{11}$ may be selected from a pyridine, a pyrimidine, a quinoline, and an isoquinoline, but is not limited thereto.

In some other embodiments, in Formula 1 $A_{13}$ may be selected from a pyrrole, an imidazole, a thiazine, an oxazine, an indole, a benzimidazole, a benzothiazine, and a benzoxazine, but is not limited thereto. In some other embodiments, in Formula 1, $A_{13}$ may be selected from a pyrrole and an indole, but is not limited thereto.

In Formula 1, $A_{12}$ may be selected from a $C_5$-$C_{20}$ cyclic group and a $C_1$-$C_{20}$ heterocyclic group. For example, in Formula 1, $A_{12}$ may be selected from a benzene, a naphthalene, a pyridine, a pyrimidine, a pyrazine, a quinoline, and an isoquinoline, but is not limited thereto.

In some embodiments, in Formula 1, $A_{12}$ may be selected from a benzene and a naphthalene, but is not limited thereto. In some other embodiments, in Formula 1, $A_{12}$ may be a benzene, but is not limited thereto.

In Formula 1, $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), and —N($Q_1$)($Q_2$), wherein $R_{11}$ and $R_{12}$ may be optionally linked to each other to form a saturated or unsaturated ring; and $Q_1$ to $Q_3$ may be each independently selected from a hydrogen, a deuterium, a substituted or unsubstituted $C_1$-$C_{20}$ alkyl group, a substituted or unsubstituted $C_6$-$C_{20}$ aryl group, a substituted or unsubstituted monovalent non-aromatic condensed polycyclic group, and a substituted or unsubstituted monovalent non-aromatic condensed heteropolycyclic group.

For example, in Formula 1, $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ slkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyi group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyi group, a pyridazinyl group, an isoindolyl group, an indolyl group, an indazolyl group, a purinyl group, a quinolinyl group, an isoquinolinyl group, a benzoqutnolinyl group, a qumoxalinyl group, a quinazolinyl group, a cinnolinyl group, a carbazolyl group, a phenanthrolinyl group, a benzimidazotyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a tnazinyl group, a dibenzofuranyl group, a dibenzothiophenyl group, a benzocarbazolyl group, a dibenzocarbazolyl group, and an imidazopyridinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyi group, a pyridazinyl group, an isoindolyl group, an indolyl group, an indazolyl group, a purinyl group, a quinolinyl group, an isoquinolinyl group, a benzoquinolinyl group, a qumoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and —C(=O)(Q$_1$), —Si(Q$_1$)(Q$_2$)(Q$_3$), and —N(Q$_1$)(Q$_2$), wherein Q$_1$ to Q$_3$ may be each independently selected from substituted or unsubstituted C$_1$-C$_{20}$ alkyl groups. However, embodiments are not limited thereto.

In some embodiments, in Formula 1, R$_{11}$ to R$_{13}$ may be each independently selected from a hydrogen, a deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, and a tert-butoxy group, a C$_1$-C$_{20}$ alkyl group and a C$_1$-C$_{20}$ alkoxy group, each substituted with at least one of a deuterium, —F, —Cl, —Br, —I, a cyano group, a phenyl group, and a naphthyl group, a phenyl group and a naphthyl group, and a phenyl group and a naphthyl group, each substituted with at least one of a deuterium, —F, —Cl, —Br, —I, —CD$_3$, —CD$_2$H, —CDH$_2$, —CF$_3$, —CF$_2$H, —CFH$_2$, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, a tert-butoxy group, a phenyl group, and a naphthyl group, However, embodiments are not limited thereto, In some other embodiments, in Formula 1, R$_{11}$ to R$_{13}$ may be each independently selected from a hydrogen, a deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, and a tert-butoxy group. However, embodiments are not limited thereto.

In some embodiments, in Formula 1, R$_{11}$ and R$_{12}$ may be linked to each other to form a group represented by Y$_{11}$, and Y$_{11}$ may be selected from O, S, and groups represented by Formulae 8-1 to 8-5. However, embodiments are not limited thereto.

8-1

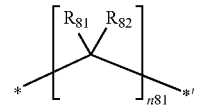

8-2

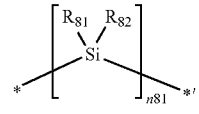

8-3

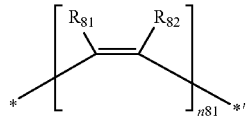

8-4

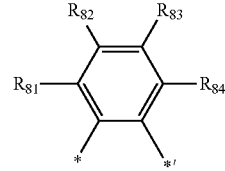

8-5

In Formulae 8-1 to 8-5, R$_{81}$ to R$_{84}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, and a C$_1$-C$_{20}$ alkoxy group, a C$_1$-C$_{20}$ alkyl group and a Ci-Cm slkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyi group, a pyridazinyl group, an isoindolyl group, an indolyl group, an indazolyl group, a purinyl group, a quinolinyl group, an isoquinolinyl group, a benzoqutnolinyl group, a qumoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group;

n81 may be selected from 1, 2, 3, 4, and 5; and

* and *' may be each independently a binding site with an adjacent atom.

In some embodiments, in Formulae 8-1 to 8-5, $R_{81}$ to $R_{84}$ may be each independently selected from a hydrogen, a deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, and a tert-butoxy group, a $C_1$-$C_{20}$ alkyl group and a $C_1$-$C_{20}$ alkoxy group, each substituted with at least one of a deuterium, —F, —Cl, —Br, —I, a cyano group, a phenyl group, and a naphthyl group, a phenyl group and a naphthyl group, and a phenyl group and a naphthyl group, each substituted with at east one of a deuterium, —F, —Cl, —Br, —I, —CD$_3$, —CD$_2$H, —CDH$_2$, —CF$_3$, —CF$_2$H, —CFH$_2$, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, a tert-butoxy group, a phenyl group, and a naphthyl group; and n81 may be selected from 1 and 2. However, embodiments are not limited thereto.

In some other embodiments, in Formula 1, $R_{11}$ and $R_{12}$ may be linked to each other to form a group represented by $Y_{11}$, and $Y_{11}$ may be selected from O, S, and groups represented by Formulae 9-1 to 9-15. However, embodiments are not limited thereto.

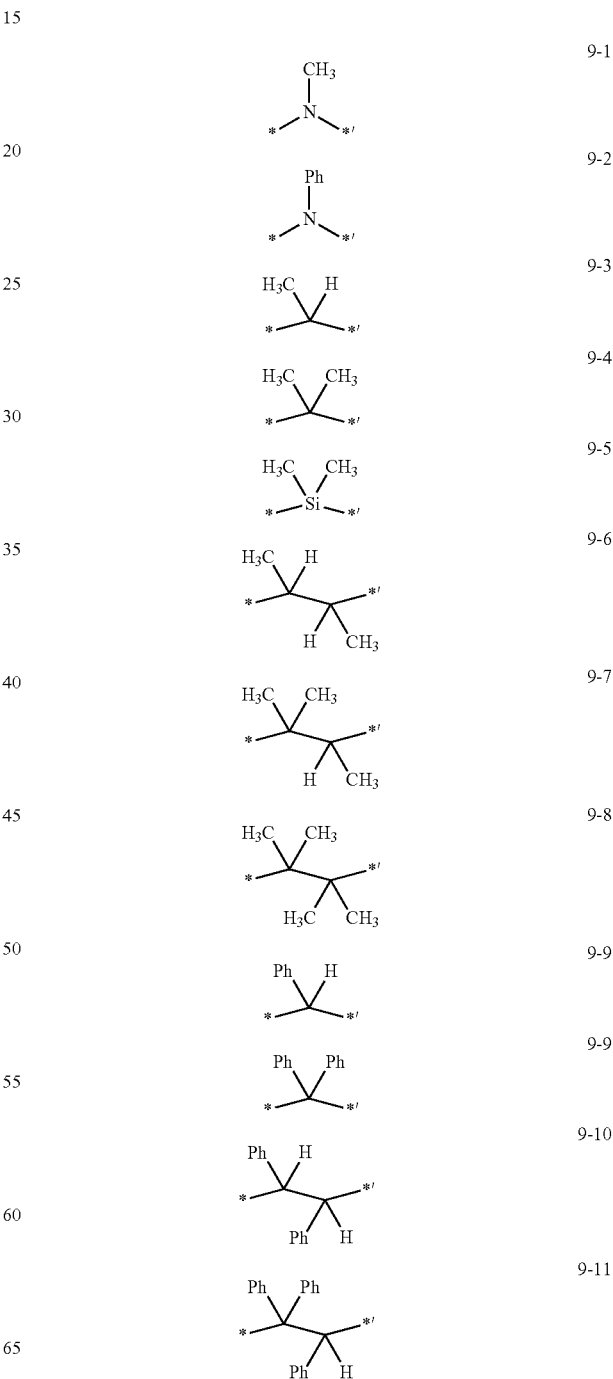

-continued 9-12

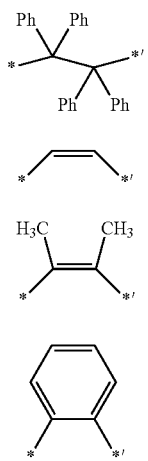

9-13

9-14

9-15

In Formulae 9-1 to 9-15,

Ph may be a phenyl group; and

* and *' may be each independently a binding site with an adjacent atom.

In Formula 1, n may be selected from 1, 2, and 3.

In Formula 1, L may be selected from a monodentate ligand and a bidentate ligand.

Non-limiting examples of the monodentate ligand are an iodide ion, a bromide ions, a chloride ion, a sulfide, a thiocyanate ion, a nitrate ion, an azide ion, a hydroxide on, a cyanide ion, $H_2O$, an acetonitrile, a pyridine, an ammonia, a carbon monoxide, $PPh_3$, $PPh_2CH_3$, $PPh(CH_3)_2$, and $P(CH_3)_3$.

Non-limiting examples of the bidentate ligand are an oxalate, an acetylacetonate, a picolinic acid, a 1,2-bis(diphenylphosphino)ethane (dppe), a 1,1-bis(diphenylphosphino)methane (dppm), a glycinate, and an ethylenediamine.

For example, in Formula 1, L may be a ligand represented by one of Formulae 2-1 to 2-6. However, embodiments are not limited thereto.

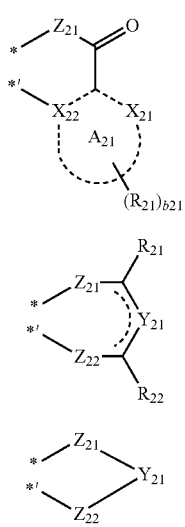

2-1

2-2

2-3

-continued

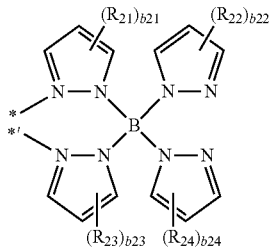

2-4

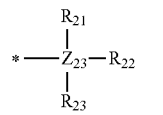

2-5

2-6

In Formulae 2-1 to 2-6, $A_{21}$ may be selected from a $C_5$-$C_{20}$ cyclic group and a $C_1$-$C_{20}$ heterocyclic group;

$X_{21}$ and $X_{22}$ may be each independently selected from C and N;

$Y_{21}$ may be selected from a single bond, a double bond, a substituted or unsubstituted $C_1$-$C_5$ alkylene group, a substituted or unsubstituted $C_2$-$C_5$ alkenylene group, and a substituted or unsubstituted $C_6$-$C_{10}$ arylene group;

$Z_{21}$ and $Z_{22}$ may be each independently selected from N, O, $N(R_{25})$, $P(R_{25})(R_{26})$, and $AS(R_{26})(R_{26})$;

$Z_{23}$ may be selected from phosphorus (P) and arsenic (As);

$R_{21}$ to $R_{26}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b21 to b24 may be each independently selected from 1 2, and 3; and

* and *' may be each independently a binding site with an adjacent atom.

In some embodiments, in Formula 2-1, $A_{21}$ may be selected from a benzene, a naphthalene, a pyridine, a pyrimidine, a triazine, a quinoline, and an isoquinoline, but is not limited thereto.

In some embodiments, in Formulae 2-2 and 2-3, $Y_{21}$ may be selected from a substituted or unsubstituted methylene group and a substituted or unsubstituted phenylene group, but is not limited thereto.

In some embodiments, in Formula 2-5, $Z_{23}$ may be P, but is not limited thereto.

In some embodiments, in Formulae 2-1 to 2-6, $R_{21}$ to $R_{26}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyrazinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a qumoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium. —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group and an imidazopyridinyl group. However, embodiments are not limited thereto.

In some embodiments, in Formula 1, L may be a ligand represented by one of Formulae 3-1 to 3-4, but is not limited thereto.

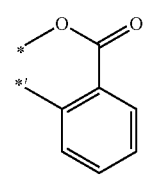

3-1

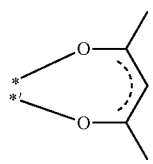

3-2

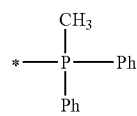

3-3

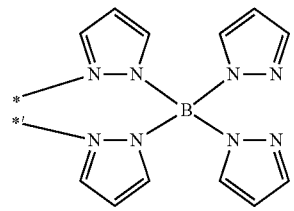

3-4

In Formulae 3-1 to 3-4,

Ph may be a phenyl group: and

* and *' may be each independently a binding site with an adjacent atom.

In Formula 1, m may be selected from 0, 1, 2, 3, and 4,

For example, in Formula 1, m may be selected from 0, 1, and 2, but is not limited thereto.

The organometallic compound of Formula 1 may be represented by one of Formulae 1-1 and 1-2. However, embodiments are not limited thereto.

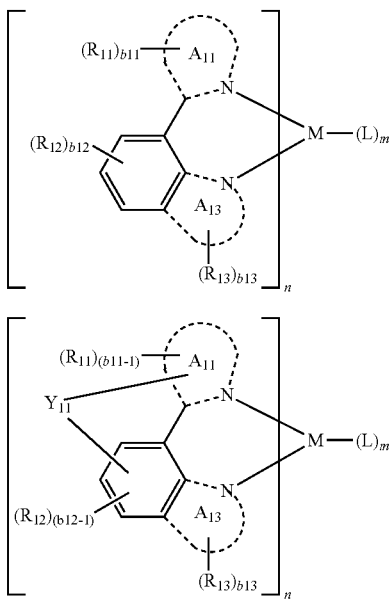

1-1

1-2

In Formulae 1-1 and 1-2, $M, A_{11}, A_{13}, R_{11}$ to $R_{13}$, b11 to b13, n, L, and m may be defined the same as those in Formula 1; and $Y_{11}$ may be selected from O, S, and groups represented by O, S and Formulae 8-1 to 8-5:

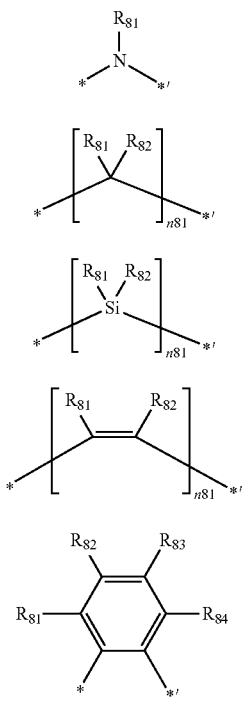

8-1

8-2

8-3

8-4

8-5 wherein, in Formulae 8-1 to 8-5, $R_{81}$ to $R_{84}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a sail thereof, a sulfonic acid group or a salt thereof, a phosphoric acid group or a salt thereof, a $C_1$-$C_{20}$ alkyl group, and a $C_1$-$C_{20}$ alkoxy group.

a $C_1$-$C_{20}$ alkyl group, and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyi group, a pyridazinyl group, an isoindolyl group, an indolyl group, an indazolyl group, a purinyl group, a quinolinyl group, an isoquinolinyl group, a benzoquinolinyl group, a quinoxahnyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyndazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothio phenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyi group, a triazinyl group, a dibenzofuranyl group, a dibenzothiophenyl group, a benzocarbazolyl group, a dibenzocarbazolyl group and an imidazopyridinyl group;

n81 may be selected from 1, 2, 3, 4, and 5; and

* and *' may be each independently a binding site with an adjacent atom.

In some embodiments, the organometallic compound of Formula 1 is represented by one of Formulae 1-11 to 1-22. However, embodiments are not limited thereto.

1-11
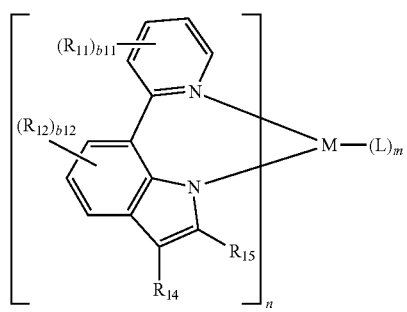

1-12
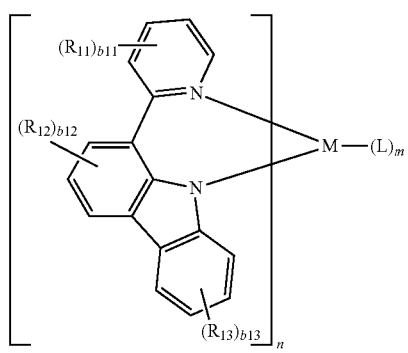

1-13
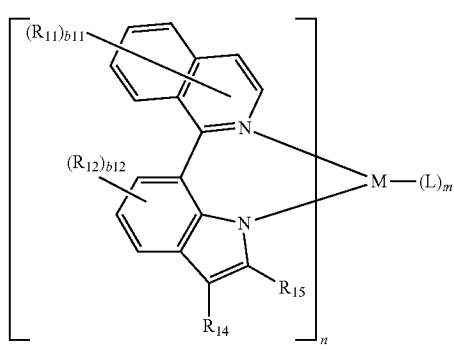

1-14
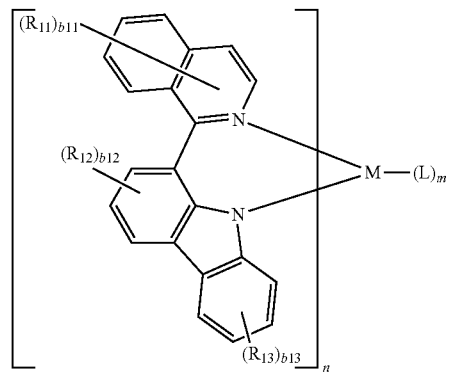

1-15
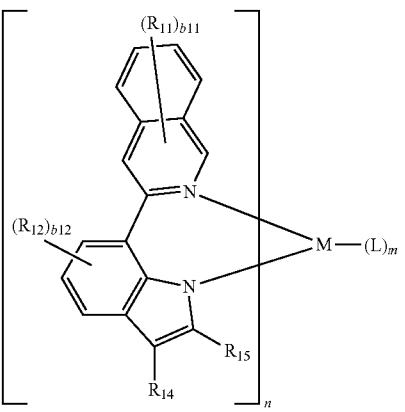

1-16
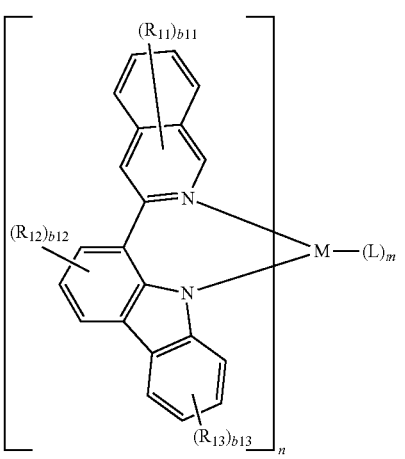

1-17
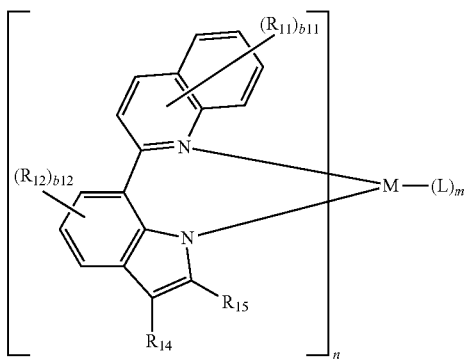

1-18
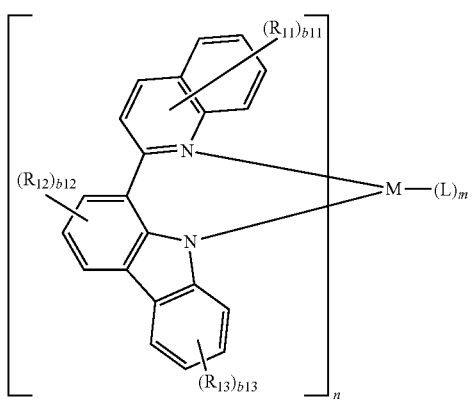
1-19
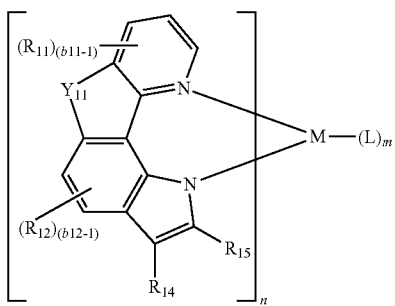
1-20
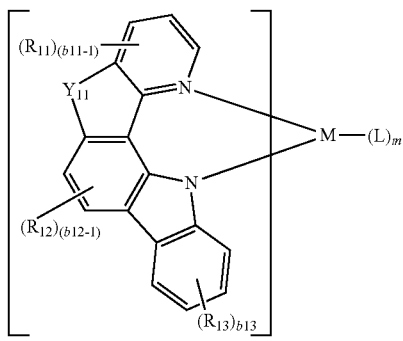
1-21
1-22
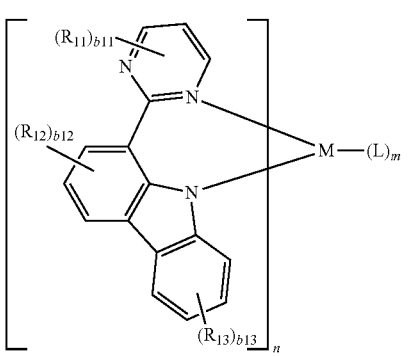
wherein, in Formulae 1-11 to 1-22,
M, $R_{11}$ to $R_{13}$, b11 to b13, n, L, and m may be defined the same as those in Formula 1;
$R_{14}$ and $R_{15}$ may be each independently defined the same as $R_{11}$ in Formula 1; and
$Y_{11}$ may be selected from O, S, and groups represented by Formulae 9-1 to 9-15.
9-1
9-2
9-3
9-4
9-5
9-6
9-7
9-8
9-9
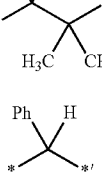

9-9
9-10
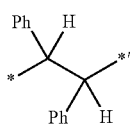
9-11
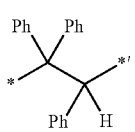
9-12
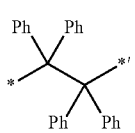
9-13
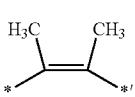
9-14
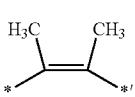
9-15
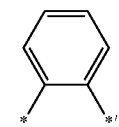
In Formulae 9-1 to 9-15,
Ph may be a phenyl group; and
* and *' may be each independently a binding site with an adjacent atom.
In some embodiments, the organometallic compound of Formula 1 may be represented by one of Formulae 1-31 to 1-42. However, embodiments are not limited thereto.
1-31
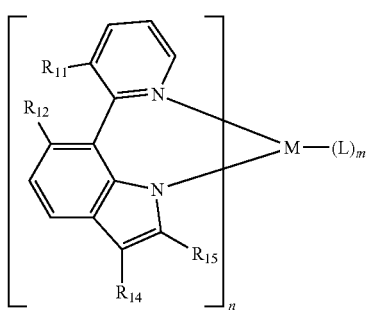
1-32
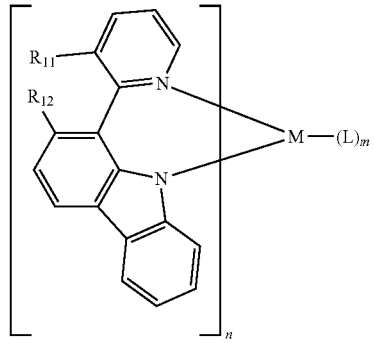
1-33
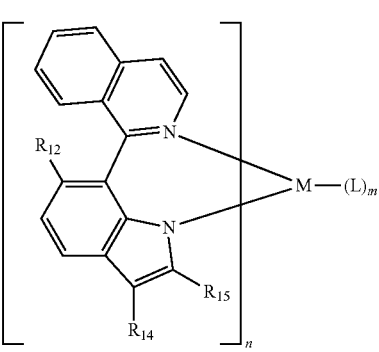
1-34
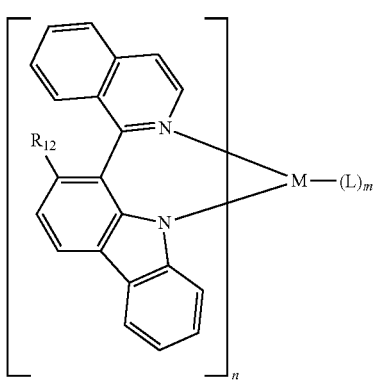
1-35
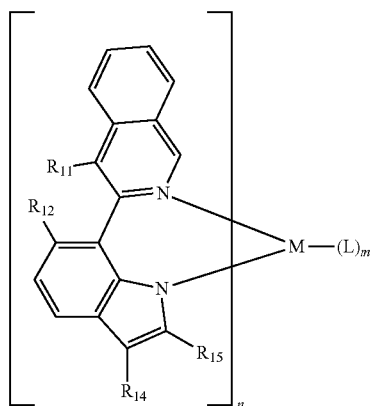

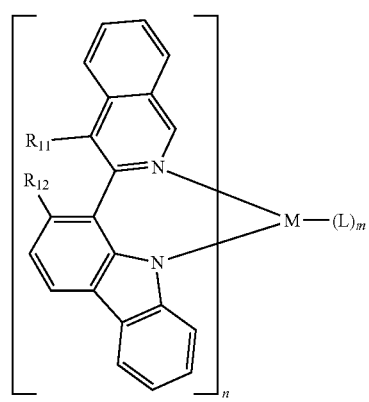
1-36
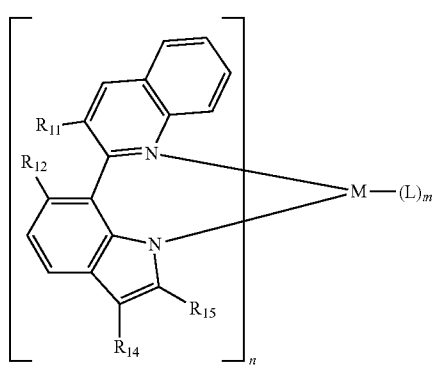
1-37
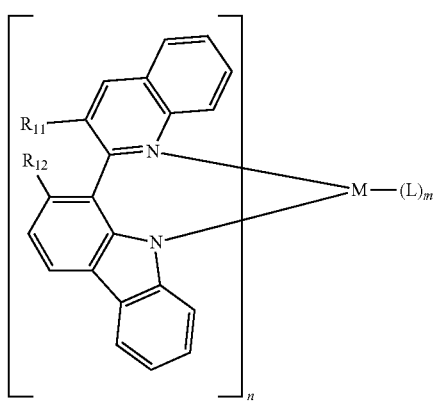
1-38
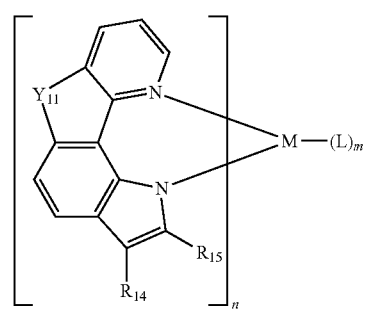
1-39
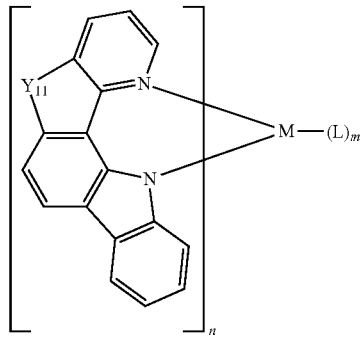
1-40
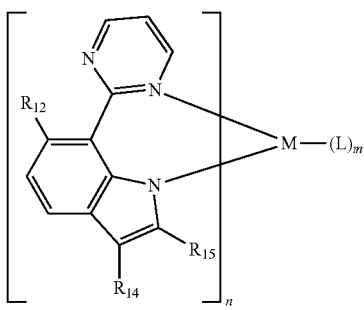
1-41
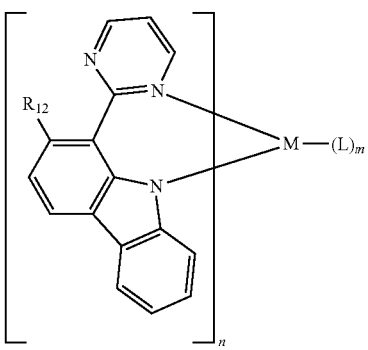
1-42
In Formulae 1-31 to 1-42,
$R_{11}$ to $R_{13}$, b11 to b13, n, and m may be defined the same as those in Formula 1;
$R_{14}$ and $R_{15}$ may be each independently defined the same as $R_{11}$ in Formula 1; and
$Y_{11}$ may be is selected from O, S, and groups represented by Formulae 9-1 to 9-15.
9-1
9-2
9-3
9-4

9-5
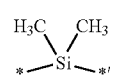

9-6
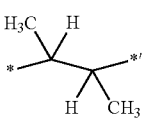

9-7
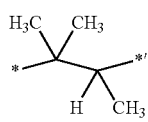

9-8
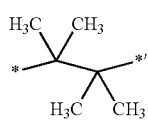

9-9
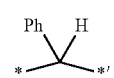

9-9
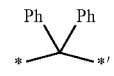

9-10
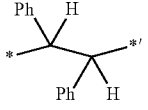

9-11
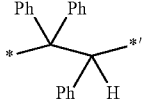

9-12
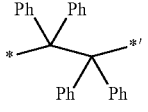

9-13
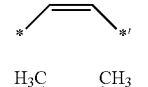

9-14
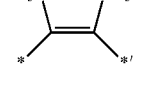

9-15
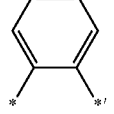

In Formulae 9-1 to 9-15,

Ph may be a phenyl group; and

* and *' may be each independently a binding site with an adjacent atom;

L may be a ligand represented by one of Formulae 3-1 to 3-4:

3-1
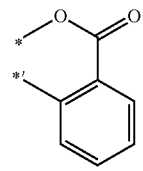

3-2
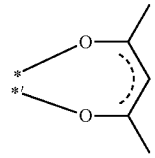

3-3
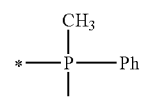

3-4
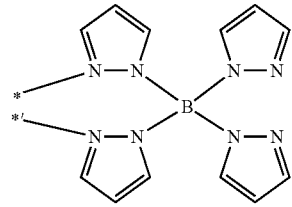

wherein, in Formulae 3-1 to 3-4,

Ph may be a phenyl group: and

* and *' may be each independently a binding site with an adjacent atom.

In some embodiments, the organometallic compound represented by Formula 1 may be selected from Compounds 1 to 30, but is not limited thereto.

1
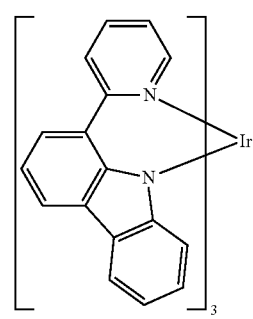

2
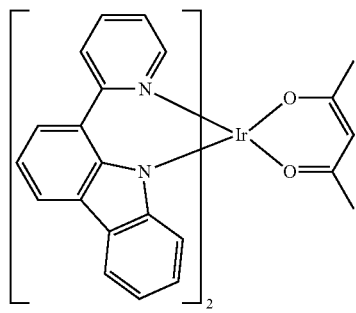

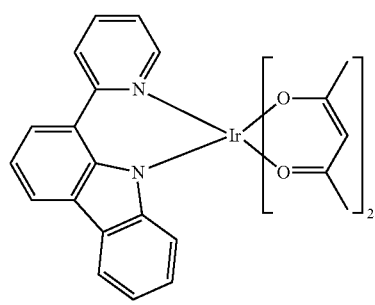
3
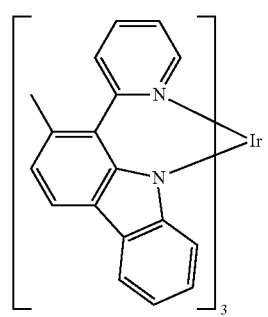
4
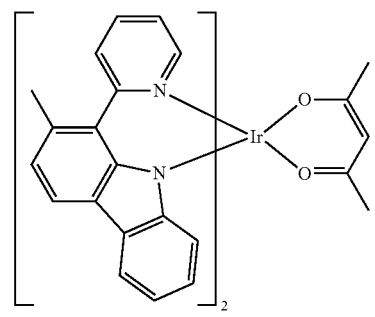
5
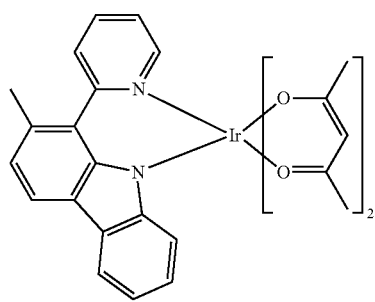
6
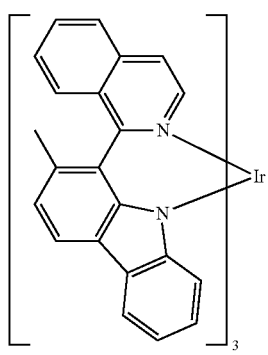
7
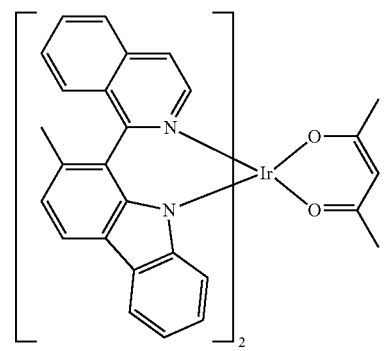
8
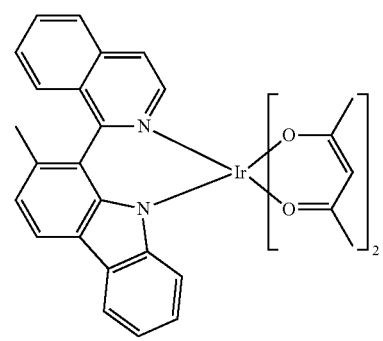
9
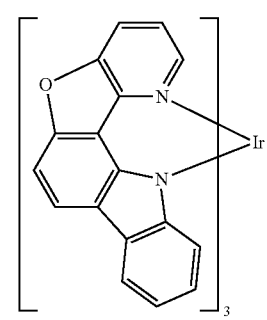
10
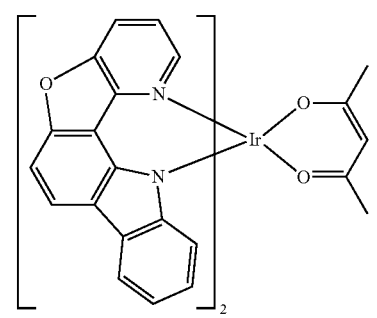
11
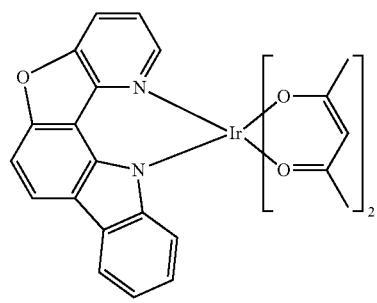
12

13
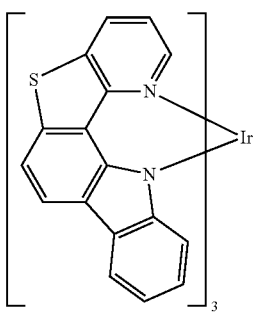
14
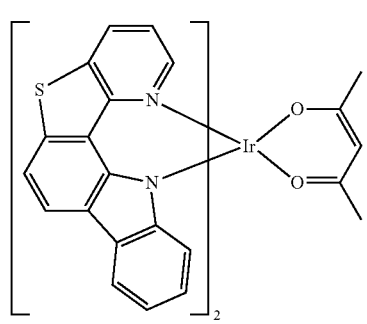
15
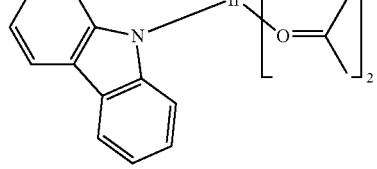
16
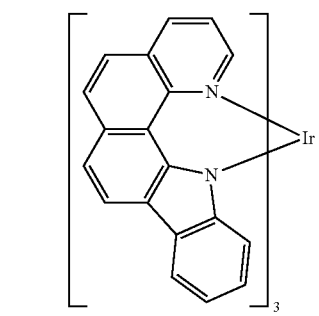
17
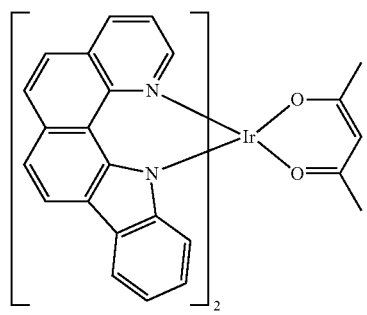
18
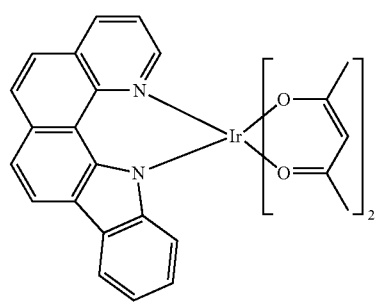
19
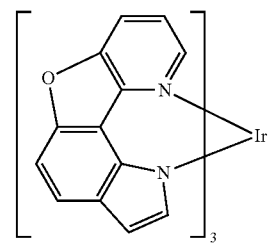
20
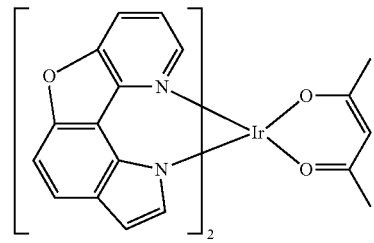
21
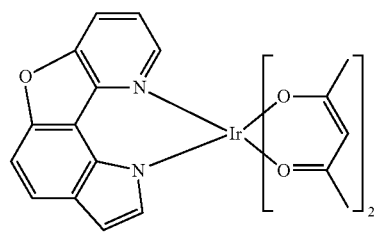
22
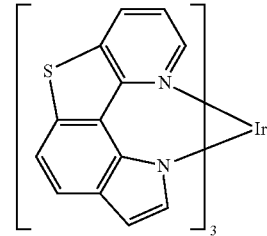
23
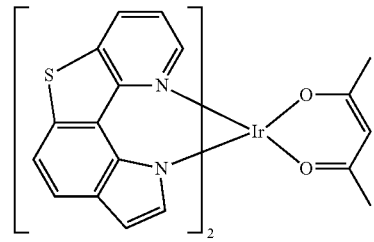

-continued

24
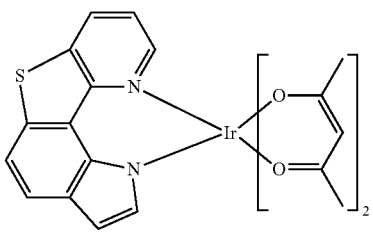

25
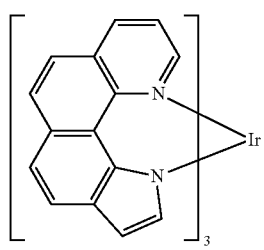

26
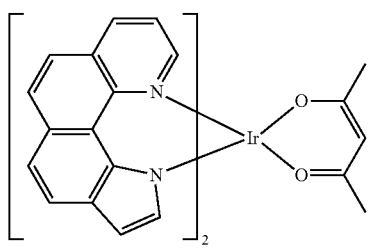

27
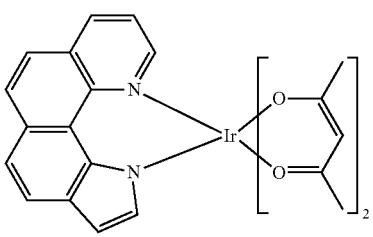

28
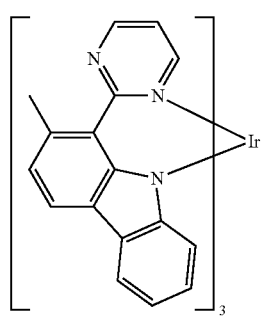

29
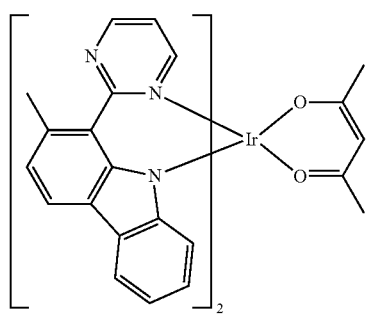

-continued

30
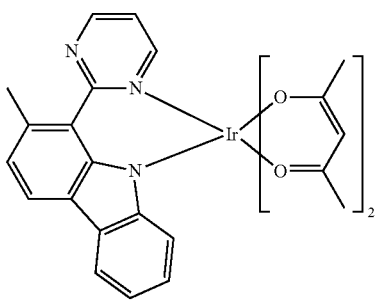

In any of the above-described embodiments, the organometallic compound represented by Formula 1 may include a 6-membered ring consisting of M, N, $X_{11}$, $X_{12}$, $X_{13}$, and N, as shown in Formula 1, wherein the 6-membered ring may include two nitrogen (N) atoms. Therefore, the maximum emission wavelength of the organometallic compound represented by Formula 1 can be readily controlled, and an organic light-emitting device including the organometallic compound of Formula 1 may have improved efficiency.

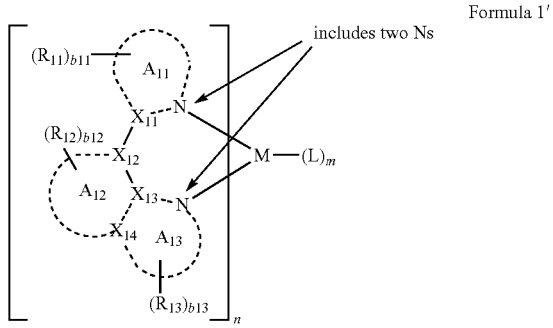

Formula 1'

As an example, the highest occupied molecular orbital (HOMO) energy levels, the lowest unoccupied molecular orbital (LUMO) energy levels, and triplet ($T_1$) energy levels of some of the organometallic compounds of Formula 1 were evaluated using a density functional theory (DFT) method with a Gaussian program (by structure optimization at B3LYP/6-31G(d,p) level). The results are shown in Table 1.

TABLE 1

| Compound No. | HOMO (eV) | LUMO (eV) | $T_1$ energy level (eV) |
|---|---|---|---|
| 1 | −4.546 | −1.699 | 2.123 |
| 2 | −4.418 | −1.648 | 1.971 |
| 3 | −4.421 | −1.429 | 2.056 |
| 4 | −4.488 | −1.701 | 2.089 |
| 5 | −4.353 | −1.644 | 1.931 |
| 8 | −4.375 | −1.947 | 1.686 |
| 10 | −4.837 | −1.882 | 2.198 |
| 11 | −4.756 | −1.704 | 2.227 |
| 12 | −4.576 | −1.487 | 2.172 |
| 13 | −4.746 | −1.866 | 2.134 |
| 14 | −4.669 | −1.777 | 2.109 |
| 16 | −4.534 | −1.854 | 1.966 |
| 17 | −4.448 | −1.893 | 1.827 |
| 20 | −4.920 | −1.592 | 2.280 |
| 26 | −4.701 | −1.759 | 2.114 |

Referring to Table 1, the organometallic compounds of Formula 1 were found to have appropriate HOMO and LUMO energy levels for organic light-emitting devices and to be material having an appropriate $T_1$ energy level for visible light emission.

A method of synthesizing the organometallic compound represented by Formula 1 may be apparent to one of ordinary skill in the art by referring to Synthesis Examples described herein.

The organometallic compound of Formula 1 may be appropriate for use as a material for an organic layer of an organic light-emitting device, for example, as a dopant of an EML.

According to another aspect of the present disclosure, an organic light-emitting device includes:

a first electrode, a second electrode, and an organic layer disposed between the first electrode and the second electrode, wherein the organic layer includes an EML and at least one organometallic compound of Formula 1 according to any of the above-described embodiments.

The organometallic compound of Formula 1 may be used between a pair of electrodes of an organic light-emitting device. For example, the organometallic compound of Formula 1 may be included in the EML. The organometallic compound of Formula 1 may serve as a dopant in the EML, and the EML may further include a host (i.e., the amount of the organometallic compound of Formula 1 may be smaller than the amount of the host).

As used herein, "(for example, the organic layer) including at least one organometallic compound" means that "(the organic layer) including an organometallic compound of Formula 1, or at least two different organometallic compounds of Formula 1."

For example, the organic layer of the organic light-emitting device may include only Compound 1 as the organometallic compound. For example, Compound 1 may be included in the EML of the organic light-emitting device. In some embodiments, the organic layer of the organic light-emitting device may include Compounds 1 and 2 as the organometallic compound. For example, Compounds 1 and 2 may be included both in the EML.

The first electrode may be an anode as a hole injection electrode, and the second electrode may be a cathode as an electron injection electrode. In some embodiments, the first electrode may be a cathode as an electron injection electrode, and the second electrode may be an anode as a hole injection electrode.

For example, the first electrode may be an anode, the second electrode may be a cathode, and the organic layer may include:

i) a hole transport region disposed between the first electrode and the emission layer, wherein the hole transport region includes at least one of a hole injection layer, a hole transport layer, and an electron blocking layer; and ii) an electron transport region disposed between the emission layer and the second electrode, wherein the electron transport region includes at least one of a hole blocking layer, an electron transport layer, and an electron injection layer.

FIG. 1 is a schematic view of an organic light-emitting device 10 according to an embodiment of the present disclosure. Hereinafter, a structure of an organic light-emitting device according to an embodiment of the present disclosure and a method of manufacturing the same will now be described with reference to FIG. 1. Referring to FIG. 1, the organic light-emitting device 10 has a structure in which a first electrode 11, an organic layer 15, and a second electrode 19 are sequentially stacked in this order on a substrate (not shown).

The substrate (not shown) may be disposed under the first electrode 11 or on the second electrode 190 in FIG. 1. The substrate may be any substrate that is used in conventional organic light-emitting devices. In some embodiments the substrate may be a glass substrate or a transparent plastic substrate with strong mechanical strength, thermal stability, transparency, surface smoothness, ease of handling, and water resistance.

The first electrode 11 may be formed by depositing or sputtering a first electrode-forming material on the substrate. The first electrode 11 may be an anode. A material having a high work function may be selected as a material for the first electrode 11 to facilitate hole injection. The first electrode 11 may be a reflective electrode, a semi-transmissive electrode, or a transmissive electrode. For example, the material for the first electrode 11 may be indium tin oxide (ITO), indium zinc oxide (IZO), tin oxide ($SnO_2$), or zinc oxide (ZnO). In some embodiments, the material for the first electrode 11 may be a metal, for example, magnesium (Mg), aluminum (Al), aluminum-lithium (Al—Li), calcium (Ca), magnesium-indium (Mg—In), magnesium-silver (Mg—Ag), or the like.

The first electrode 11 may have a single-layer structure or a multi-layer structure including at least two layers. For example, the first electrode 11 may have, but not limited to, a three-layered structure including ITO, Ag, and ITO layers.

The organic layer 15 may be disposed on the first electrode 11.

The organic layer 15 may include at least one a hole transport region; an EML, and an electron transport region.

The hole transport region may be disposed between the first electrode 11 and the EML.

The hole transport region may include at least one of a hole injection layer (HIL), a hole transport layer (HTL), an electron blocking layer (EBL), and a buffer layer.

The hole transport region may only include the HIL or the HTL. In some embodiments, the electron transport region may have a structure including a HIL/HTL or a HIL/HTL/EBL, wherein the layers forming the structure of the electron transport region may be sequentially stacked on the first electrode 10 in the stated order.

When the hole transport region includes the HIL, the HIL may be formed on the first electrode 11 by any of a variety of methods, for example, vacuum deposition, spin coating, casting, Langmuir-Blodgett (LB) deposition, or the like, When the HIL is formed using vacuum deposition, vacuum deposition conditions may vary depending on the material that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Angstroms per second (Å/sec), However, the deposition conditions are not limited thereto.

When the HIL is formed using spin coating, the coating conditions may vary depending on the material that is used to form the HIL, and the desired structure and thermal properties of the HIL to be formed. For example, the coating rate may be in the range of about 2,000 revolutions per minute (rpm) to about 5,000 rpm, and a temperature at which heat treatment is performed to remove a solvent after coating may be in a range of about 80° C. to about 200° C.However, the coating conditions are not limited thereto.

Conditions for forming the HTL and the EBL may be the same as those for the HIL described above.

In some embodiments, the hole transport region may include at least one of m-MTDATA, TDATA, 2-TNATA, methylated NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate)(PEDOT/PSS), polyaniline/camphor sulfonic add (Pani/CSA), polyaniline/poly(4-styrenesulfonate) (PANI/PSS), a compound represented by Formula 201, and a compound represented by Formula 202.

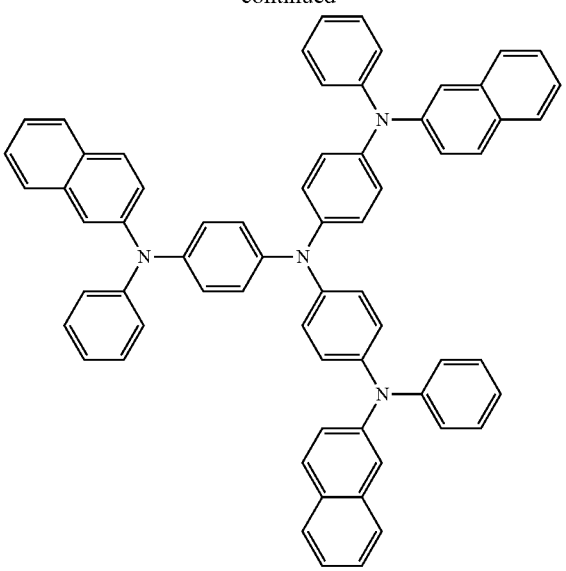

2-TNATA

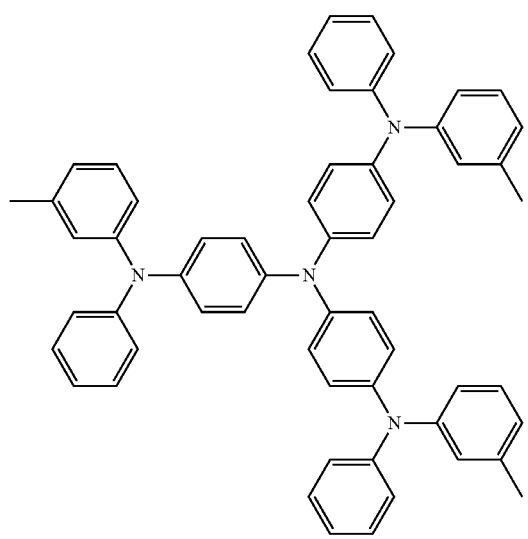

m-MTDATA

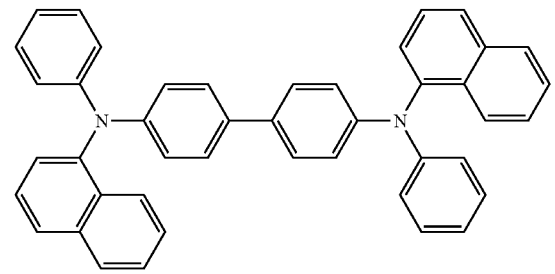

NPB

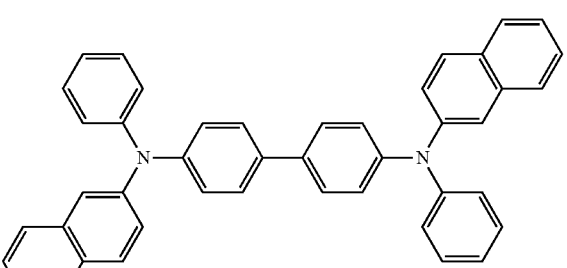

β-NPB

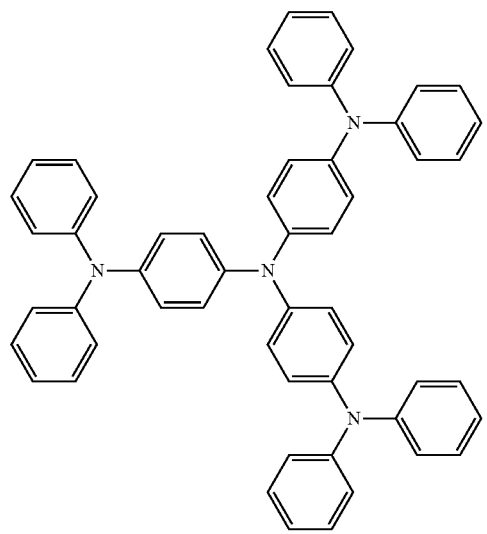

TDATA

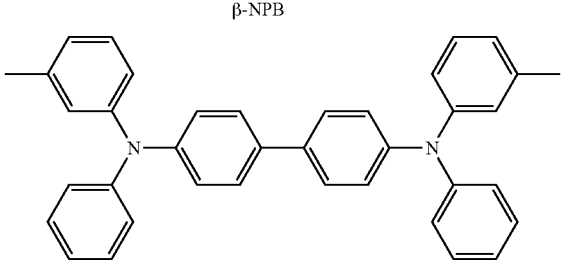

TPD

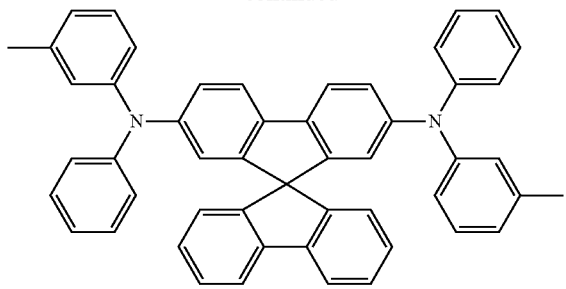

Spiro-TPD

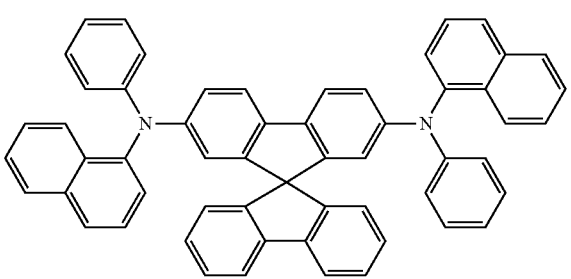

Spiro-NPB

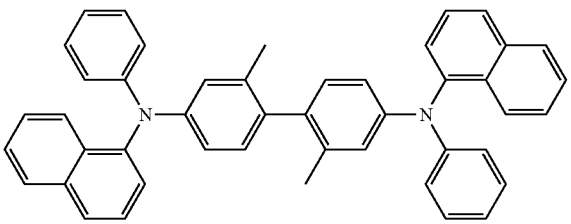

methylated NPB

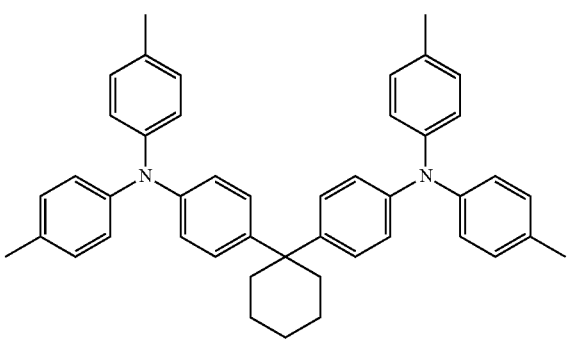

TAPC

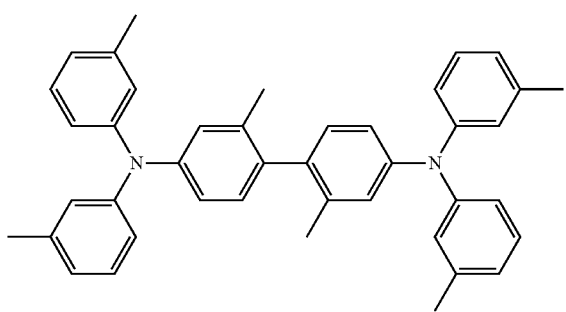

HMTPD

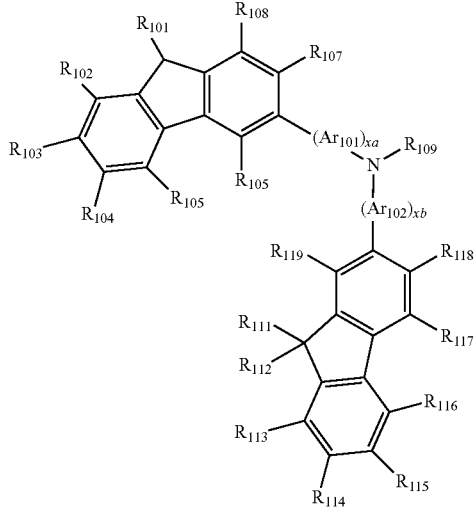

Formula 201

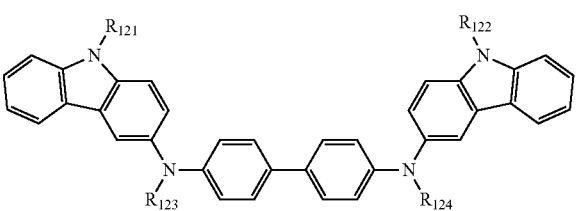

Formula 202

In Formula 201 $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer from 0 to 5, for example, may be 0, 1, or 2. For example, xa may be 1, and xb may be 0, but are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like), a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group, and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201 above, $R_{109}$ may be selected from a phenyl group, a naphthyl group, an anthracenyl group, and a pyridinyl group, or a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{23}$ alkoxy group, a phenyl group, a naphthyl group, an anthracenyl group, and a pyridinyl group.

In some embodiments, the compound of Formula 201 may be a compound represented by Formula 201A, but is not limited thereto.

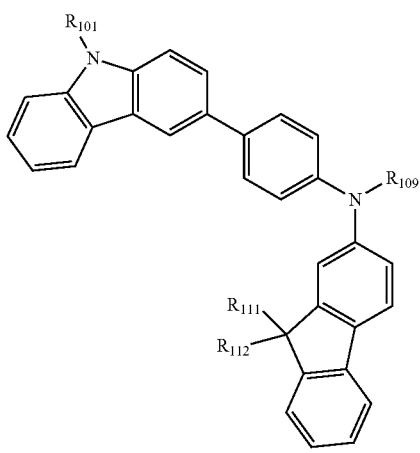

Formula 201A

In Formula 201A, $R_{101}$, $R_{111}$, $R_{112}$, and $R_{109}$ may be defined the same as described above.

For example, the compound of Formula 201 and the compound of Formula 202 may be Compounds HT1 to HT20, but are not limited thereto.

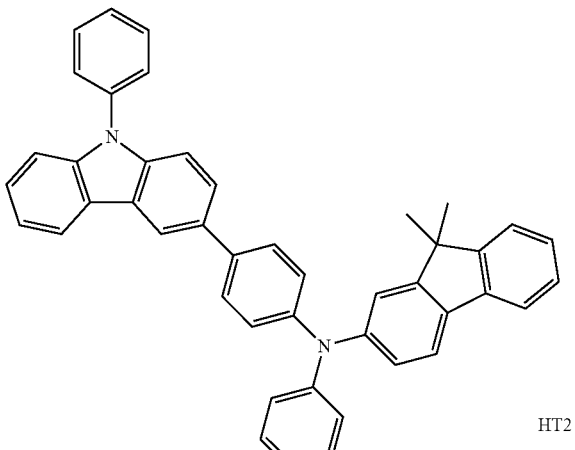

HT1

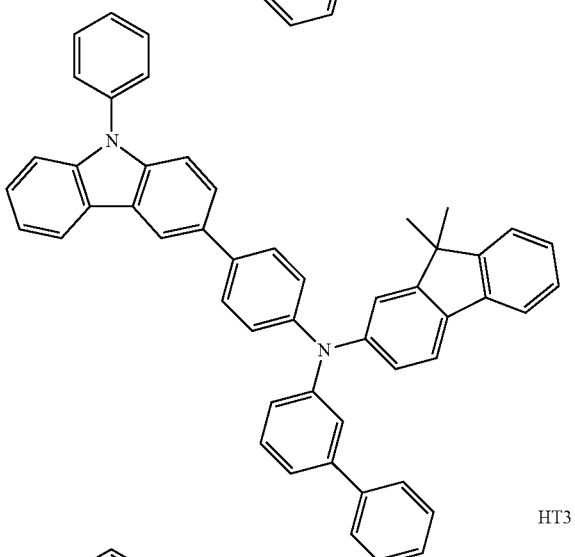

HT2

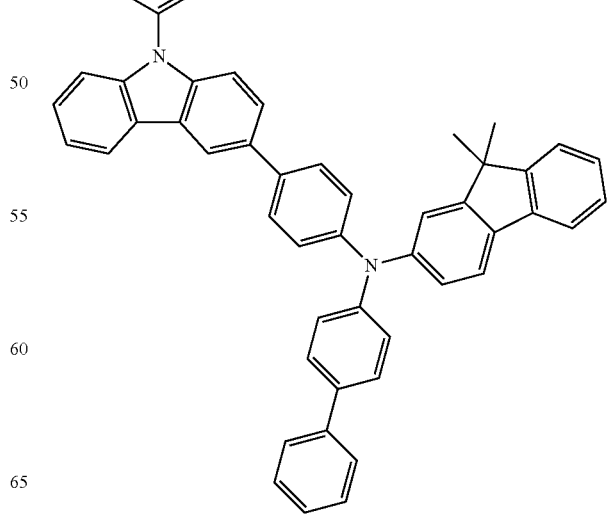

HT3

HT4
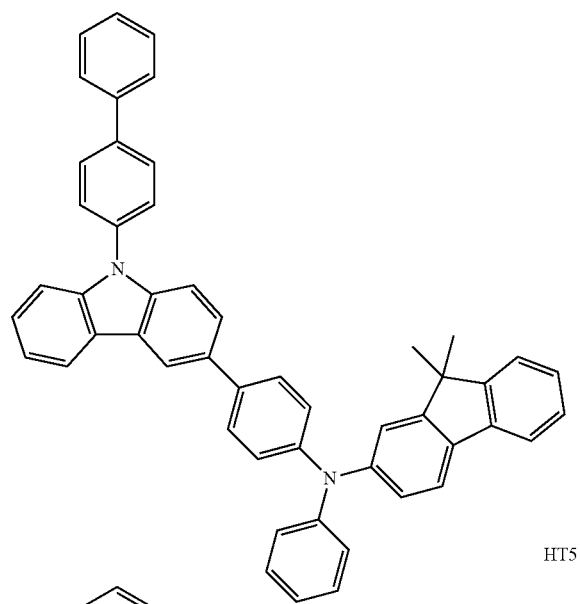
HT5
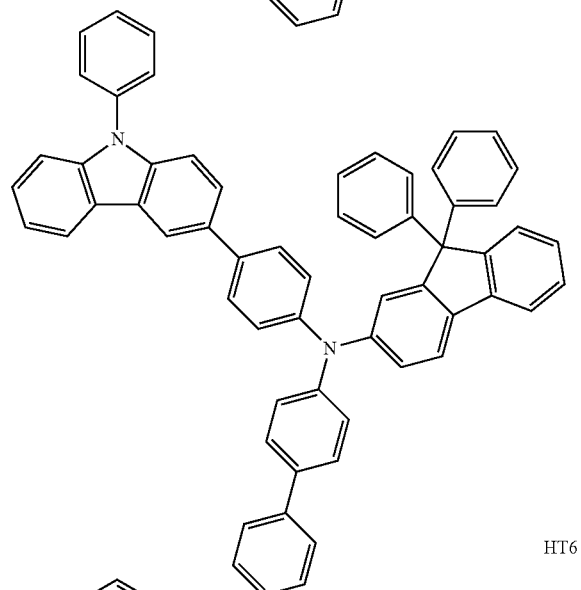
HT6
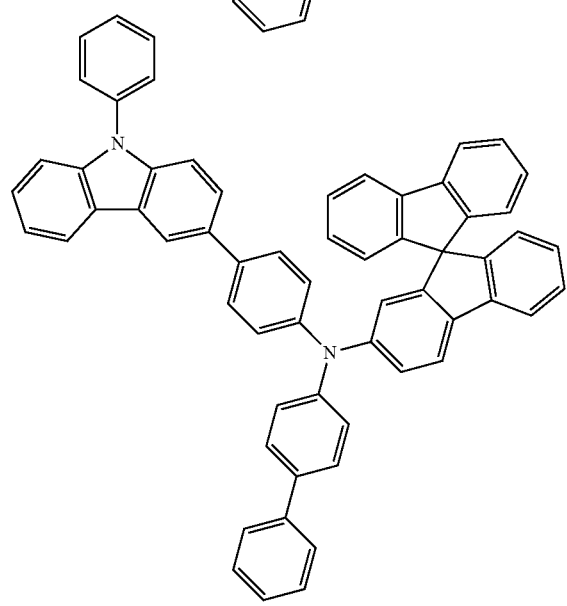
HT7
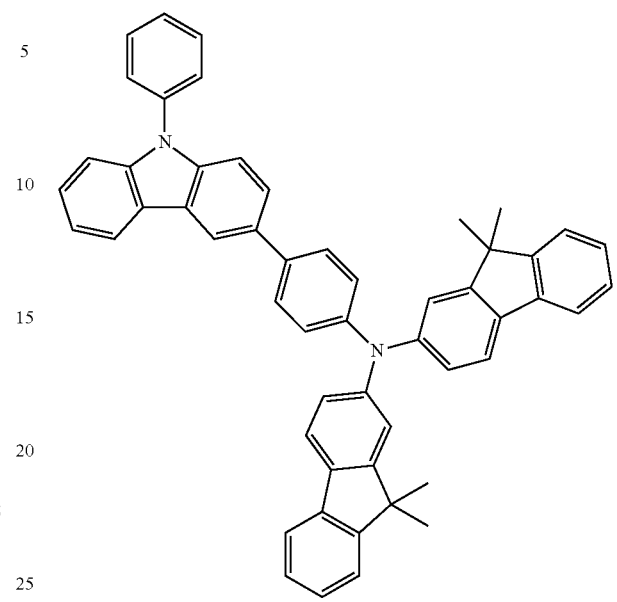
HT8
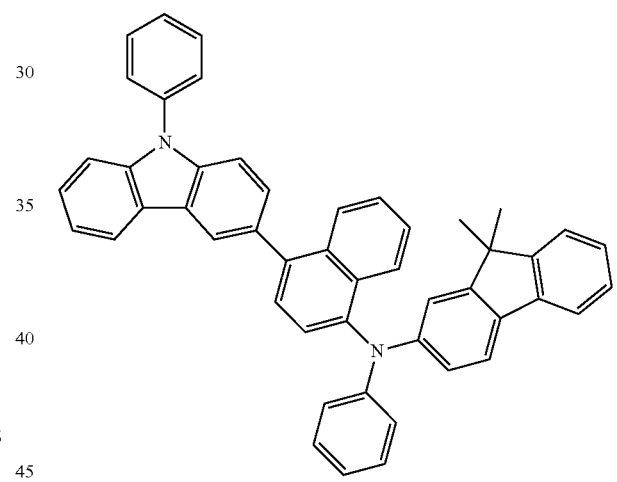
HT9
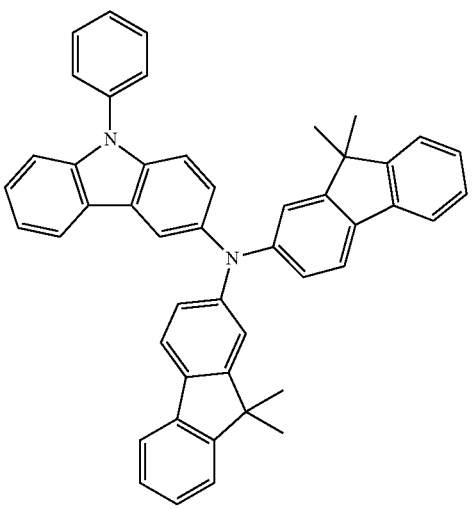

HT10
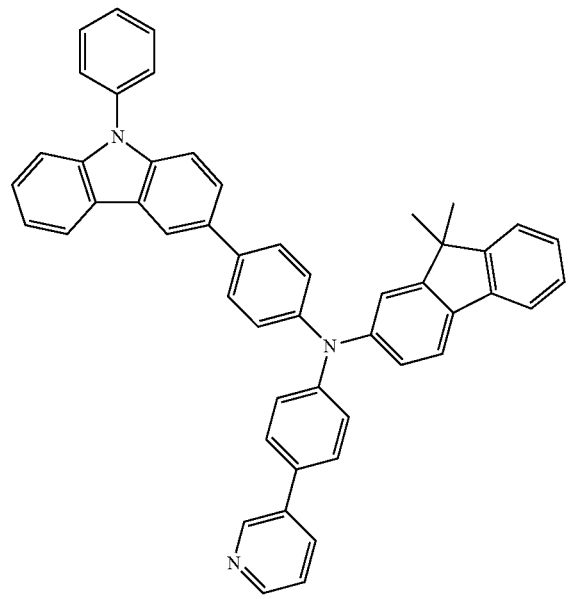
HT11
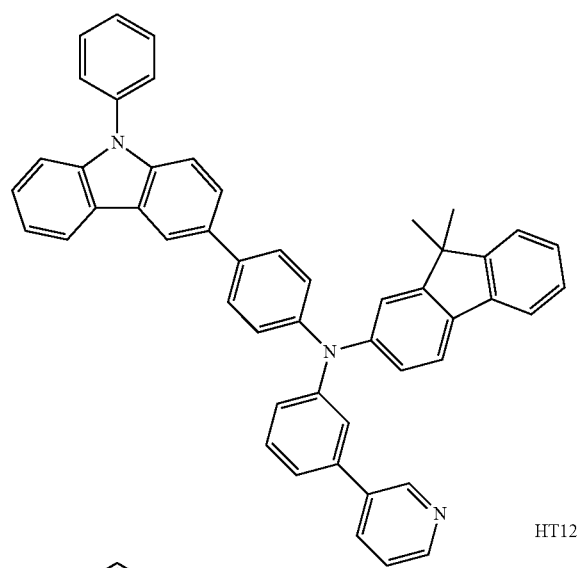
HT12
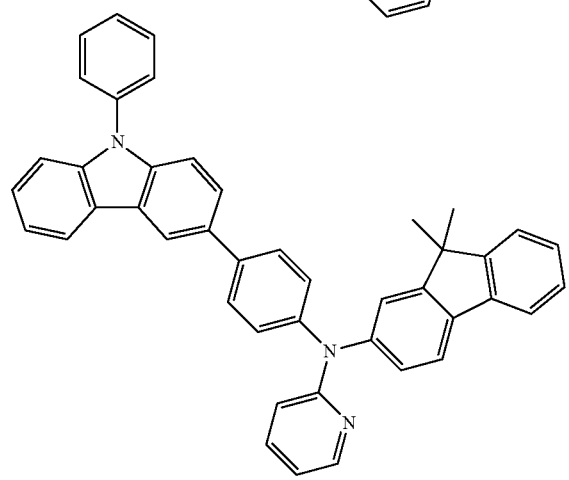
HT13
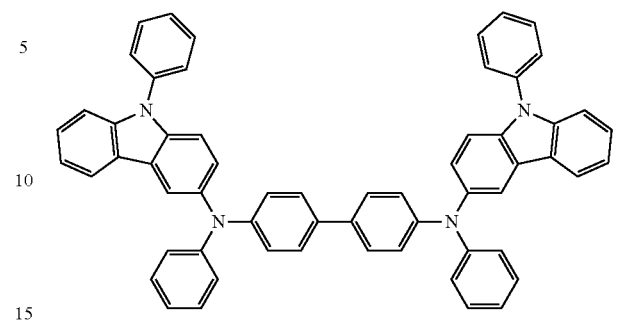
HT14
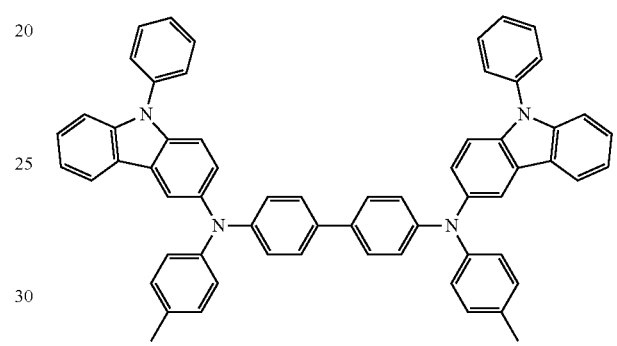
HT15
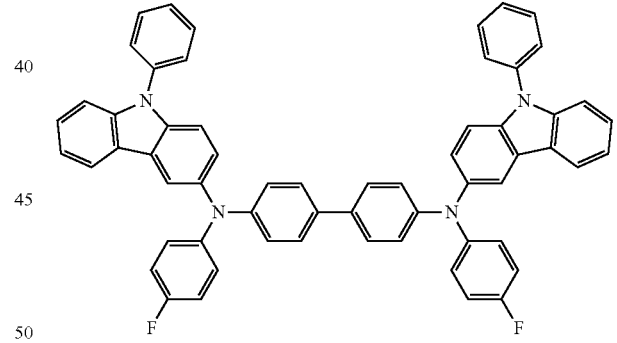
HT16
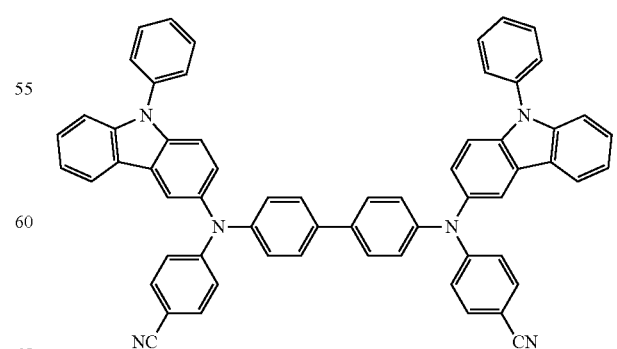

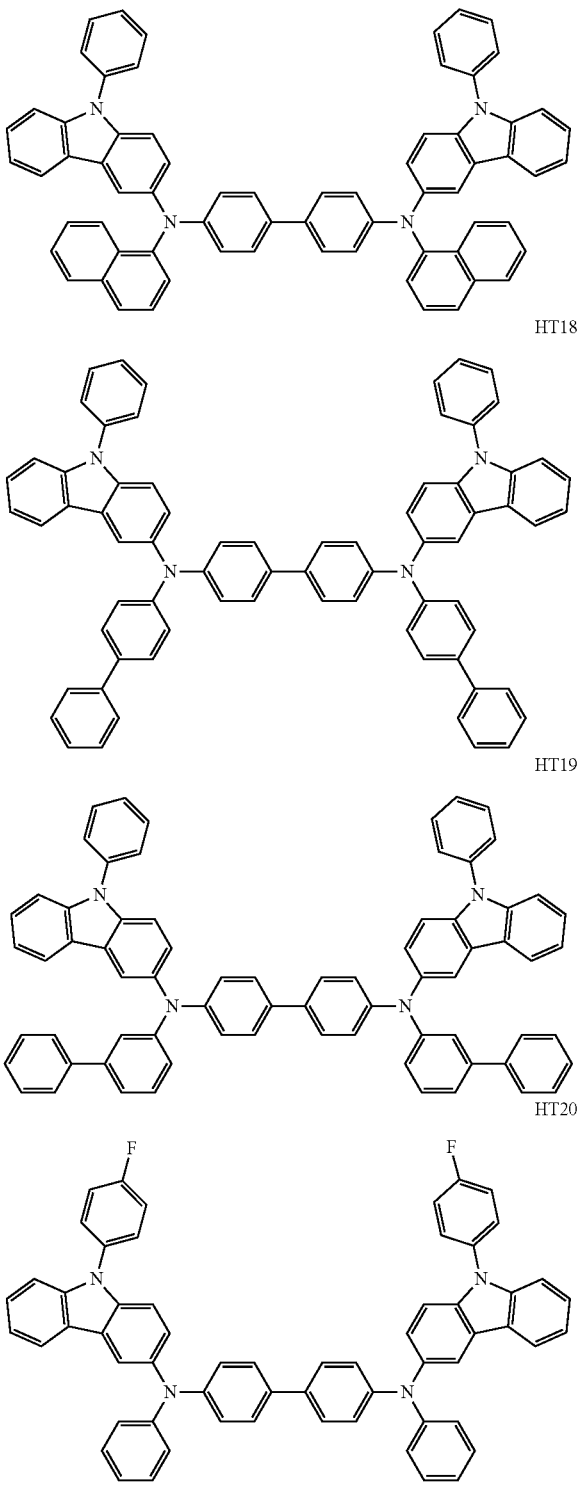

HT17

HT18

HT19

HT20

The thickness of the hole transport region may be from about 100 Angstrom (Å) to about 10,000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and the thickness of the HTL may be from about 50 Å to about 2,000 Å, and in some embodiments, from about 100 Å to about 1,500 Å. While not wishing to be bound by a theory, it is understood that when the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound HT-D1 and the like.

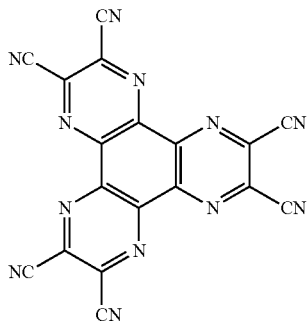

Compound HT-D1

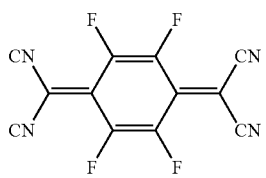

F4-TCNQ

The hole transport region may further include a buffer layer.

The buffer layer may compensate for an optical resonance distance of light according to a wavelength of the light emitted from the EML, and thus may increase efficiency of the OLED.

The EML may be formed on the hole transport region by using vacuum deposition, spin coating, casting, LB deposition, or the like. When the EML is formed using vacuum deposition or spin coating, the conditions for deposition and coating may be similar to those for the formation of the HIL, though the conditions for the deposition and coating may vary depending on the material that is used to form the EML.

When the hole transport region includes an electron blocking layer (EBL), a material for the EBL may be selected from the materials listed above as available for the hole transport region and host materials that will be described later, but are not limited thereto. For example, when the hole transport region includes an EBL, the material for the EBL may be mCP.

The EML may include a host and a dopant. The dopant may include an organometallic compound represented by Formula 1. The host may include at least one of TPBi, TBADN, AND (referred to also as "DNA"), CBP, CDBP, TCP, Mcp, Compound H50, and Compound H51.

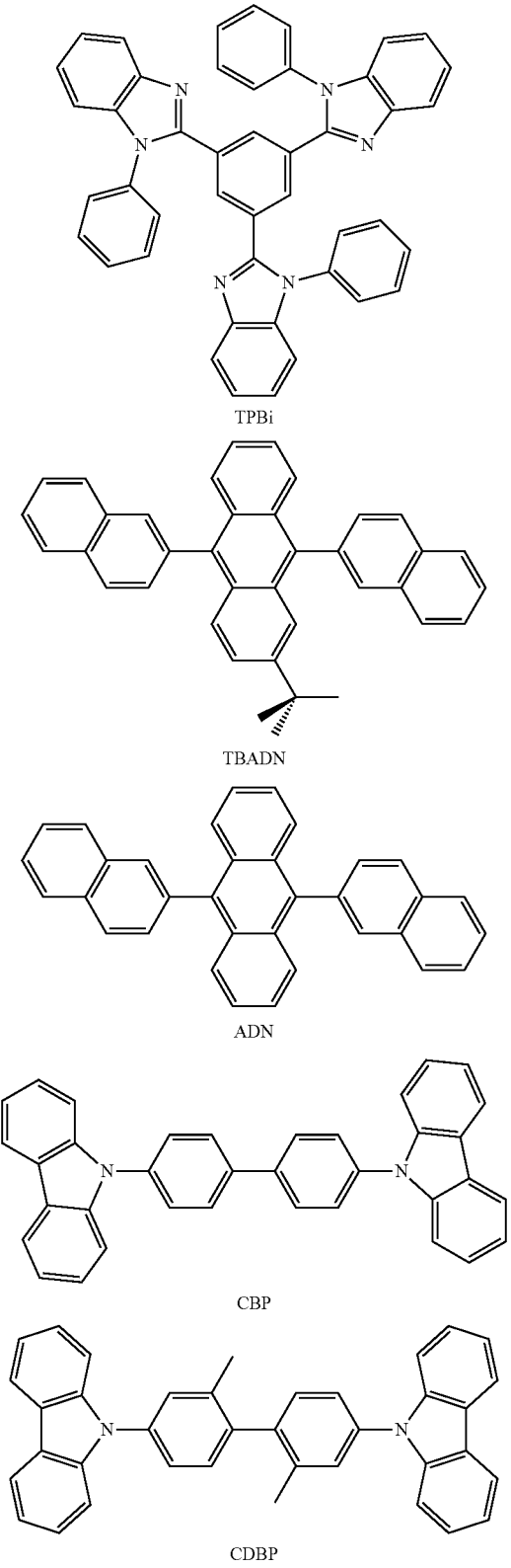

TPBi

TBADN

ADN

CBP

CDBP

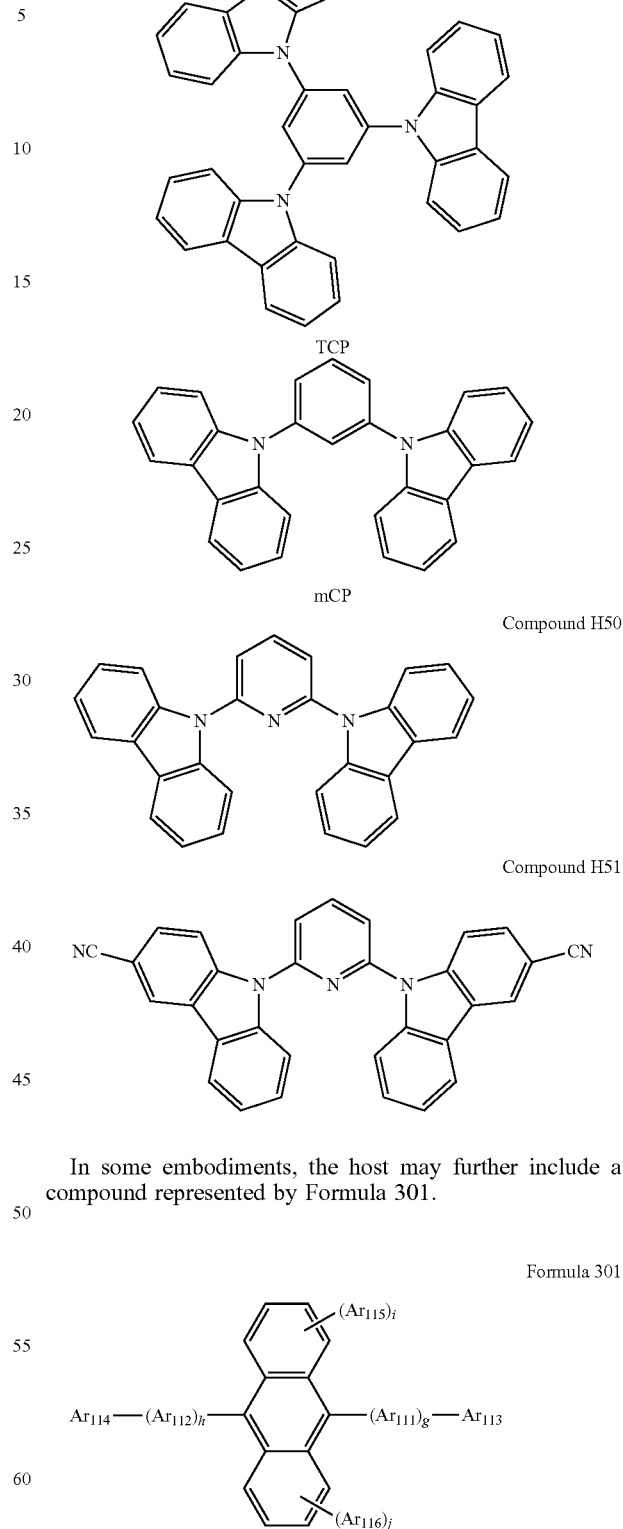

TCP mCP

Compound H50

Compound H51

In some embodiments, the host may further include a compound represented by Formula 301.

Formula 301

In Formula 301, $Ar_{111}$ and $Ar_{112}$ may be each independently selected from
a phenylene group, a naphthylene group, a phenanthrenylene group, and a pyrenylene group, and a phenylene group, a naphthylene group, a phenanthrenylene group, and a pyrenylene group, each substituted with at least one of a phenyl group, a naphthyl group, and an anthracenyl group.

In Formula 301, $Ar_{113}$ to $Ar_{116}$ may be each independently selected from a $C_1$-$C_{10}$ alkyl group, a phenyl group, a naphthyl group, a phenanthrenyl group, and a pyrenyl group, and a phenyl group, a naphthyl group, a phenanthrenyl group, and a pyrenyl group, each substituted with at least one of a phenyl group, a naphthyl group, and an anthracenyl group.

In Formula 301, g, h, I, and j may be each independently an integer of 0 to 4, for example, 0, 1, or 2.

For example, in Formula 301, $Ar_{113}$ to $Ar_{116}$ may be each independently selected from a $C_1$-$C_{10}$ alkyl group substituted with at least one of a phenyl group, a naphthyl group, and an anthracenyl group, a phenyl group, a naphthyl group, an anthracenyl group, a pyrenyl group, a phenanthrenyl group, and a fluorenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group, and

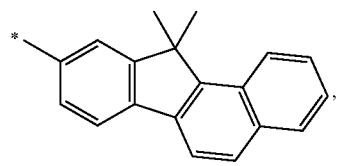 [SMILES: Cc1ccc2c(c1)C(C)(C)c1c-2ccc2ccccc12]

but are not limited thereto.

In some embodiments, the host may include a compound represented by Formula 302.

Formula 302

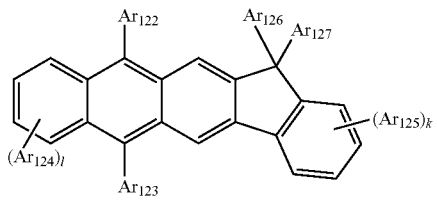

In Formula 302 $Ar_{122}$ to $Ar_{125}$ may be defined the same as $Ar_{113}$ in Formula 301.

In Formula 302, $Ar_{126}$ and $Ar_{127}$ may be each independently a $C_1$-$C_{10}$ alkyl group (for example, a methyl group, an ethyl group, or a propyl group).

In Formula 302, k and l may be each independently an integer of 0 to 4. For example, k and l may be each independently 0, 1, or 2.

The compound of Formula 301 and the compound of Formula 302 may include compounds H1 to H42, but are not limited thereto.

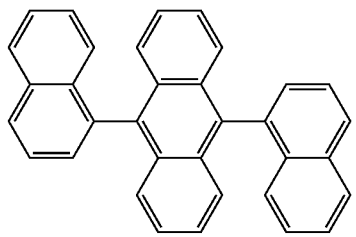
H1

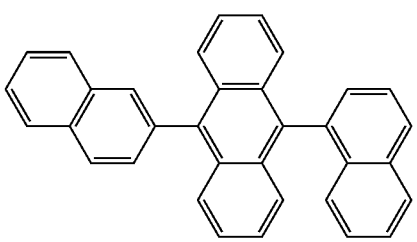
H2

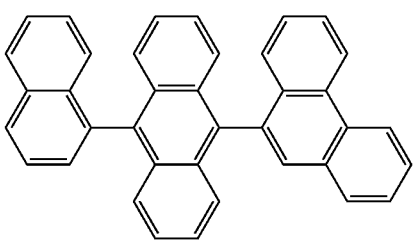
H3

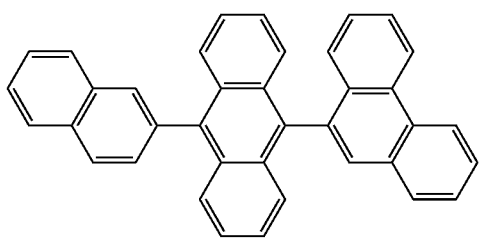
H4

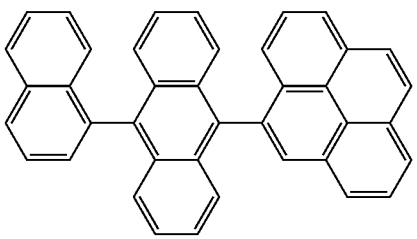
H5

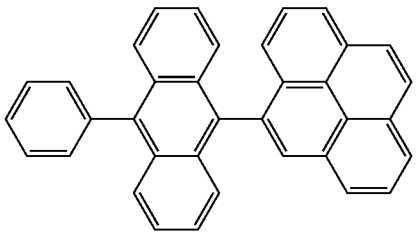
H6

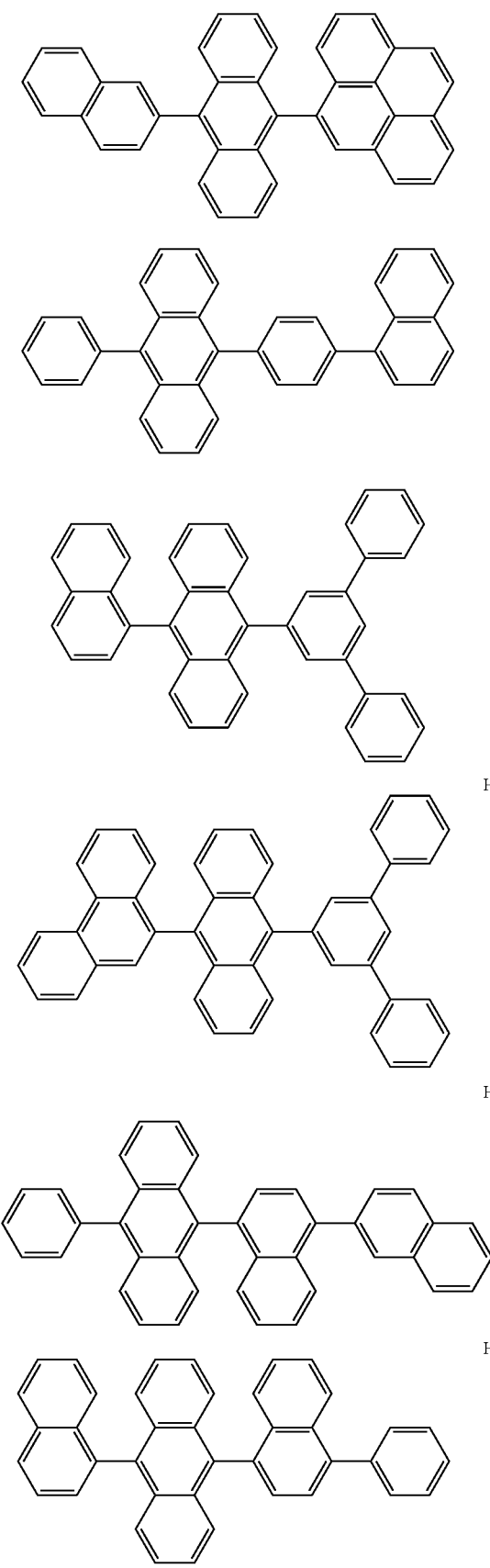
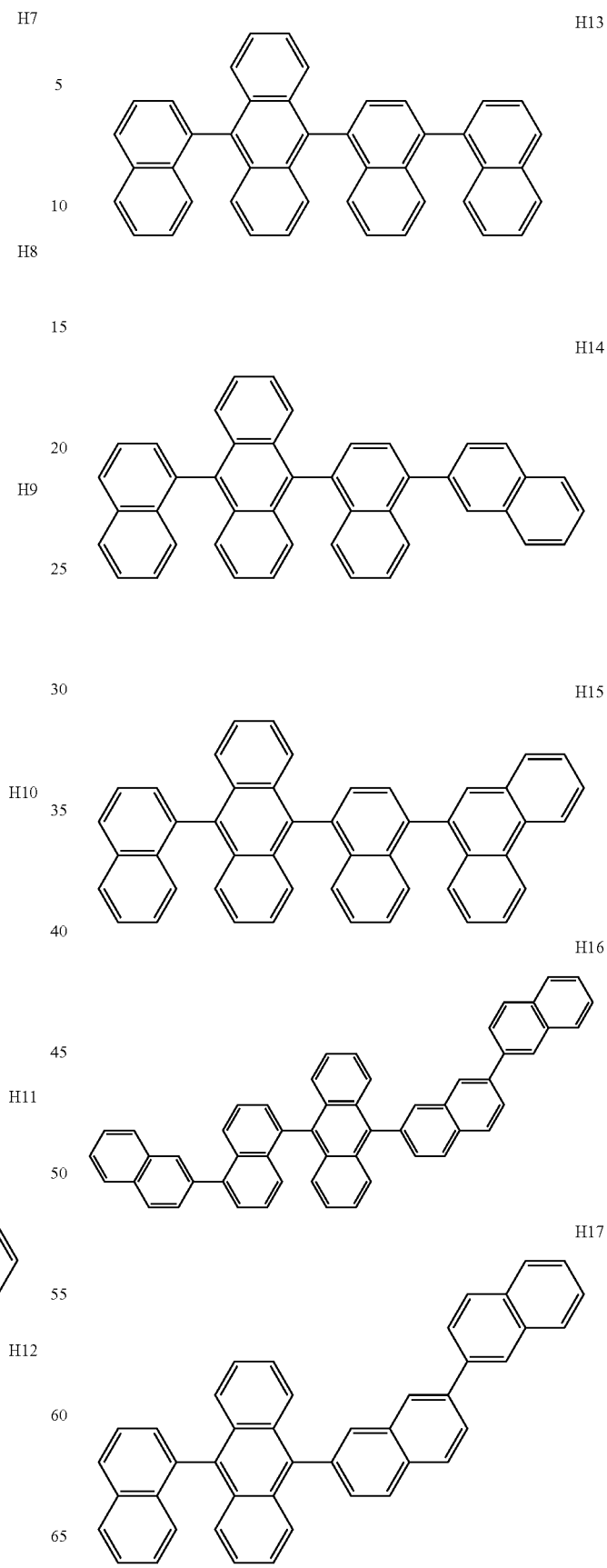

H18
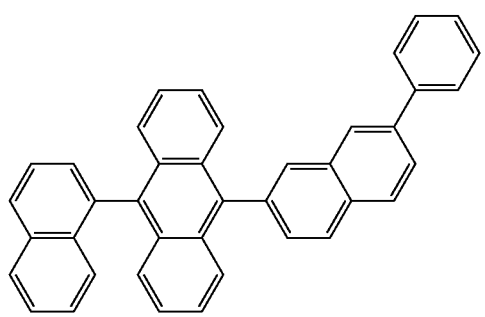
H19
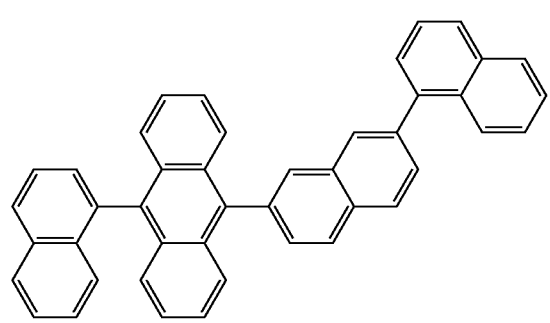
H20
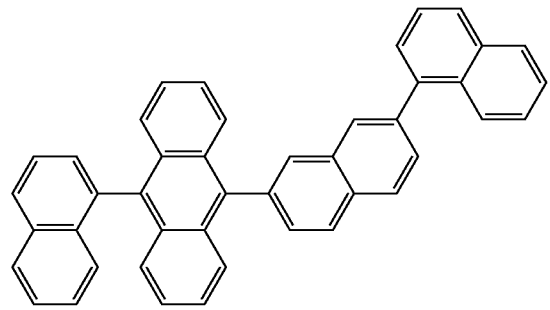
H21
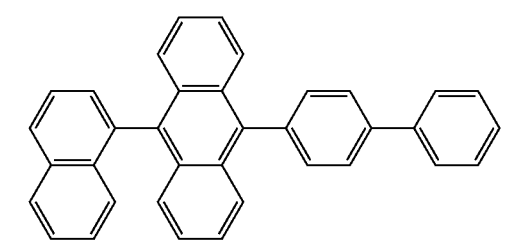
H22
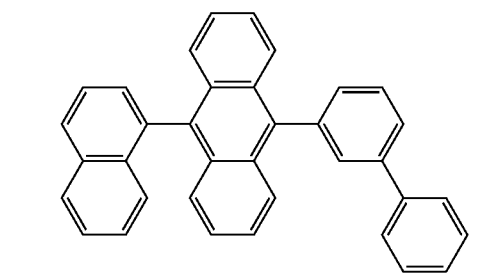
H23
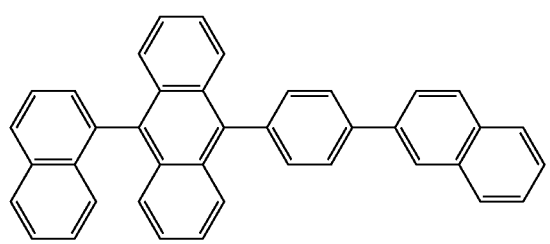
H24
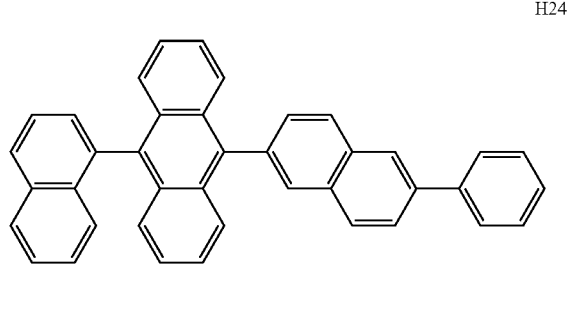
H25
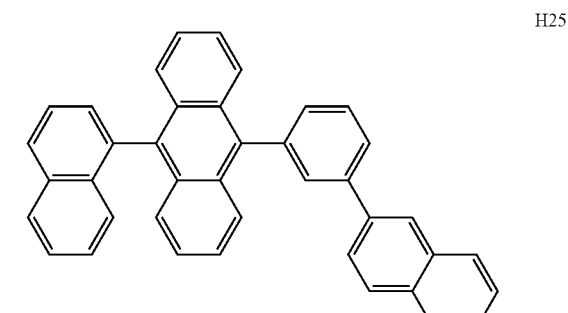
H26
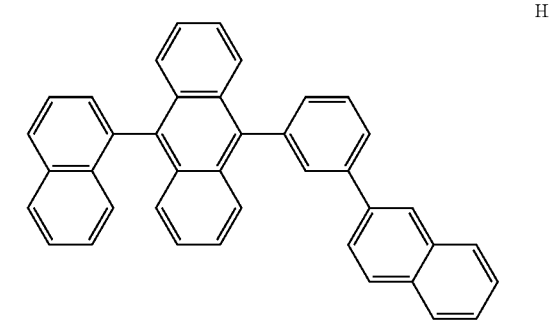
H27
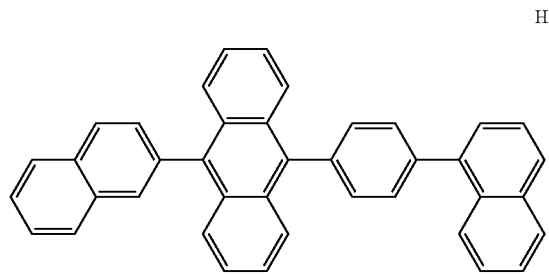

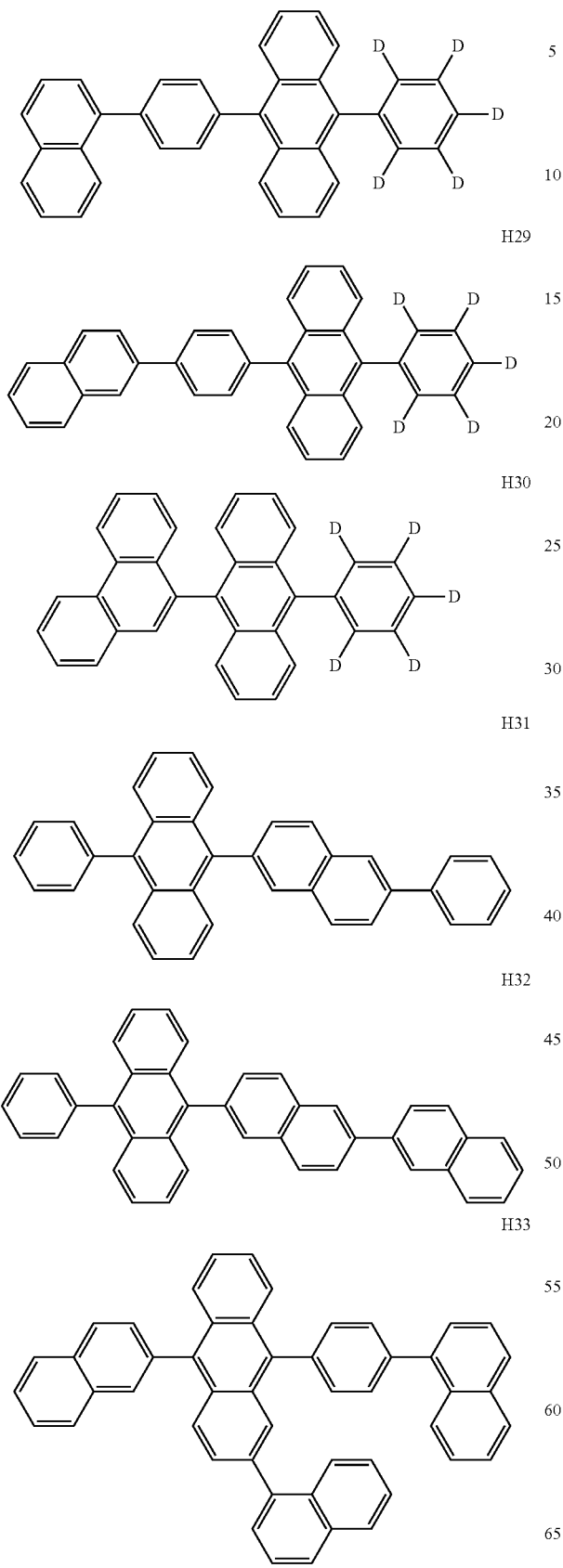

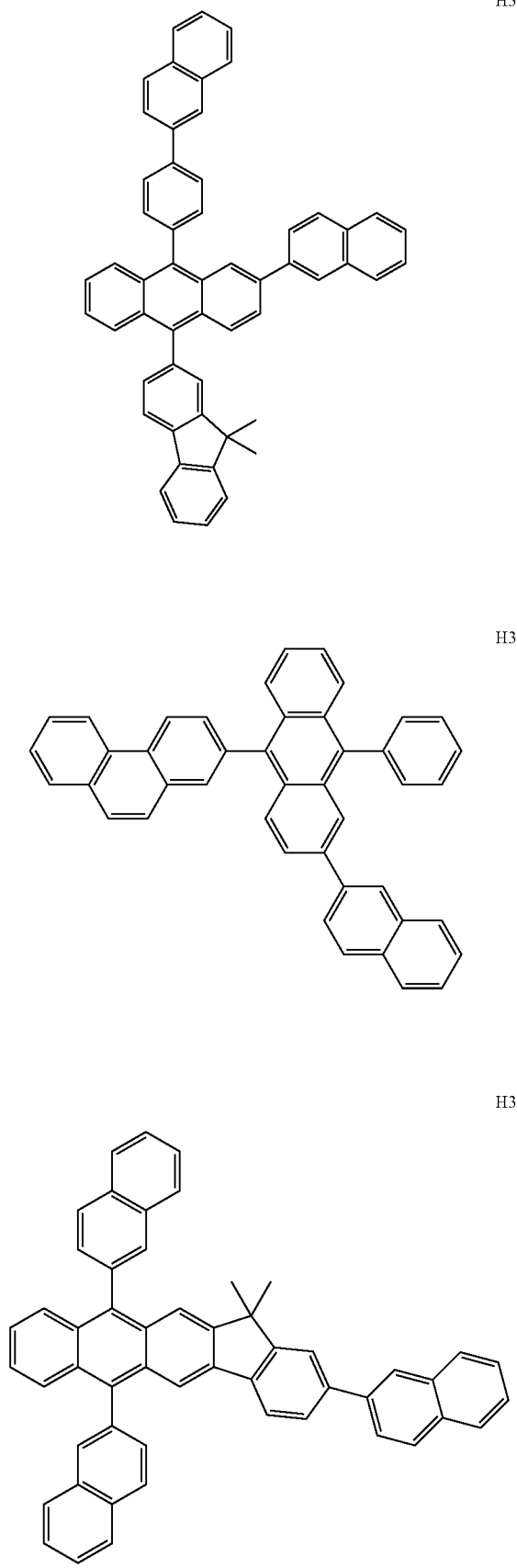

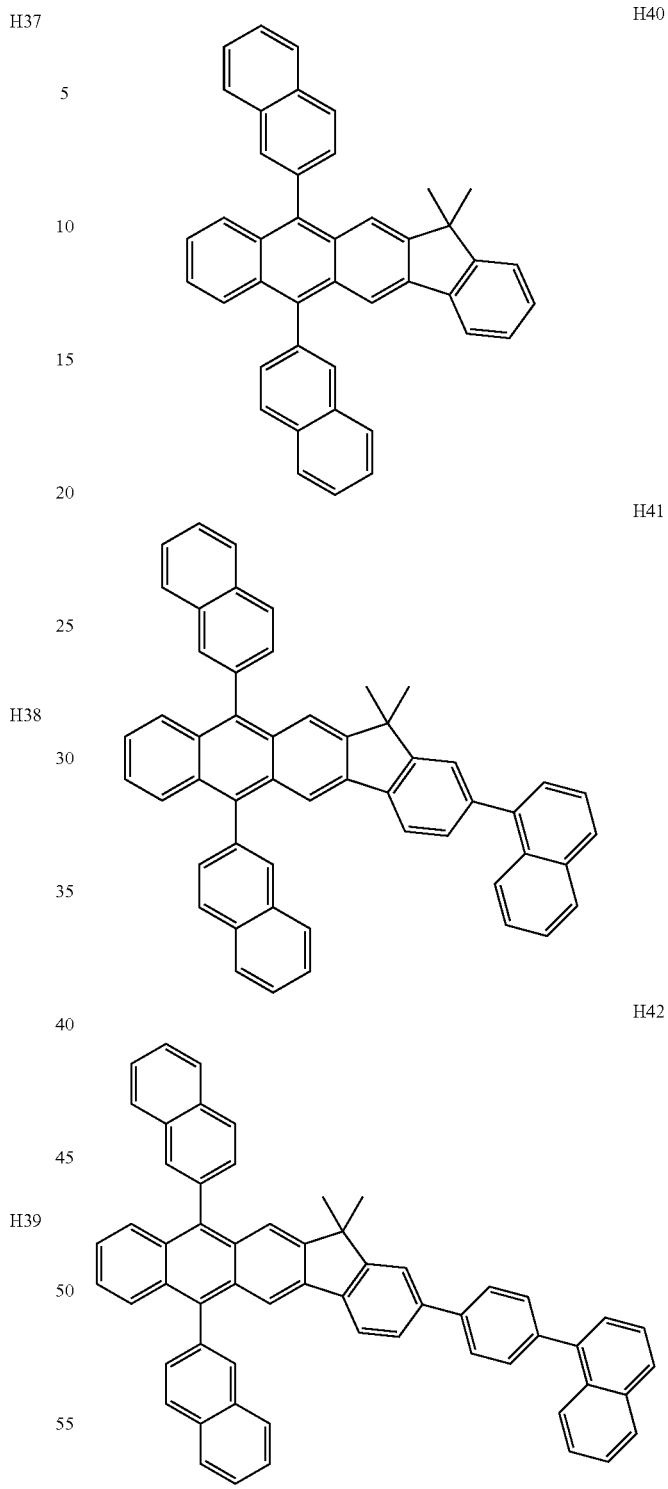

When the organic light-emitting device is a ful color organic light-emitting device, the emission layer may be patterned into a red emission layer, a green emission layer, and a blue emission layer. In some embodiments, the EML may have a stack structure including a red emission layer, a green emission layer, and/or a blue emission layer that are stacked upon one another to emit white light, but is not limited thereto.

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1,000 Å, and in some embodiments, may be from about 200 Å to about 600 Å. When the thickness of the EML is within these ranges, the EML may have improved light-emitting ability without a substantial increase in driving voltage.

Next, the electron transport region may be formed on the EML.

The electron transport region may include at least one of a HBL, an ETL, and an EIL.

In some embodiments, the electron transport region may have a structure including a HBL/ETL/EIL, or an ETL/EIL, wherein the layers forming the structure of the electron transport region may be sequentially stacked on the EML in the stated order. However, embodiments of the present disclosure are not limited thereto. The ETL may have a single-layer structure or a multi-layer structure including at least two different materials.

Conditions for forming the HBL, ETL, and EIL of the electron transport region may be the same as those for the HIL described above.

When the electron transport region includes a HBL, the HBL may include at least one of BCP, Bphen, and Balq. However, embodiments of the present disclosure are not limited thereto.

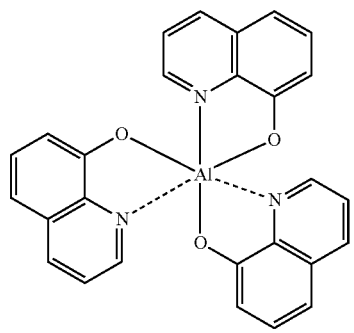

Alq$_3$

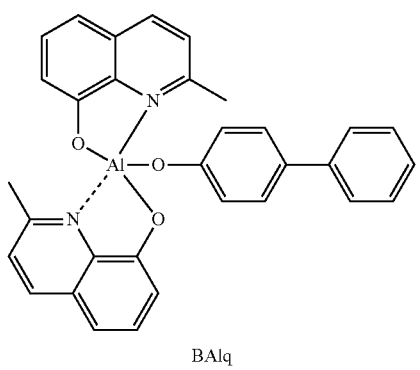

BAlq

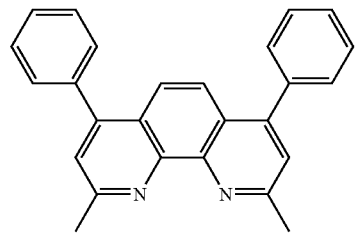

BCP

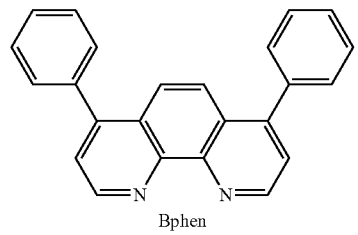

Bphen

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The ETL may further include at least one of Alq$_3$, Balq, TAZ, and NTAZ, in addition to BCP and Bphen described above.

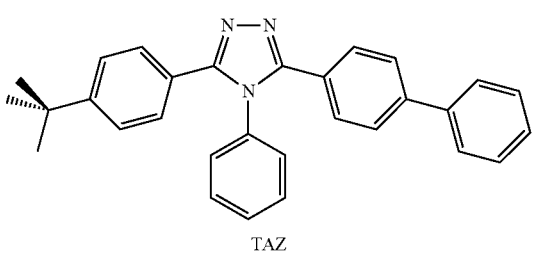

TAZ

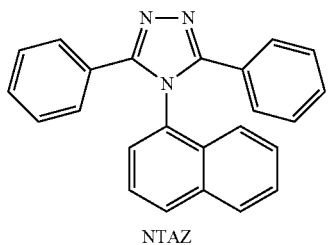

NTAZ

In some embodiments, the ETL may include at least one of Compounds ET1 and ET2, but is not limited thereto.

ET1

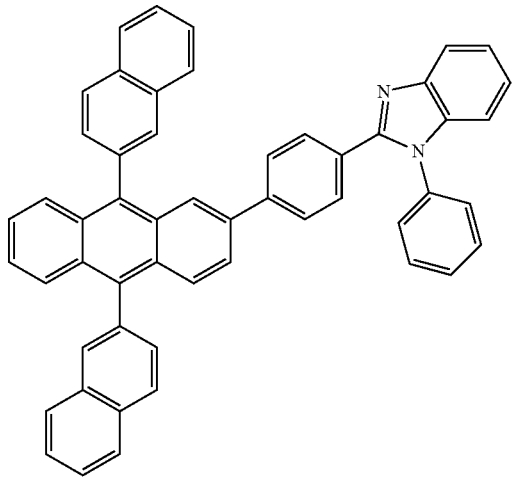

ET2

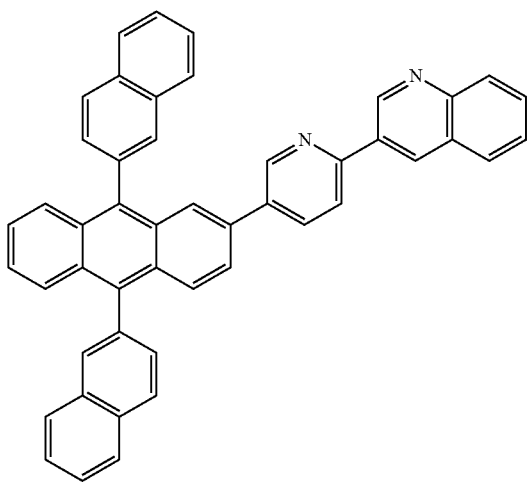

The thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials, The metal-containing material may include a lithium (Li) complex. Non-limiting examples of the Li complex are compound ET-D1 (lithium quinolate (LiQ)), or compound ET-D2.

ET-D1

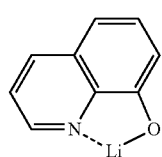

ET-D2

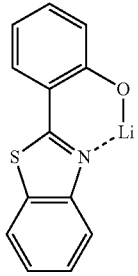

The electron transport region may include an EIL that may facilitate injection of electrons from the second electrode 19, The EIL may include at least one selected from LiF, NaCl, CsF, $Li_2O$, and BaO. The thickness of the EIL may be from about 1 Å to about 100 Å, and in some embodiments, from about 3 Å to about 90 Å. While not wishing to be bound by a theory, it is understood that when the thickness of the EIL is within these ranges, the EIL may have satisfactory electron injection ability without a substantial increase in driving voltage.

The second electrode 19 is disposed on the organic layer 15. The second electrode 19 may be a cathode. A material for the second electrode 19 may be a metal, an alloy, or an electrically conductive compound that has a low work function, or a combination thereof. Non-limiting examples of the material for the second electrode 19 are lithium (Li), magnesium (Mg), aluminum (Al), aluminum (Al)-lithium (Li), calcium (Ca), magnesium (Mg)-indium (In), magnesium (Mg)-silver (Ag), or the like. In some embodiments, to manufacture a top-emission light-emitting device, the second electrode 19 may be formed as a transmissive electrode from, for example, indium tin oxide (ITO) or indium zinc oxide (IZO).

Although the organic light-emitting device 10 of FIG. 1 is described above, embodiments of the present disclosure are not limited thereto, As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group are a methyl group, an ethyl group, a propyl group, an isobutyl group, a sec-butyl group, a tert-butyl group, a pentyl group, an iso-amyl group, and a hexyl group, A $C_1$-$C_{60}$ alkylene group as used herein refers to a divalent group having the same structure as the $C_1$-$C_{60}$ alkyl group.

As used herein, a $C_1$-$C_{60}$ alkoxy group refers to a monovalent group represented by —$OA_{101}$ (where $A_{101}$ is a $C_1$-$C_{60}$ alkyl group, as described above). Non-limiting examples of the $C_1$-$C_{60}$ alkoxy group are a methoxy group, an ethoxy group, and an isopropyloxy group.

As used herein, a $C_2$-$C_{60}$ alkenyl group has a structure including at least one carbon double bond in the middle or terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkylene group as used herein refers to a divalent group having the same structure as the $C_2$-$C_{60}$ alkenyl group.

As used herein, a $C_2$-$C_{60}$ alkynyl group has a structure including at least one carbon triple bond in the middle or terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group as used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

As used herein, a $C_1$-$C_{10}$ heterocycloalkyl group refers to a monovalent monocyclic group having 1 to 10 carbon atoms in which at least one hetero atom selected from N, O, P, and S is included as a ring-forming atom. Non-limiting examples of the $C_1$-$C_{10}$ heterocycloalkyl group are a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group, As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group, A $C_3$-$C_{10}$ cycloalkenylene group as used herein refers to a divalent group having the same structure as the $C_3$-$C_{10}$ cycloalkenyl group.

As used herein, a $C_1$-$C_{10}$ heterocycloalkenyl group refers to a monovalent monocyclic group having 1 to 10 carbon atoms that includes at least one double bond in the ring and in which at least one hetero atom selected from N, O, P, and S is included as a ring-forming atom. Non-limiting examples of the $C_1$-$C_{10}$ heterocycloalkenyl group are a 2,3-dihydrofuranyl group and a 2,3-dihydrothiophenyl group. A $C_1$-$C_{10}$ heterocycloalkenyiene group as used herein refers to a divalent group having the same structure as the $C_1$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group, and the $C_6$-$C_{60}$ arylene group include at least two rings, the rings may be fused to each other.

As used herein, a $C_1$-$C_{60}$ heteroaryl group refers to a monovalent, aromatic carbocyclic aromatic group having 1 to 60 carbon atoms in which at least one hetero atom selected from N, O, P, and S is included as a ring-forming atom, and 2 to 60 carbon atoms. A $C_1$-$C_{60}$ heteroarylene group as used herein refers to a divalent, aromatic carbocyclic group having 1 to 60 carbon atoms in which at least one hetero atom selected from N, O, P, and S is included as a ring-forming atom. Non-limiting examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl and the $C_1$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group, as described above), and a $C_6$-$C_{60}$ arylthio group indicates —$SA_{103}$ (where $A_{103}$ is a $C_6$-$C_{60}$ aryl group, as described above).

As used herein, the monovalent non-aromatic condensed polycyclic group refers to a monovalent group (including, for example, 8 to 60 carbon atoms) that includes at least two rings condensed to each other and includes only carbon atoms as ring-forming atoms and does not have aromaticity as a whole. An example of the monovalent non-aromatic condensed polycyclic group is a fluorenyl group. As used herein, a divalent non-aromatic condensed polycyclic group refers to a divalent group with the same structure as the monovalent non-aromatic condensed polycyclic group.

As used herein, the monovalent non-aromatic condensed heteropolycyclic group refers to a monovalent group (including, for example, 2 to 60 carbon atoms) that includes at least two rings condensed to each other and include carbons and hetero atoms selected from N, O, P and S as ring-forming atoms and that does not have aromaticity as a whole. An example of the monovalent non-aromatic condensed heteropolycyclic group is a carbazolyl group. As used herein, a divalent non-aromatic condensed heteropolycyclic group refers to a divalent group with the same structure as the monovalent non-aromatic condensed polycyclic group.

As used herein, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —CD$_3$, —CD$_2$H, —CDH$_2$, —CF$_3$, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, and —C(=O)(Q$_{11}$), —Si(Q$_{11}$)(Q$_{12}$)(Q$_{13}$), and —N(Q$_{11}$)(Q$_{12}$), wherein Q$_{11}$ to Q$_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{13}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

When a group containing a specified number of carbon atoms is substituted with any of the substituents listed above, the number of carbon atoms in the resulting "substituted" group may be the number of atoms contained in the original (base) group plus the number of carbon atoms (if any) contained in the substituent. For example, the "substituted $C_1$-$C_{30}$ alkyl" may refer to a $C_1$-$C_{30}$ alkyl group substituted with $C_{6-60}$ aryl group, in which the total number of carbon atoms may be $C_7$-$C_{90}$.

One or more embodiments of the present disclosure will now be described in detail with reference to the following synthesis examples and other examples of compounds and organic light-emitting devices. However, these examples are for illustrative purposes only and are not intended to limit the scope of the present disclosure. In the following synthesis examples, the expression that "'B', instead of 'A', was used" means that the amounts of 'B' and 'A' were the same in equivalent amounts.

EXAMPLES

Synthesis Example 1

Synthesis of Compound 1

Compound 1 was synthesized according to Reaction Scheme 1.

Reaction Scheme 1

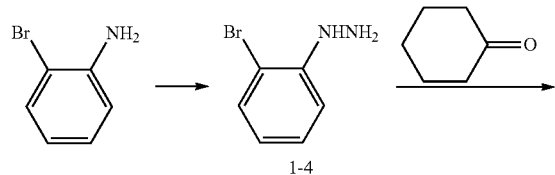

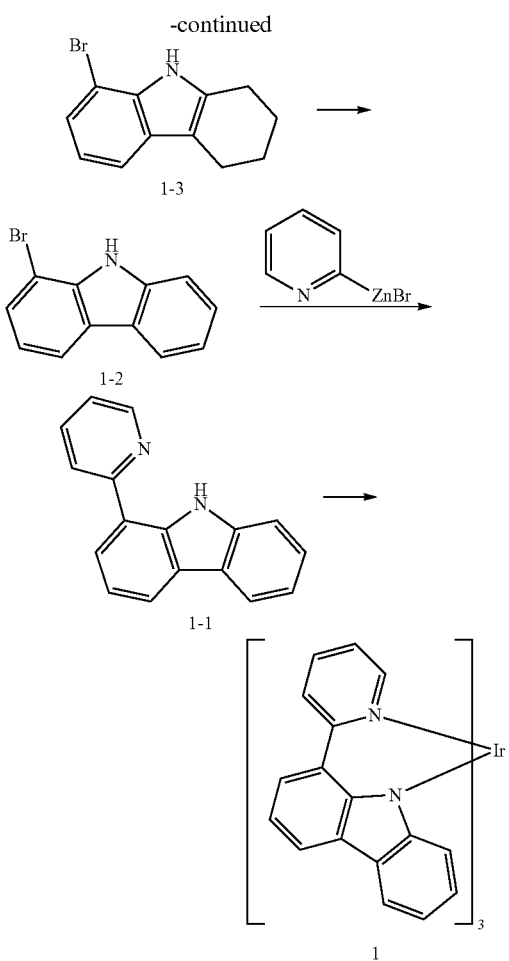

1) Synthesis of Intermediate 1-4

After 20.0 grams (g) (116 millimoles (mmol)) of 2-bromoaniline was dissolved in 100 milliliters (mL) of a 20% aqueous HCl solution, 15 mL (128 mmol) of an aqueous sodium nitrate solution was slowly added thereto at about 0° C. The reaction mixture was stirred for about 1 hour, followed by addition of a solution of 60 mL (116 mmol) of stannous chloride dihydrate dissolved in a 35% aqueous HCl solution. The reaction mixture was stirred at room temperature for about 2 hours. After completion of the reaction, a solid was filtered from the resulting reaction mixture, washed twice with a 35% aqueous HCl solution, and dried under reduced pressure, thereby obtaining about 16 g (85,8 mmol, Yield: 74%) of Intermediate 1-4 without performing a purification process. This compound was identified by liquid chromatography-mass spectrometry (LC-MS).

LC-MS m/z=186.98 (M+H)$^+$

2) Synthesis of Intermediate 16 g (85.8 mmol) of Intermediate 1-4 and 8.4 g (85.8 mmol) of cyclohexanone were dissolved in 100 mL of acetic acid, and the reaction mixture was heated at about 130° C. under reflux for about 12 hours. After completion of the reaction, the solvent was removed to obtain a solid product, which was extracted with ethylacetate. The combined organic extracts were dried with magnesium sulfate to remove moisture, and the product was separated and purified by column chromatography to obtain about 13.1 g (52.3 mmol, Yield: 61%) of Intermediate 1-3. This compound was identified by LC-MS.

LC-MS m/z=250.02 (M+H)$^+$

3) Synthesis of Intermediate 1-2

13.1 g (52.3 mmol) of Intermediate 1-3 and 15.4 g (62.76 mmol) of p-chloranil were dissolved in 500 mL of o-xylene, and the resulting mixture was heated at about 130° C. under reflux for about 8 hours. After completion of the reaction, the reaction product was cooled down to room temperature, and a solid was filtered from the resulting reaction mixture and washed twice with distilled water. The resulting solid product was separated and purified by column chromatography to obtain about 8.9 g (36.1 mmol, Yield: 69%) of Intermediate 1-2, This compound was identified by LC-MS.

LC-MS m/z=245.98 (M+H)$^+$

4) Synthesis of Intermediate 1-1

8.9 g (36 mmol) of Intermediate 1-2 and 1.45 g (35 mmol) of 60% sodium hydride (dispersion in mineral oil) were dissolved in 400 mL of tetrahydrofuran and stirred, first at about −78° C. for about 10 minutes, and then at room temperature for about 2 hours. 20 mL (1.76 mmol) of tetrakis(triphenylphosphine)palladium(0) dissolved in tetrahydrofuran, and 79 mL (39.5 mmol) of 0.5 molar (M)_solution of 2-pyridylzinc bromide were subsequently added to the resulting solution and the resulting mixture was heated at about 80° C. under reflux for about 16 hours, After completion of the reaction, the reaction mixture was cooled down to room temperature, and a saturated sodium hydrogen carbonate solution was added thereto, followed by extraction with dichloromethane to obtain an organic phase, which was dried with magnesium sulfate, and distilled under reduced pressure. The resulting product was separated and purified by column chromatography to obtain about 6.4 g (13.1 mmol, Yield: 73%) of Intermediate 1-1. This compound was identified by LC-MS.

LC-MS m/z=245.10 (M+H)$^+$

5) Synthesis of Compound 1

After 2.0 g (8.2 mmol) of Intermediate 1-1 was dissolved in 50 mL of tetrahydrofuran at room temperature, 15 mL (80 mmol) of a dispersion of sodium hydride in tetrahydrofuran was added to the solution, and the resulting mixture was stirred at about 65° C. for about 10 hours, After the resulting green solution was filtered to remove floating matter, 10 mL (2.5 mmol) of iridium(III) acetylacetonate dissolved in tetrahydrofuran was added thereto, and the resulting mixture was heated at about 70° C. under reflux for about 4 hours, followed by distillation under reduced pressure to remove the solvent. The resulting solid product was dissolved in 50 mL of glycerol and heated at about 230° C. under reflux for about 30 hours. After completion of the reaction, the reaction mixture was cooled down to room temperature, and a solid was filtered from the resulting reaction mixture and washed with a small amount of ethanol. The product was separated and purified by column chromatography to obtain about 0.98 g (1.06 mmol, Yield: 13%) of Compound 1. This compound was identified by LC-MS.

LC-MS m/z=923.24 (M+H)$^+$

Synthesis Example 2

Synthesis of Compound 2

Compound 2 was synthesized according to Reaction Scheme 2.

Reaction Scheme 2

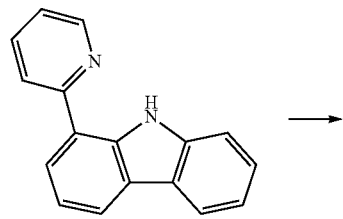

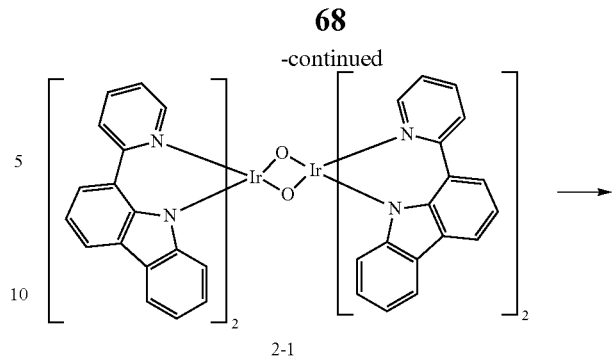

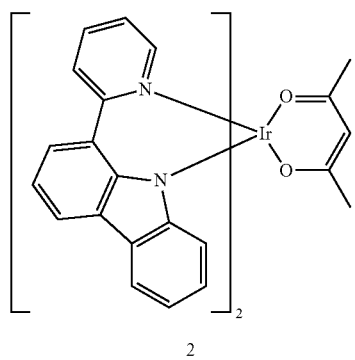

1) Synthesis of Intermediate 2-1

After 2.0 g (8.2 mmol) of Intermediate 1-1 was dissolved in 50 mL of tetrahydrofuran, 15 mL (80 mmol) of a dispersion of sodium hydride in tetrahydrofuran was added to the solution and stirred at about 65° C. for about 10 hours. After the resulting green solution was filtered to remove floating matter, 10 mL (3.7 mmol) of tris(tetrahydrothiophene) iridium(III) chloride dissolved in tetrahydrofuran was added to the resulting solution and heated at about 70° C. under reflux for about 3 hours, followed by distillation under reduced pressure to remove the solvent. The resulting solid product was dissolved in 50 mL of 2-ethoxyethanol and subsequently heated at about 130° C. under reflux for about 16 hours. After completion of the reaction, the reaction mixture was cooled down to room temperature, and a solid was filtered therefrom and washed with a small amount of ethanol, thereby to obtain 3.8 g (2.73 mmol, Yield: 67%) of Intermediate 2-1. This compound was subjected to further reaction without structural identification.

2) Synthesis of Compound 2

After 3.8 g (2.73 mmol) of Intermediate 2-1 and 3.8 g (27.5 mmol) of potassium carbonate were dissolved in 50 mL of 2-ethoxyethanol at room temperature, 0.84 mL (8.2 mmol) of acetylacetone was added to the solution and heated at about 120° C. under reflux for about 20 hours. After completion of the reaction, the reaction mixture was distilled under reduced pressure to remove the solvent, and the resulting solid product was separated and purified by column chromatography to obtain about 0.93 g (1.20 mmol, Yield: 22%) of Compound 2. This compound was identified by LC-MS.

LC-MS m/z=779.19 (M+H)$^+$

Synthesis Example 3

Synthesis of Compound 3

Compound 3 was synthesized according to Reaction Scheme 3.

Reaction Scheme 3

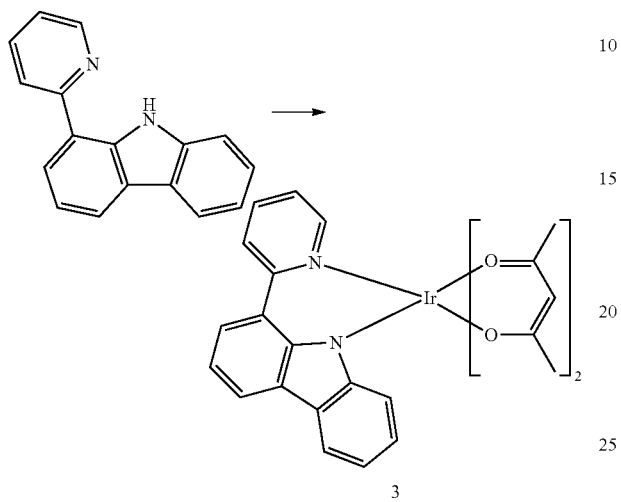

3

1) Synthesis of Compound 3

After 2.0 g (8.2 mmol) of Intermediate 1-1 was dissolved in 50 mL of tetrahydrofuran at room temperature, 15 mL (80 mmol) of a dispersion of sodium hydride in tetrahydrofuran was added to the solution and stirred at about 65° C. for about 10 hours. After the resulting green solution was filtered to remove floating matter, 10 mL (8.2 mmol) of iridium(III) acetylacetonate dissolved in tetrahydrofuran was added thereto, the and the resulting mixture was heated at about 70° C. under reflux for about 4 hours, followed by distillation under reduced pressure to remove the solvent. The resulting solid product was dissolved in 50 mL of glycerol and subsequently heated at about 210° C. under reflux for about 12 hours. After completion of the reaction, the reaction mixture was cooled down to room temperature, and a solid was filtered therefrom and washed with a small amount of ethanol, followed by separation and purification by column chromatography to obtain about 1.92 g (3.03 mmol, Yield: 37%) of Compound 3. This compound was identified by LC-MS.

LC-MS m/z=635.14 (M+H)$^+$

Synthesis Example 4

Synthesis of Compound 4

Compound 4 was synthesized according to Reaction Scheme 4.

Reaction Scheme 4

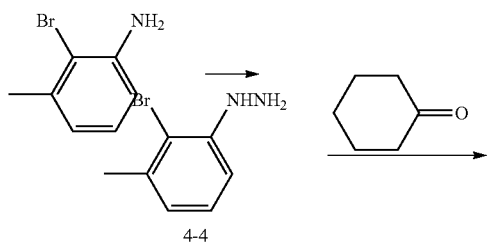

4-4

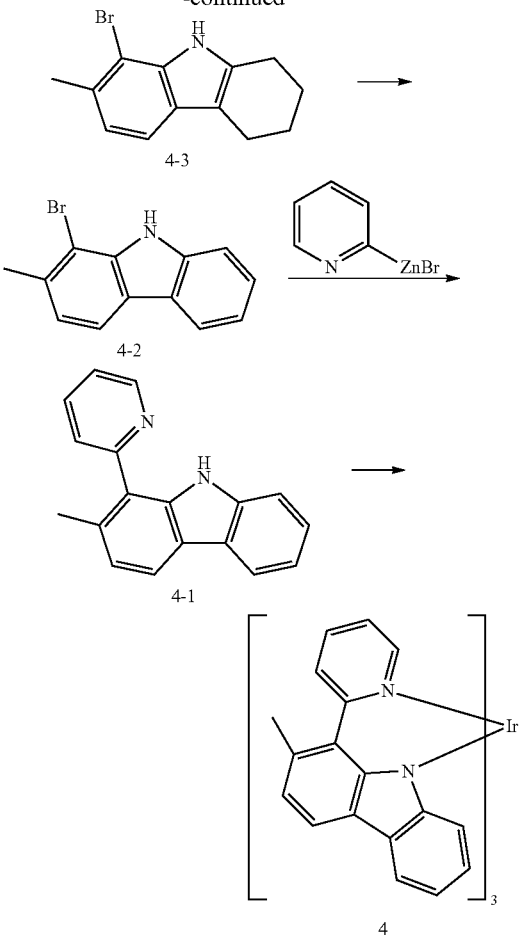

4

1) Synthesis of Intermediate 4-4

Intermediate 4-4 (Yield: 7 was synthesized in the same manner as Intermediate 1-4 in Synthesis Example 1 except that 2-bromo-3-methylaniline, instead of 2-bromoaniline, was used. This compound was identified by LC-MS.

LC-MS m/z=200.99 (M+H)$^+$

2) Synthesis of Intermediate 4-3

Intermediate 4-3 (Yield: 65%) was synthesized in the same manner as Intermediate 1-3 in Synthesis Example 1, except that Intermediate 4-4, instead of Intermediate 1-4, was used. This compound was identified by LC-MS.

LC-MS m/z=264.03 (M+-H)$^+$

3) Synthesis of Intermediate 4-2

Intermediate 4-2 (Yield: 70%) was synthesized in the same manner as Intermediate 1-2 in Synthesis Example 1, except that Intermediate 4-3, instead of Intermediate 1-3, was used. This compound was identified by LC-MS.

LC-MS m/z=260.00 (M+H)$^+$

4) Synthesis of Intermediate 4-1

Intermediate 4-1 (Yield: 68%) was synthesized in the same manner as Intermediate 1-1 in Synthesis Example 1, except that Intermediate 4-2, instead of Intermediate 1-2, was used. This compound was identified by LC-MS.

LC-MS m/z=259.12 (M+H)$^+$

5) Synthesis of Compound 4

2.0 g (7.75 mmol) of Intermediate 4-1 and 1.15 g (2.35 mmol) of iridium(III) acetylacetonate were dissolved in 50 mL of glycerol at room temperature and subsequently heated at about 250° C. under reflux for about 32 hours. After completion of the reaction, the reaction mixture was cooled down to room temperature, and a solid was filtered from the resulting reaction mixture and washed with a small amount of ethanol, followed by separation and purification by column chromatography to obtain about 0.25 g (0.26 mmol, Yield: 11) of Compound 4. This compound was identified by LC-MS.

LC-MS m/z=965.29(M+H)$^+$

Synthesis Example 5

Synthesis of Compound 5

Compound 5 was synthesized according to Reaction Scheme 5.

Reaction Scheme 5

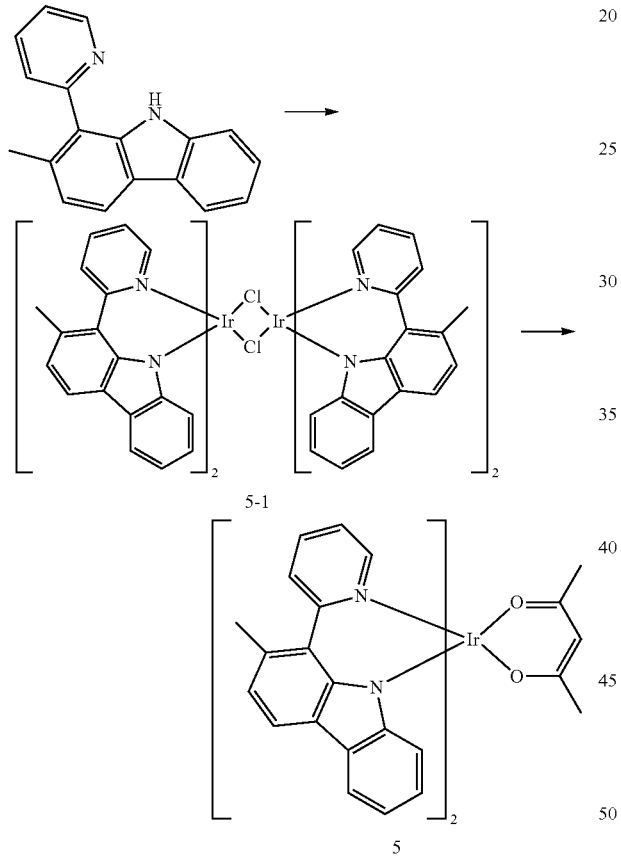

1) Synthesis of Intermediate 5-1

2.0 g (7.75 mmol) of Intermediate 4-1 and 1.21 g (3.43 mmol) of iridium(III) chloride hydrate were dissolved in 30 mL of 2-ethoxyethanol and subsequently heated at about 130° C. under reflux for about 12 hours. After completion of the reaction, the reaction product was cooled down to room temperature, and a solid was filtered from the resulting reaction mixture and washed with a small amount of ethanol, thereby obtaining 2.07 g (1.39 mmol, Yield: 81%) of Intermediate 5-1. This compound was subjected to further reaction without structural identification.

2) Synthesis of Compound 5

Compound 5 (Yield: 17%) was synthesized in the same manner as Compound 2 in Synthesis Example 2, except that Intermediate 5-1, instead of Intermediate 2-1, was used. This compound was identified by LC-MS.

LC-MS m/z=807.22 (M+H)$^+$

Synthesis Example 6

Synthesis of Compound 6

Compound 6 was synthesized according to Reaction Scheme 6.

Reaction Scheme 6

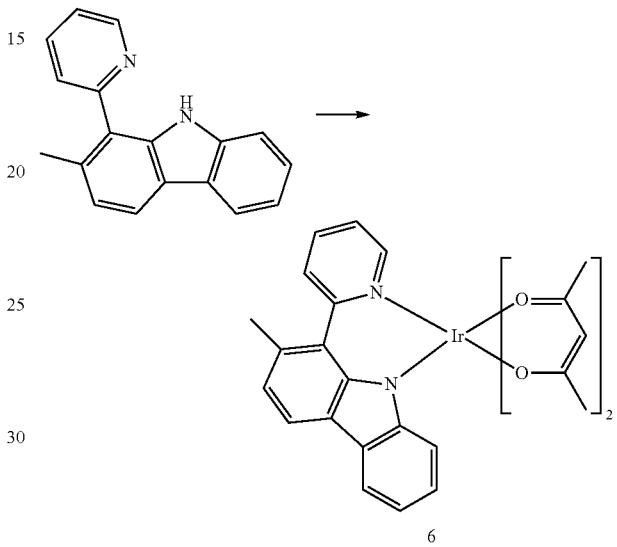

1) Synthesis of Compound 6

2.0 g (7.75 mmol) of Intermediate 4-1 and 3.8 g (7.75 mmol) of iridium(III) acetylacetonate were dissolved in 50 mL of glycerol at room temperature and then heated at about 220° C. under reflux for about 14 hours. After completion of the reaction, the reaction mixture was cooled down to room temperature, and a solid was filtered from the resulting reaction mixture and washed with a small amount of ethanol. The product was separated and purified by column chromatography to obtain about 1.76 g (2.71 mmol, Yield: 35%) of Compound 6. This compound was identified by LC-MS, LC-MS m/z=649.16 (M+H)$^+$ Synthesis Example 7

Synthesis of Compound 7

Compound 7 was synthesized according to Reaction Scheme 7.

Reaction Scheme 7

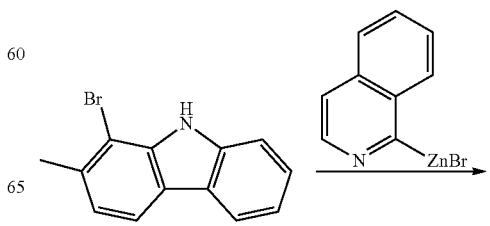

-continued

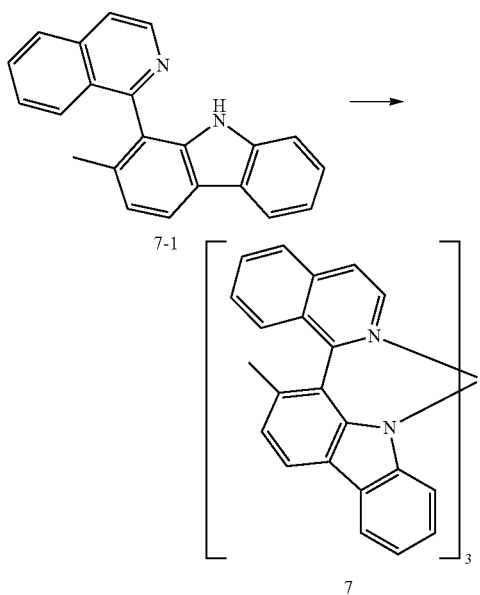

7-1

7

1) Synthesis of Intermediate 7-1

Intermediate 7-1 (Yield: 62%) was synthesized in the same manner as Intermediate 1-1 in Synthesis Example 1, except that Intermediate 4-2, instead of Intermediate 1-2, was used. This compound was identified by LC-MS.

LC-MS m/z=309.13 (M+H)$^+$

2) Synthesis of Compound 7

Compound 7 (Yield: 10%) was synthesized in the same manner as Compound 4 in Synthesis Example 4, except that Intermediate 7-1, instead of Intermediate 4-1, was used. This compound was identified by LC-MS.

LC-MS m/z=1115.33 (M+H)$^+$

Synthesis Example 8

Synthesis of Compound 8

Compound 8 was synthesized according to Reaction Scheme 8.

Reaction Scheme 8

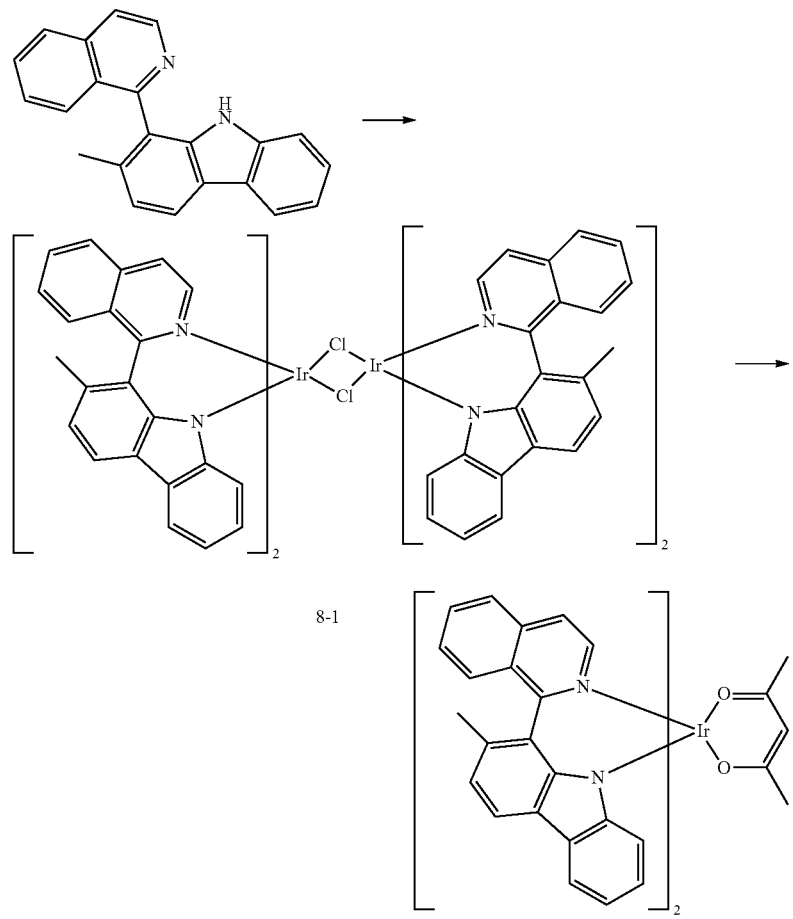

8-1

8

1) Synthesis of Intermediate 8-1

Intermediate 8-1 (Yield: 77%) was synthesized in the same manner as Intermediate 5-1 in Synthesis Example 5, except that Intermediate 7-1, instead of Intermediate 4-1, was used. This compound was subjected to further reaction without structural identification.

2) Synthesis of Compound 8

Compound 8 (Yield: 14%) was synthesized in the same manner as Compound 2 in Synthesis Example 2, except that Intermediate 8-1 instead of Intermediate 2-1, was used. This compound was identified by LC-MS.

LC-MS m/z=907.25 (M+H)$^+$

Synthesis Example 9

Synthesis of Compound 9

Compound 9 was synthesized according to Reaction Scheme 9.

Reaction Scheme 9

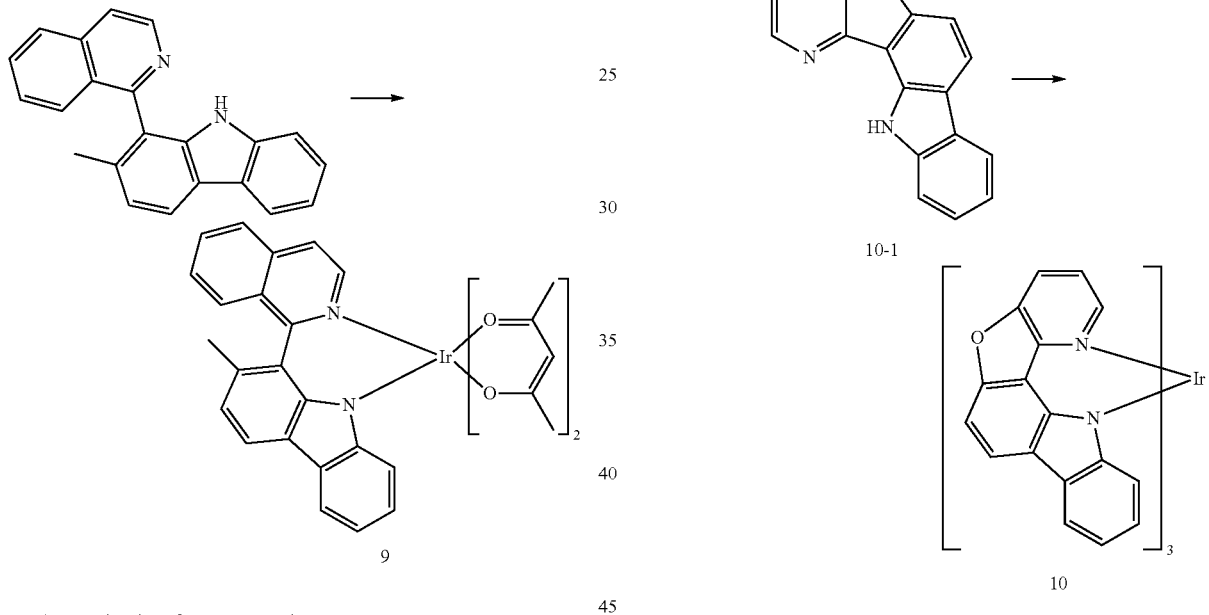

1) Synthesis of Compound 9

Compound 9 (Yield: 36%) was synthesized in the same manner as Compound 6 in Synthesis Example 6, except that Intermediate 7-1, instead of Intermediate 4-1, was used. This compound was identified by LC-MS.

LC-MS m/z=699.18 (M+H)$^+$

Synthesis Example 10

Synthesis of Compound 10

Compound 10 was synthesized according to Reaction Scheme 10.

Reaction Scheme 10

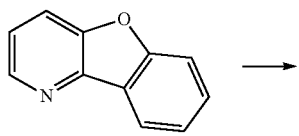

-continued

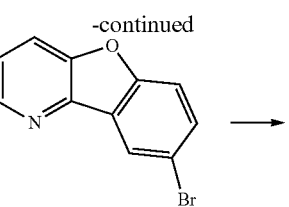

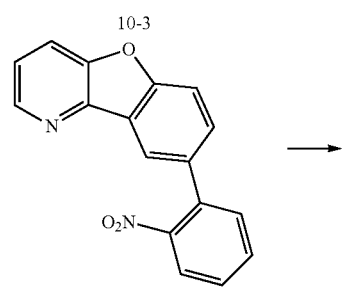

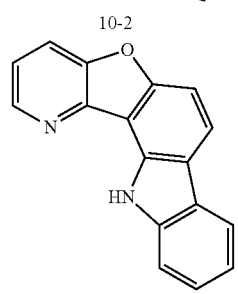

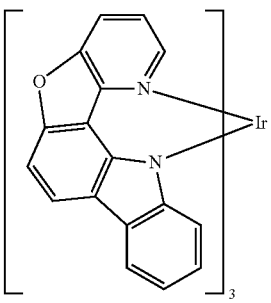

1) Synthesis of Intermediate 10-3

After 10 g (59.1 mmol) of benzofuro[3,2-b]pyridine was dissolved in 150 mL of acetic acid, 50 mL of sulfuric acid, 10.5 g (59.1 mmol) of N-bromosuccinimide was added thereto. The reaction mixture was stirred at room temperature for about 5 hours. After completion of the reaction, cold distilled water was added to the reaction mixture, followed by extraction with dichloromethane, drying with sodium sulfate, and distillation under reduced pressure. The resulting solid product was recrystallized with ethanol, thereby obtaining about 11.3 g (45.5 mmol, Yield: 77%) of Intermediate 10-3. This compound was identified by LC-MS.

LC-MS m/z=247.96 (M+H)$^+$

2) Synthesis of Intermediate 10-2

After 11.3 g (45.5 mmol) of Intermediate 10-3 was dissolved in 100 mL of toluene, 15.2 g (91 mmol) of 2-nitrophenylboronic acid, 22.3 g (68.3 mmol) of cesium carbonate, and 1.6 g (4 mmol) of tetrakis(triphenylphosphine)palladium were added thereto. The reaction mixture was heated at about 110° C. under reflux for about 15 hours, After completion of the reaction, the reaction mixture was filtered through diatomite to obtain an organic phase. The organic phase was washed with distilled water and dried with sodium sulfate, followed by distillation under reduced pressure to remove the solvent, The product was separated and purified by column chromatography, thereby obtaining about 9 g (31 mmol, Yield: 68%) of Intermediate 10-2. This compound was identified by LC-MS.

LC-MS m/z=291.07 (M+H)$^+$

3) Synthesis of Intermediate 10-1

9 g (31 mmol) of Intermediate 10-2 and 20.3 g (77.5 mmol) of triphenylphosphine were dissolved in 60 mL of o-dichlorobenzene and heated at about 180° C. under reflux for about 20 hours. After completion of the reaction, the resulting product was distilled under reduced pressure, followed by separation and purification by column chromatography, thereby obtaining about 7 g (27.1 mmol, Yield: 88%) of Intermediate 10-1. This compound was identified by LC-MS.

LC-MS m/z=259.08 (M+H)$^+$

4) Synthesis of Compound 10

Compound 10 (Yield: 7%) was synthesized in the same manner as Compound 4 in Synthesis Example 4, except that Intermediate 10-1, instead of Intermediate 4-1, was used. This compound was identified by LC-MS.

LC-MS m/z=965.18 (M+H)$^+$

Synthesis Example 11

Synthesis of Compound 11

Compound 11 was synthesized according to Reaction Scheme 11.

Reaction Scheme 11

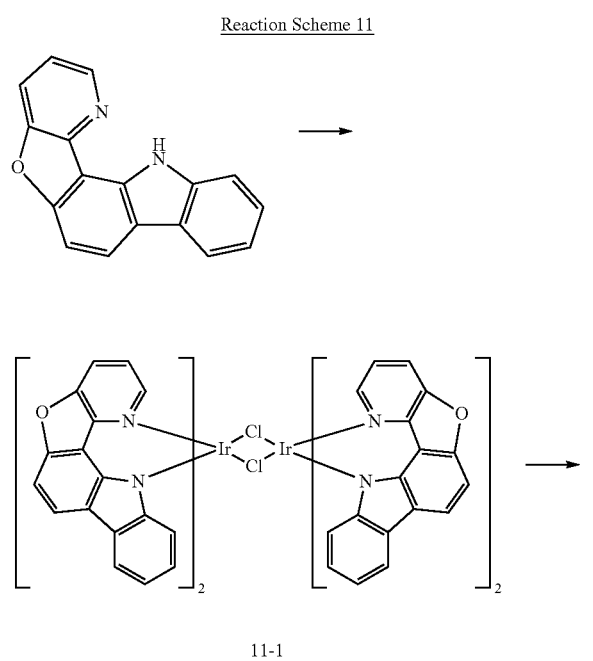

11-1

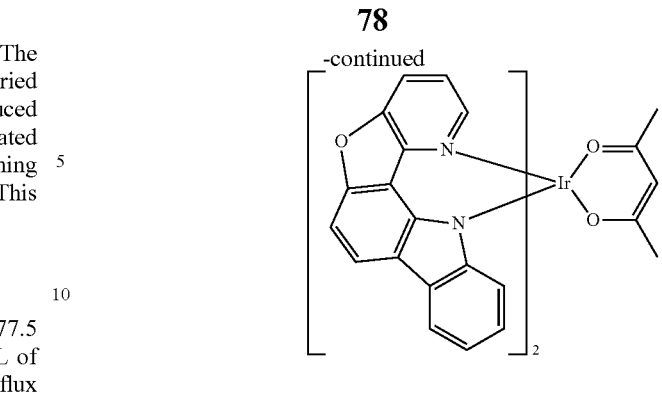

11

1) Synthesis of Intermediate 11-1

Intermediate 11-1 (Yield: 73%) was synthesized in the same manner as Intermediate 5-1 in Synthesis Example 5, except that Intermediate 10-1, instead of Intermediate 4-1, was used. This compound was subjected to further reaction without structural identification.

2) Synthesis of Compound 11

Compound 11 (Yield: 19%) was synthesized in the same manner as Compound 2 in Synthesis Example 2, except that Intermediate 11-1, instead of Intermediate 2-1, was used. This compound was identified by LC-MS.

LC-MS m/z=807.15 (M+H)$^+$

Synthesis Example 12

Synthesis of Compound 12

Compound 12 was synthesized according to Reaction Scheme 12.

Reaction Scheme 12

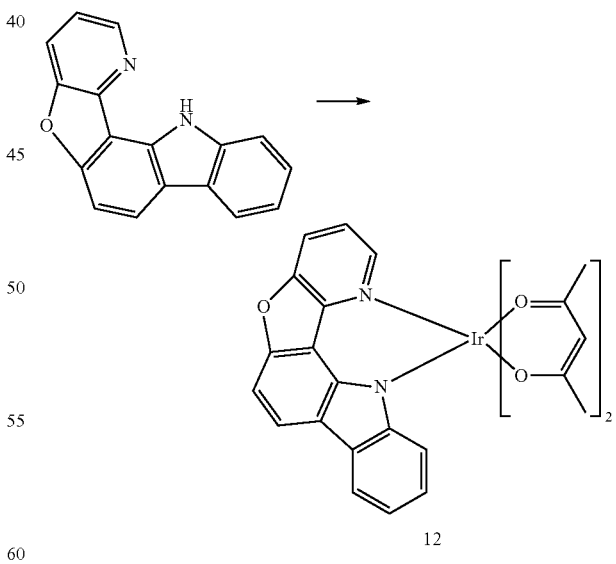

12

1) Synthesis of Compound 12

Compound 12 (Yield: 34%) was synthesized in the same manner as Compound 6 in Synthesis Example 6, except that Intermediate 10-1, instead of Intermediate 4-1, was used. This compound was identified by LC-MS.

LC-MS m/z=649.12 (M+H)$^+$

Synthesis Example 13

Synthesis of Compound 13

Compound 13 was synthesized according to Reaction Scheme 13.

Reaction Scheme 13

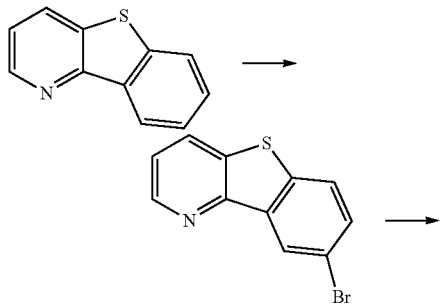

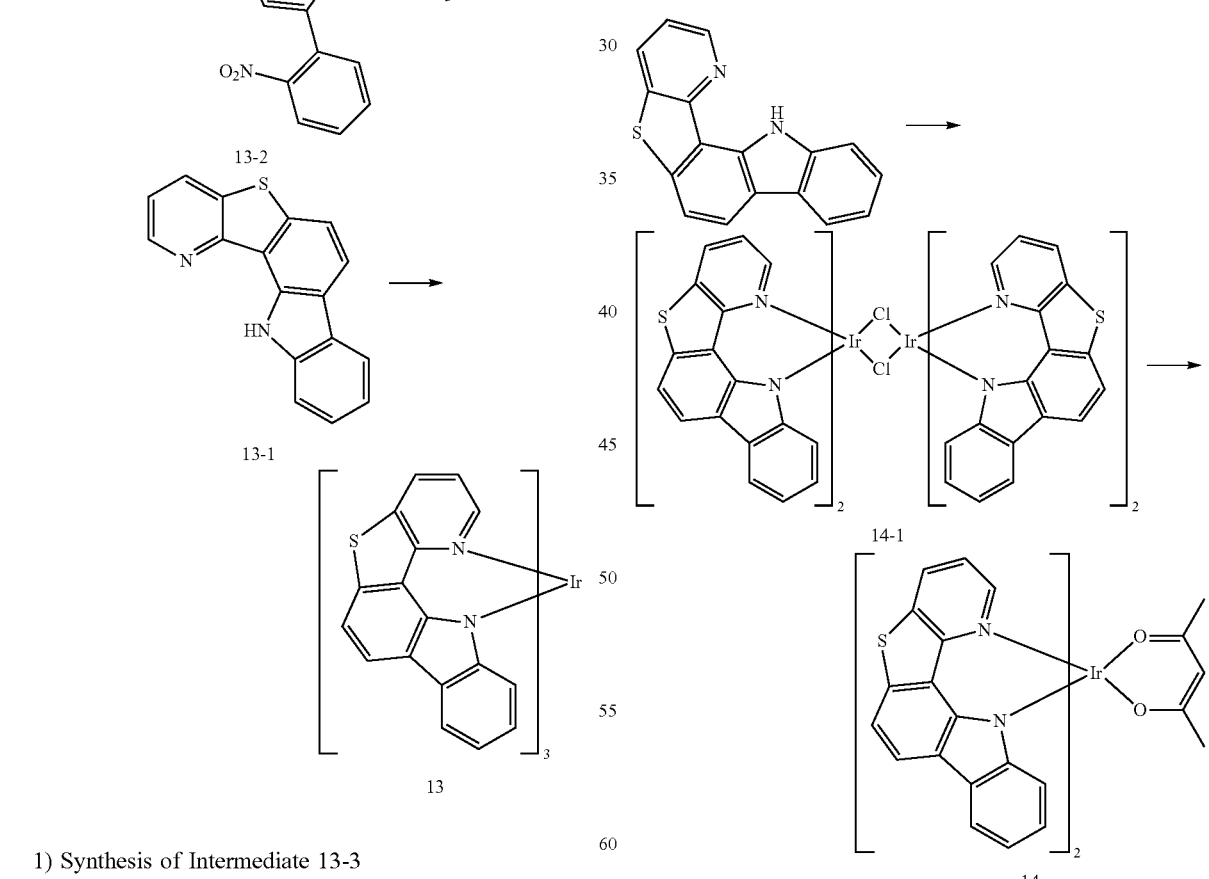

1) Synthesis of Intermediate 13-3

Intermediate 13-3 (Yield: 69%) was synthesized in the same manner as Intermediate 10-3 in Synthesis Example 10, except that benzo[4,5]thieno[2,3-b]pyridine, instead of benzofuro[3,2-b]pyridine, was used. This compound was identified by LC-MS.

LC-MS m/z=263.94 (M+H)$^+$

2) Synthesis of Intermediate 13-2

Intermediate 13-2 (Yield: 65%) was synthesized in the same manner as Intermediate 10-2 in Synthesis Example 10, except that Intermediate 13-3, instead of Intermediate 10-3, was used. This compound was identified by LC-MS.

LC-MS m/z=307.05 (M+H)$^+$

3) Synthesis of Intermediate 13-1

Intermediate 13-1 (Yield: 87%) was synthesized in the same manner as Intermediate 10-1 in Synthesis Example 10, except that Intermediate 13-2, instead of Intermediate 10-2, was used. This compound was identified by LC-MS.

LC-MS m/z=275.06 (M+H)

4) Synthesis of Compound 13

Compound 13 (Yield: 8%) was synthesized in the same manner as Compound 4 in Synthesis Example 4, except that Intermediate 13-1, instead of Intermediate 4-1, was used. This compound was identified by LC-MS.

LC-MS m/z=1013.11 (M+H)$^+$

Synthesis Example 14

Synthesis of Compound 14

Compound 14 was synthesized according to Reaction Scheme 14.

Reaction Scheme 14

1) Synthesis of Intermediate 14-1

Intermediate 14-1 (Yield: 69%) was synthesized in the same manner as Intermediate 5-1 in Synthesis Example 5, except that Intermediate 13-1, instead of Intermediate 4-1, was used. This compound was subjected to further reaction without structural identification.

2) Synthesis of Compound 14

Compound 14 (Yield: 20%) was synthesized in the same manner as Compound 2 in Synthesis Example 2, except that Intermediate 14-1, instead of Intermediate 2-1, was used. This compound was identified by LC-MS.

LC-MS m/z=839.10 (M+H)⁺

Synthesis Example 15

Synthesis of Compound 15

Compound 15 was synthesized according to Reaction Scheme 15.

Reaction Scheme 15

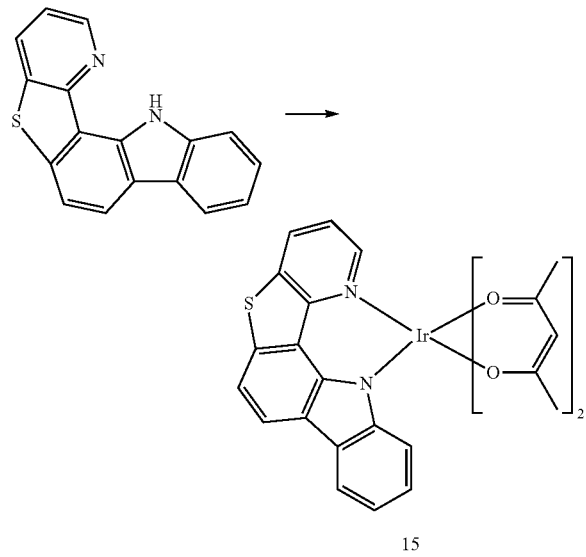

1) Synthesis of Compound 15

Compound 15 (Yield: 31%) was synthesized in the same manner as Compound 6 in Synthesis Example 6, except that Intermediate 13-1, instead of Intermediate 4-1, was used. This compound was identified by LC-MS.

LC-MS m/z=665.10 (M+H)⁺

Synthesis Example 16

Synthesis of Compound 25

Compound 25 was synthesized according to Reaction Scheme 25.

Reaction Scheme 25

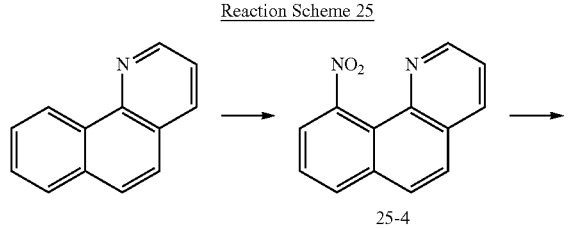

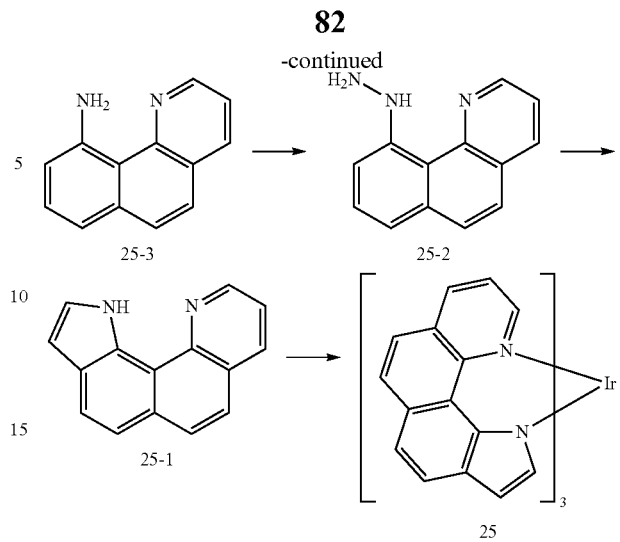

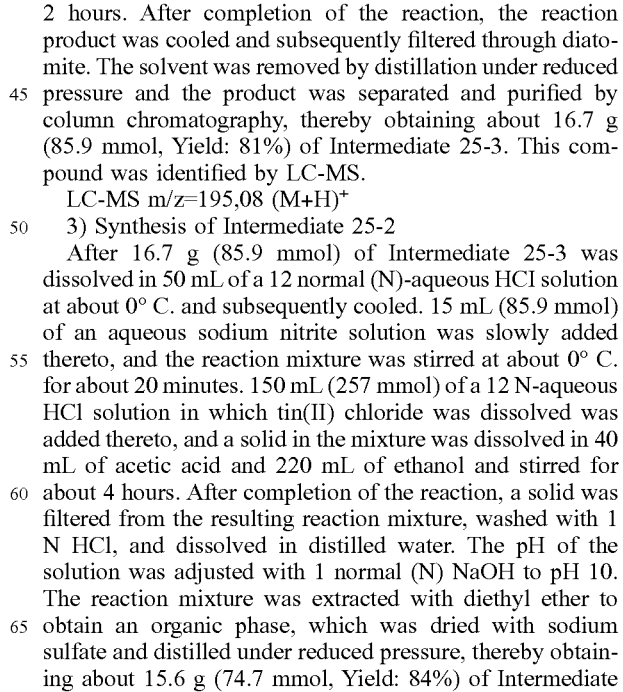

1) Synthesis of Intermediate 25-4

30 g (167 mmol) of 7,8-benzoquinoline, 0.38 g (1.67 mmol) of palladium(II) acetate, 0.52 g (3.35 mmol) of silver nitrite, and 90 g (334 mmol) of potassium persulfate were dissolved in 1 liter (L) of diethyl carbonate and stirred at about 130° C. for about 48 hours. After completion of the reaction, the resulting mixture was diluted with dichloromethane and filtered through diatomite to obtain an organic phase, which was dried under reduced pressure. The product was separated and purified by column chromatography, thereby to obtain about 23.9 g (106 mmol, Yield: 64%) of Intermediate 25-4. This compound was identified by LC-MS.

LC-MS m/z=225.06 (M+H)⁺

2) Synthesis of Intermediate 25-3

After 23.9 g (106 mmol) of Intermediate 25-4 was dissolved in 40 mL of acetic acid and 220 mL of ethanol, 41 g (747 mmol) of iron powder and 3.8 g (14 mmol) of iron(III) chloride hexahydrate were added thereto, and the reaction mixture was heated at about 100° C. under reflux for about 2 hours. After completion of the reaction, the reaction product was cooled and subsequently filtered through diatomite. The solvent was removed by distillation under reduced pressure and the product was separated and purified by column chromatography, thereby obtaining about 16.7 g (85.9 mmol, Yield: 81%) of Intermediate 25-3. This compound was identified by LC-MS.

LC-MS m/z=195,08 (M+H)⁺

3) Synthesis of Intermediate 25-2

After 16.7 g (85.9 mmol) of Intermediate 25-3 was dissolved in 50 mL of a 12 normal (N)-aqueous HCl solution at about 0° C. and subsequently cooled. 15 mL (85.9 mmol) of an aqueous sodium nitrite solution was slowly added thereto, and the reaction mixture was stirred at about 0° C. for about 20 minutes. 150 mL (257 mmol) of a 12 N-aqueous HCl solution in which tin(II) chloride was dissolved was added thereto, and a solid in the mixture was dissolved in 40 mL of acetic acid and 220 mL of ethanol and stirred for about 4 hours. After completion of the reaction, a solid was filtered from the resulting reaction mixture, washed with 1 N HCl, and dissolved in distilled water. The pH of the solution was adjusted with 1 normal (N) NaOH to pH 10. The reaction mixture was extracted with diethyl ether to obtain an organic phase, which was dried with sodium sulfate and distilled under reduced pressure, thereby obtaining about 15.6 g (74.7 mmol, Yield: 84%) of Intermediate 25-2. This compound was subjected to further reaction without structural identification, 4) Synthesis of Intermediate 25-1

15.6 g (74.7 mmol) of Intermediate 25-2, 2 g (14.9 mmol) of zinc chloride, and 5.2 g (24.9 mmol) of phosphorus pentachloride were mixed with 30 mL of pyruvic acid and stirred at about 170° C. under pressure for about 20 hours. After completion of the reaction, distilled water was added thereto, and the resulting reaction mixture was extracted with dichloromethane to obtain an organic phase. The organic phase was dried with sodium sulfate and distilled under reduced pressure. The product was separated and purified by column chromatography, thereby obtaining about 6.2 g (28.4 mmol, Yield: 38%) of Intermediate 25-1. This compound was identified by LC-MS.

LC-MS m/z=219.08 (M+H)$^+$

5) Synthesis of Compound 25

Compound 25 (Yield: 13%) was synthesized in the same manner as Compound 4 in Synthesis Example 4, except that Intermediate 25-1, instead of Intermediate 4-1, was used. This compound was identified by LC-MS.

LC-MS m/z=845.19 (M+H)$^+$

Synthesis Example 17

Synthesis of Compound 26

Compound 26 was synthesized according to Reaction Scheme 26.

Reaction Scheme 26

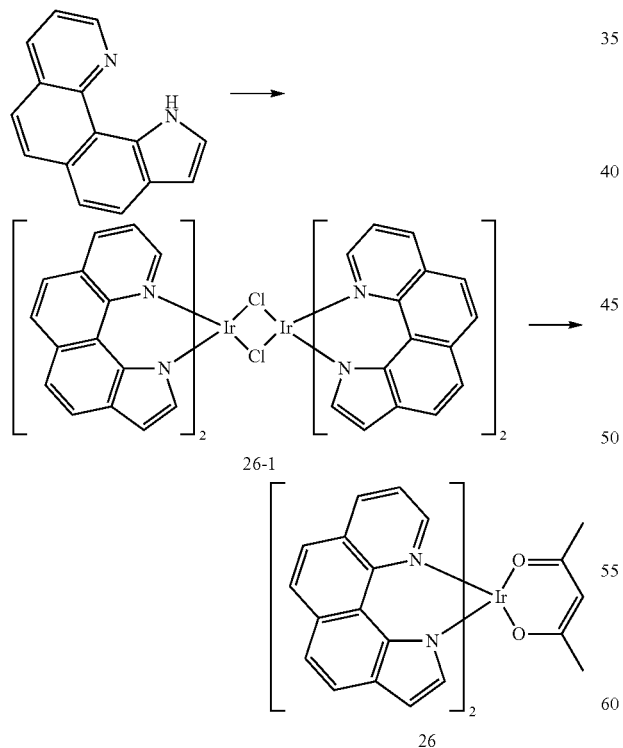

26

1) Synthesis of Intermediate 26-1

Intermediate 8-1 (Yield: 79%) was synthesized in the same manner as Intermediate 5-1 in Synthesis Example 5, except that Intermediate 26-1 instead of Intermediate 4-1, was used. This compound was subjected to further reaction without structural identification.

2) Synthesis of Compound 26

Compound 26 (Yield: 13%) was synthesized in the same manner as Compound 2 in Synthesis Example 2, except that Intermediate 26-1, instead of Intermediate 2-1, was used. This compound was identified by LC-MS.

LC-MS m/z=727.16 (M+H)$^+$

Synthesis Example 18

Synthesis of Compound 27

Compound 27 was synthesized according to Reaction Scheme 27.

Reaction Scheme 27

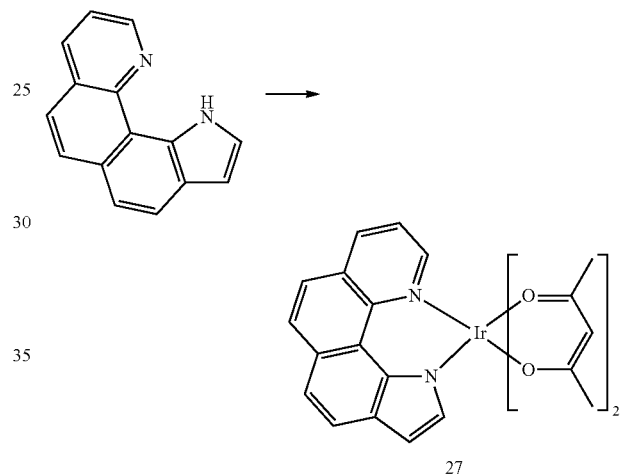

27

1) Synthesis of Compound 27

Compound 27 (Yield: 31%) was synthesized in the same manner as Compound 6 in Synthesis Example 6, except that Intermediate 25-1, instead of Intermediate 4-1, was used. This compound was identified by LC-MS.

LC-MS m/z=609.13 (M+H)$^+$

Synthesis Example 19

Synthesis of Compound 28

Compound 28 was synthesized according to Reaction Scheme 28.

Reaction Scheme 28

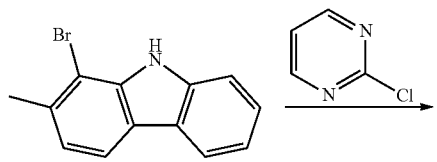

-continued

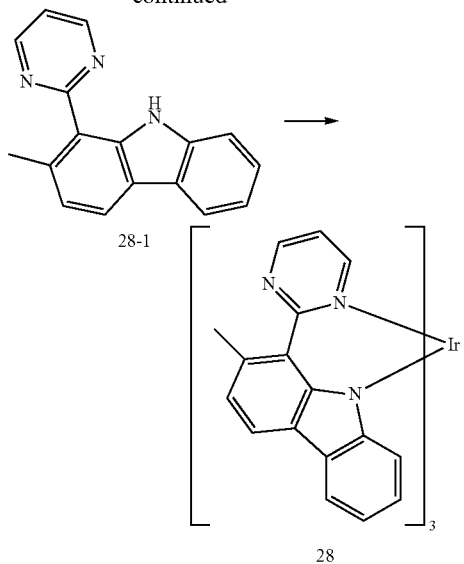

28-1

28

1) Synthesis of Intermediate 28-1

After 0.88 g (4 mmol) of cobalt(II) bromide and 5.2 g (80 mmol) of zinc powder were dissolved in 50 mL of acetonitrile, 1 mL (12 mmol) of allyl chloride and 0.4 mL of trifluoroacetic acid were added to the reaction mixture and stirred for about 5 minutes. 8 g (30.7 mmol) of Intermediate 4-2 and 4.6 g (40 mmol) of 2-chloropyrimidine were subsequently added to the solution and stirred at about 50° C. for about 5 hours. After completion of the reaction, a saturated ammonium chloride solution was added to the resulting reaction mixture, followed by extraction with dichloromethane to obtain an organic phase. The organic phase was then washed with distilled water and an aqueous sodium chloride solution, dried with magnesium sulfate, and distilled under reduced pressure. The product was separated and purified by column chromatography, thereby obtaining about 6.2 g (23.9 mmol, Yield: 78%) of Intermediate 28-1. This compound was identified by LC-MS.

LC-MS m/z=260.11 (M+H)$^+$

2) Synthesis of Compound 28

Compound 28 (Yield: 12%) was synthesized in the same manner as Compound 4 in Synthesis Example 4, except that Intermediate 28-1, instead of Intermediate 4-1, was used. This compound was identified by LC-MS.

LC-MS m/z=968.27 (M+H)$^+$

Synthesis Example 20

Synthesis of Compound 29

Compound 29 was synthesized according to Reaction Scheme 29.

Reaction Scheme 29

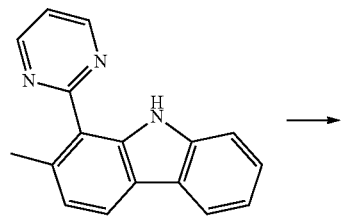

-continued

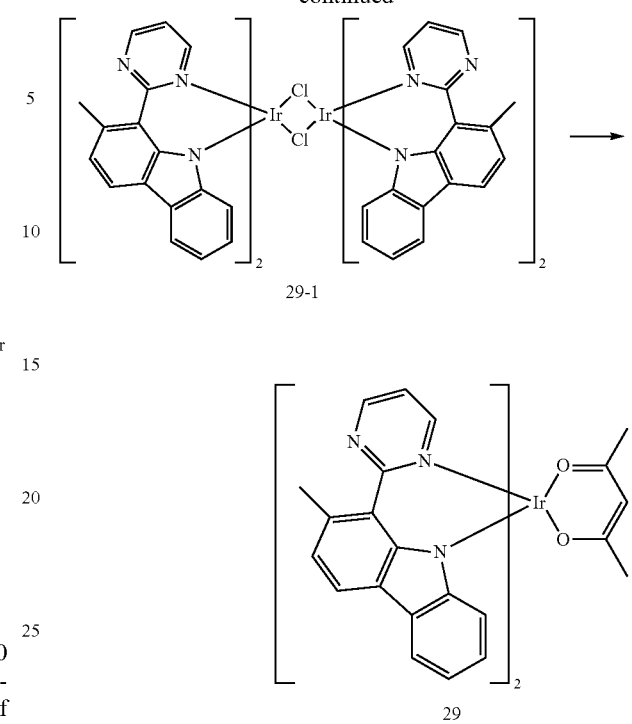

29-1

29

1) Synthesis of Intermediate 29-1

Intermediate 29-1 (Yield: 70%) was synthesized in the same manner as Intermediate 5-1 in Synthesis Example 5, except that Intermediate 28-1 instead of Intermediate 4-1, was used. This compound was subjected to further reaction without structural identification.

2) Synthesis of Compound 29

Compound 29 (Yield: 15%) was synthesized in the same manner as Compound 2 in Synthesis Example 2, except that Intermediate 28-1, instead of Intermediate 2-1, was used. This compound was identified by LC-MS.

LC-MS m/z=809.21 (M+H)$^+$

Synthesis Example 21

Synthesis of Compound 30

Compound 30 was synthesized according to Reaction Scheme 30.

Reaction Scheme 30

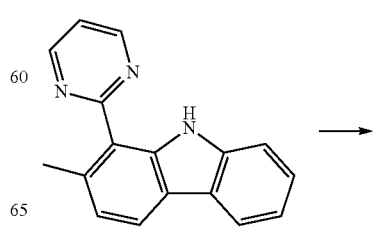

-continued

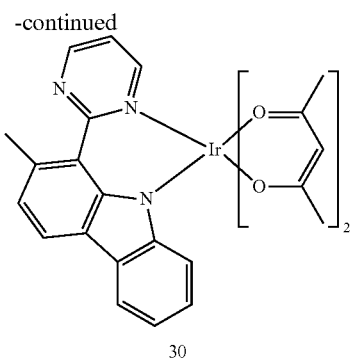

30

Synthesis of Compound 30

Compound 30 (Yield: 34%) was synthesized in the same manner as Compound 6 in Synthesis Example 62, except that Intermediate 28-1, instead of Intermediate 4-1, was used. This compound was identified by LC-MS.

LC-MS m/z=650.16 (M+H)$^+$

Example 1

An ITO glass substrate was cut to a size of about 50 millimeters (mm)×50 mm×0.5 mm, and sonicated in acetone, isopropyl alcohol, and deionized water, for about 5 minutes in each solvent, cleaned by irradiation of ultraviolet rays and exposure to ozone for about 30 minutes.

After m-MTDATA was deposited on the ITO electrode (anode) of the ITO glass substrate at a deposition rate of about 1 Angstroms per second (Å/sec) to form a hole injection layer (HIL) having a thickness of about 600 Angstroms (Å), NPB was deposited on the HIL at a deposition rate of about 1 Å/sec to form a hole transport layer (HIL) having a thickness of about 250 Å.

Next, Compound 4 (dopant) and CBP (host) were co-deposited on the HTL at a deposition rate of about 0.1 Å/sec and about 1 Å/sec, respectively, to form an emission layer (EML) having a thickness of about 400 Å.

After BAlq was deposited on the EML at a deposition rate of about 1 Å/sec to form a hole blocking layer (HBL) having a thickness of about 50 Å, Alq$_3$ was deposited on the HBL to form an electron transport layer (ETL) having a thickness of about 300 Å, LiF was deposited on the ETL to form an electron injection layer (EIL) having a thickness of about electron injection layer, and Al was vacuum-deposited on the EIL to form a second electrode (cathode) having a thickness of about 1,200 Å, thereby manufacturing an organic light-emitting device having a structure of ITO/m-MTDATA (600 Å)/NPB (250 Å) CBP+10% (Compound 4) (400 Å)/Balq(50 Å)/Alq3(300 Å)/LiF(10 Å)/Al(1,200 Å).

Examples 2 to 4

Organic light-emitting devices were manufactured in the same manner as in Example 1, except that Compounds 5, 11, and 12, instead of Compound 4, as shown in Table 2 were used, respectively, as a dopant in forming the EML, Evaluation Example 1

Characteristic Evaluation of Organic Light-emitting Device

Driving voltages, current efficiencies, power efficiencies, electroluminescent (EL) wavelengths, and external quantum efficiencies of the organic light-emitting devices of Examples 1 to 4 were evaluated using a current-voltage electrometer (Keithley 2400) and a spectrometer (Minolta Cs-1000A). The results are shown in Table 2.

TABLE 2

| Example | Dopant | Driving voltage (V) | Current efficiency (cd/A) | Power efficiency (lm/W) | $\lambda_{max}$ (nm) | External quantum efficiency (%) |
|---|---|---|---|---|---|---|
| Example 1 | Compound 4 | 6.4 | 14 | 6.9 | 623 | 17 |
| Example 2 | Compound 5 | 6.2 | 12 | 6.1 | 624 | 17 |
| Example 3 | Compound 11 | 6.5 | 13 | 6.3 | 618 | 17 |
| Example 4 | Compound 12 | 6.3 | 10 | 5.0 | 580 | 16 |

Referring to Table 2, the organic light-emitting devices of Examples 1 to 4 were found to have similar driving voltage, current efficiency, power efficiency, and quantum efficiency characteristics, compared to those of typical organic light-emitting devices.

As described above, according to the one or more embodiments, an organometallic compound represented by Formula 1 may have improved electric characteristics and good thermal stability. Therefore, an organic light-emitting device using the organometallic compound may have improved driving voltage, current density, efficiency, power, color purity, and lifetime characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. An organometallic compound represented by Formula 1:

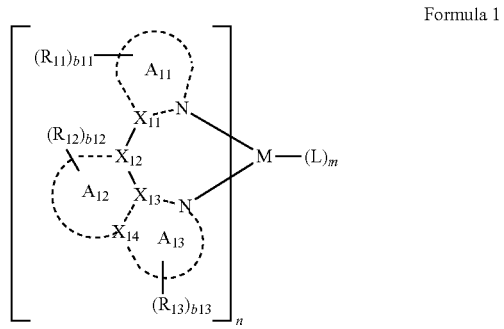

Formula 1 wherein, in Formula 1,

M is selected from Ir, Eu, Tb, and Tm;

$X_{11}$ and $X_{14}$ are each independently selected from C and N;

$X_{12}$ and $X_{13}$ are C;

$A_{11}$ is selected from $C_1$-$C_{20}$ heterocyclic groups;

$A_{12}$ is selected from a $C_5$-$C_{20}$ cyclic group and a $C_1$-$C_{20}$ heterocyclic group;

$A_{13}$ is selected from a pyrrole and an indole;

$R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), and —N($Q_1$)($Q_2$), wherein $R_{11}$ and $R_{12}$ are optionally linked to each other to form a saturated or unsaturated ring; and $Q_1$ to $Q_3$ are each independently selected from a hydrogen, a deuterium, a substituted or unsubstituted $C_1$-$C_{20}$ alkyl group, a substituted or unsubstituted $C_6$-$C_{20}$ aryl group, a substituted or unsubstituted monovalent non-aromatic condensed polycyclic group, and a substituted or unsubstituted monovalent non-aromatic condensed heteropolycyclic group;

n is selected from 1 and 2;

L is is a ligand represented by one of Formulae 2-1 to 2-6:

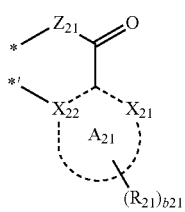

2-1

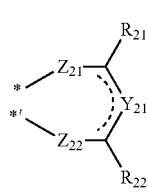

2-2

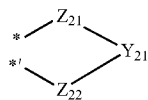

2-3

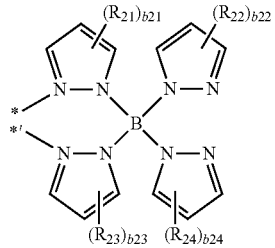

2-4

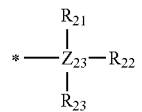

2-5

2-6 wherein, in Formulae 2-1 to 2-6, $A_{21}$ is selected from a $C_5$-$C_{20}$ cyclic group and a $C_1$-$C_{20}$ heterocyclic group;

$X_{21}$ and $X_{22}$ are each independently selected from C and N;

$Y_{21}$ is selected from a single bond, a double bond, a substituted or unsubstituted $C_1$-$C_5$ alkylene group, a substituted or unsubstituted $C_2$-$C_5$ alkenylene group, and a substituted or unsubstituted $C_6$-$C_{10}$ arylene group;

$Z_{21}$ and $Z_{22}$ are each independently selected from N, O, N($R_{25}$), P($R_{25}$)($R_{26}$), and As($R_{25}$)($R_{26}$), $Z_{23}$ is selected from P and As;

$R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b21 to b24 are each independently selected from 1, 2, and 3; and

* and *' are each independently a binding site with an adjacent atom; and m is selected from 1, 2, 3, and 4.

2. The organometallic compound of claim 1, wherein the organometallic compound of Formula 1 is represented by one of Formulae 1-11 to 1-22:

1-11
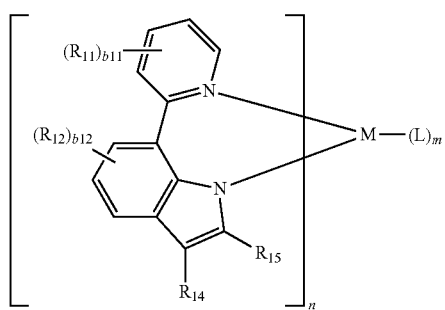
1-12
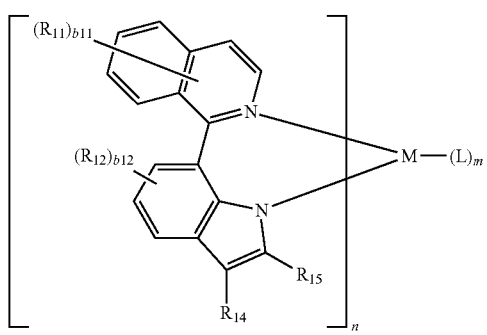
1-13
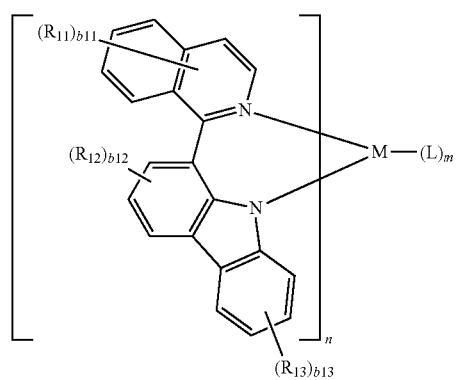
1-14
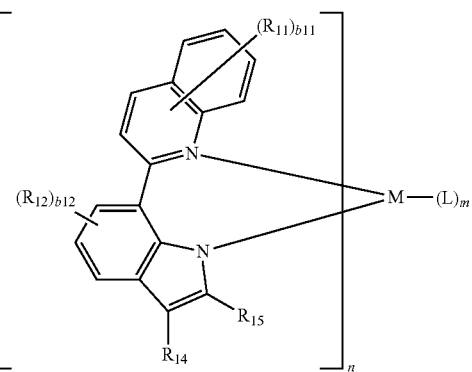
1-15
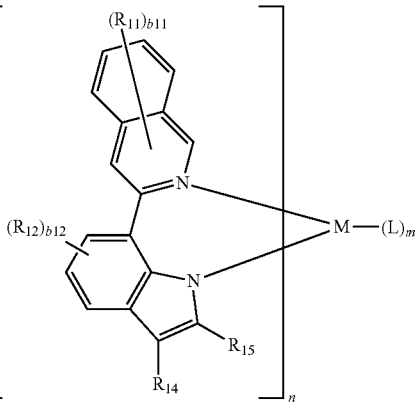
1-16
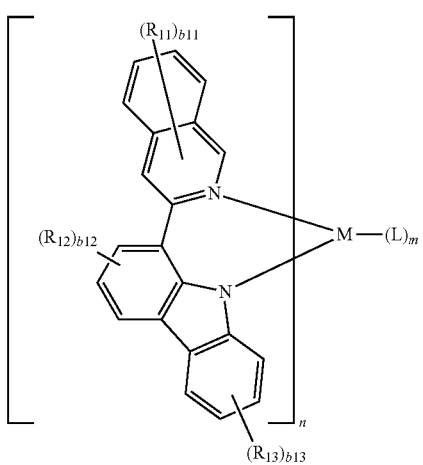
1-17

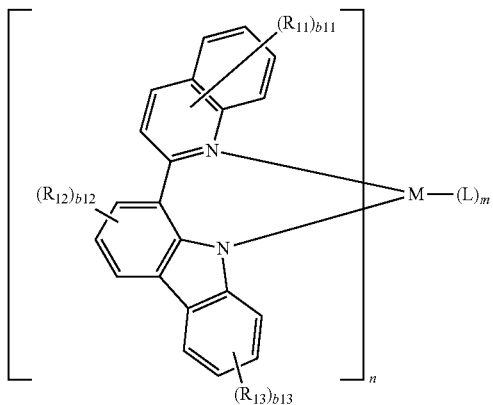
1-18
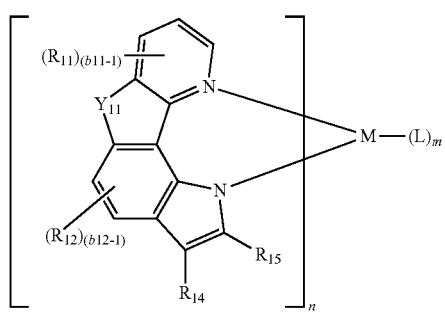
1-19
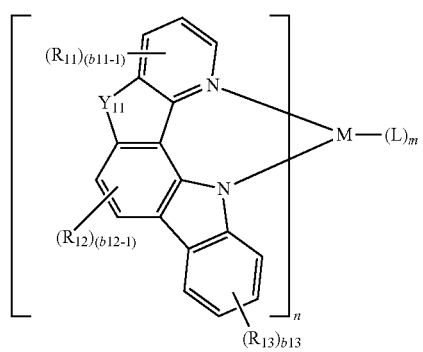
1-20
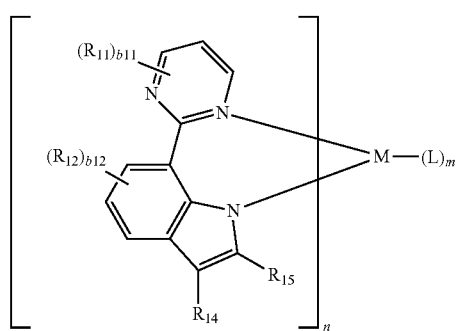
1-21
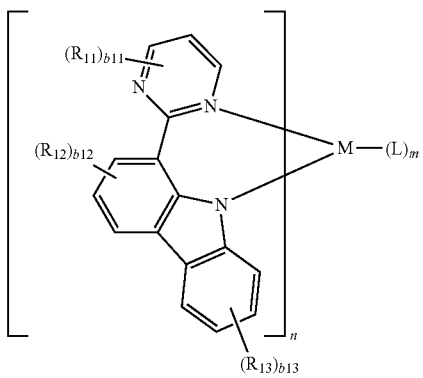
1-22
wherein, in Formulae 1-11 to 1-22,
M, $R_{11}$ to $R_{13}$, b11 to b13, n, L, and m are defined the same as those in Formula 1;
$R_{14}$ and $R_{15}$ are each independently defined the same as $R_{11}$ in Formula 1; and
$Y_{11}$ is selected from O, S, and groups represented by Formulae 9-1 to 9-15:
9-1
9-2
9-3
9-4
9-5
9-6
9-7
9-8
9-9

-continued

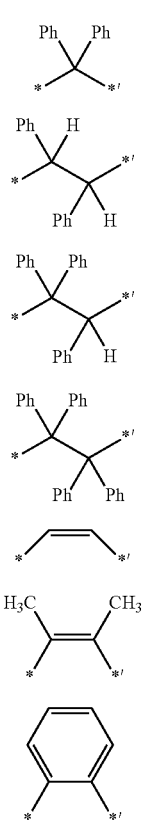

wherein, in Formulae 9-1 to 9-15,
Ph is a phenyl group; and
* and *' are each independently a binding site with an adjacent atom.

3. An organometallic compound represented by Formula 1:

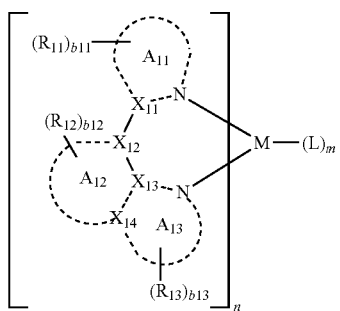

Formula 1 wherein, in Formula 1,
M is selected from Ir, Eu, Tb, and Tm;
$X_{11}$ and $X_{14}$ are each independently selected from C and N;
$X_{12}$ and $X_{13}$ are C;
$A_{11}$ is selected from $C_1$-$C_{20}$ heterocyclic groups;
$A_{12}$ is selected from a $C_5$-$C_{20}$ cyclic group and a $C_1$-$C_{20}$ heterocyclic group;
$A_{13}$ is selected from an imidazole, a thiazine, an oxazine, a benzimidazole, a benzothiazine, and a benzoxazine;
$R_{11}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)(Q$_1$), —Si(Q$_1$)(Q$_2$)(Q$_3$), and —N(Q$_1$)(Q$_2$), wherein $R_{11}$ and $R_{12}$ are optionally linked to each other to form a saturated or unsaturated ring; and $Q_1$ to $Q_3$ are each independently selected from a hydrogen, a deuterium, a substituted or unsubstituted $C_1$-$C_{20}$ alkyl group, a substituted or unsubstituted $C_6$-$C_{20}$ aryl group, a substituted or unsubstituted monovalent non-aromatic condensed polycyclic group, and a substituted or unsubstituted monovalent non-aromatic condensed heteropolycyclic group;
n is selected from 1, 2, and 3;
L is selected from a monodentate ligand and a bidentate ligand; and
m is selected from 0, 1, 2, 3, and 4.

4. The organometallic compound of claim 3, wherein M is Ir.

5. The organometallic compound of claim 3, wherein $X_{11}$ to $X_{14}$ are C.

6. The organometallic compound of claim 3, wherein $A_{11}$ is selected from a pyrrole, an imidazole, a pyrazole, a thiazole, an isothiazole, an oxazole, an isoxazole, a triazole, a pyridine, thiazine, oxazine, a pyrazine, a pyrimidine, a quinoline, an isoquinoline, a benzoquinoline, a quinoxaline, a quinazoline, a naphthyridine, an indole, a benzimidazole, a benzothiazole, benzisothiazole, a benzoxazole, a benzisoxazole, a benzothiazine, a benzoxazine, and a triazine.

7. The organometallic compound of claim 3, wherein $A_{11}$ is selected from a pyridine, a pyrazine, a pyrimidine, a quinoline, and an isoquinoline.

8. The organometallic compound of claim 3, wherein $A_{12}$ is selected from a benzene, a naphthalene, a pyridine, a pyrimidine, a pyrazine, a quinoline, and an isoquinoline.

9. The organometallic compound of claim 3, wherein $A_{12}$ is selected from a benzene and a naphthalene.

10. The organometallic compound of claim 3, wherein $R_{11}$ to $R_{13}$ are each independently selected from
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group,
a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, and a C$_1$-C$_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and —C(=O)(Q$_1$), —Si(Q$_1$)(Q$_2$)(Q$_3$), and —N(Q$_1$)(Q$_2$), wherein Q$_1$ to Q$_3$ are each independently selected from substituted or unsubstituted C$_1$-C$_{20}$ alkyl groups.

11. The organometallic compound of claim 3, wherein R$_{11}$ to R$_{13}$ are each independently selected from a hydrogen, a deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, and a tert-butoxy group, a C$_1$-C$_{20}$ alkyl group and a C$_1$-C$_{20}$ alkoxy group, each substituted with at least one of a deuterium, —F, —Cl, —Br, —I, a cyano group, a phenyl group, and a naphthyl group, a phenyl group and a naphthyl group, and a phenyl group and a naphthyl group, each substituted with at least one of a deuterium, —F, —Cl, —Br, —I, —CD$_3$, —CD$_2$H, —CDH$_2$, —CF$_3$, —CF$_2$H, —CFH$_2$, a cyano group, a methyl group, an ethyl group, an n-propyl group, an iso-propyl group, an n-butyl group, an iso-butyl group, a sec-butyl group, a tert-butyl group, a methoxy group, an ethoxy group, a n-propoxy group, an iso-propoxy group, a n-butoxy group, a tert-butoxy group, a phenyl group, and a naphthyl group.

12. The organometallic compound of claim 3, wherein R$_{11}$ and R$_{12}$ are linked to each other to form a group represented by Y$_{11}$, and Y$_{11}$ is selected from O, S, and groups represented by Formulae 8-1 to 8-5:

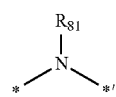

8-1

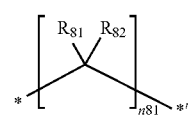

8-2

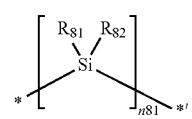

8-3

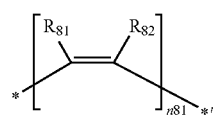

8-4

-continued

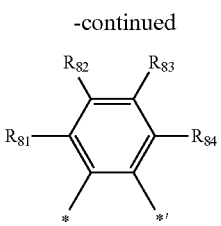

8-5 wherein, in Formulae 8-1 to 8-5, $R_{81}$ to $R_{84}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group;

n81 is selected from 1, 2, 3, 4, and 5; and

* and *' are each independently a binding site with an adjacent atom.

13. The organometallic compound of claim 3, wherein $R_{11}$ and $R_{12}$ are linked to each other to form a group represented by $Y_{11}$, and $Y_{11}$ is selected from O, S, and groups represented by Formulae 9-1 to 9-15:

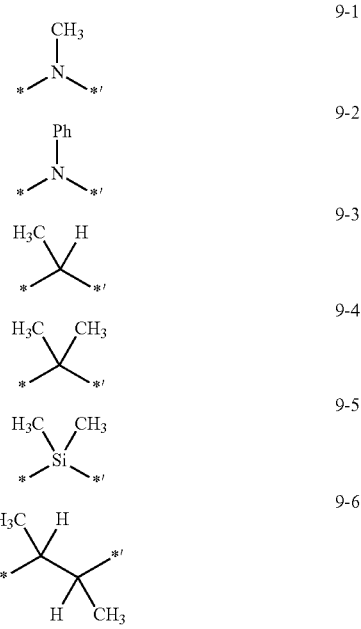

101
-continued

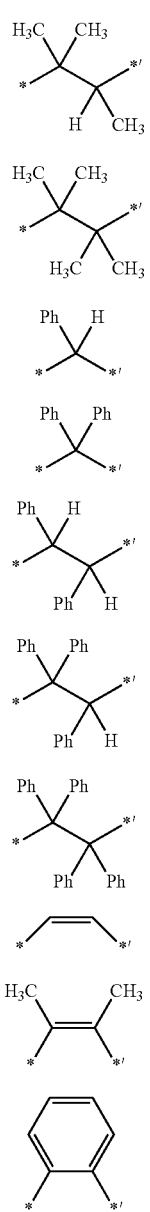

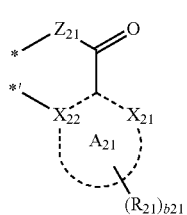

wherein, in Formulae 9-1 to 9-15,
Ph is a phenyl group; and
* and *' are each independently a binding site with an adjacent atom.

14. The organometallic compound of claim 3, wherein L is a ligand represented by one of Formulae 2-1 to 2-6:

102
-continued

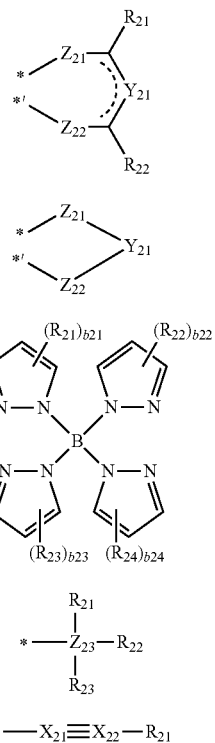

wherein, in Formulae 2-1 to 2-6,
$A_{21}$ is selected from a $C_5$-$C_{20}$ cyclic group and a $C_1$-$C_{20}$ heterocyclic group;
$X_{21}$ and $X_{22}$ are each independently selected from C and N;
$Y_{21}$ is selected from a single bond, a double bond, a substituted or unsubstituted $C_1$-$C_5$ alkylene group, a substituted or unsubstituted $C_2$-$C_5$ alkenylene group, and a substituted or unsubstituted $C_6$-$C_{10}$ arylene group;
$Z_{21}$ and $Z_{22}$ are each independently selected from N, O, $N(R_{25})$, $P(R_{25})(R_{26})$, and $As(R_{25})(R_{26})$;
$Z_{23}$ is selected from P and As;
$R_{21}$ to $R_{26}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

b21 to b24 are each independently selected from 1, 2, and 3; and

* and *' are each independently a binding site with an adjacent atom.

15. The organometallic compound of claim 3, wherein L is a ligand represented by one of Formulae 3-1 to 3-4:

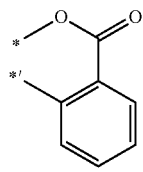

3-1

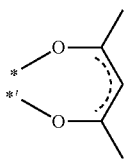

3-2

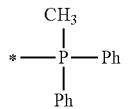

3-3

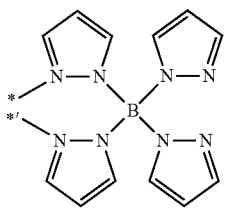

3-4 wherein, in Formulae 3-1 to 3-4,

Ph is a phenyl group; and

* and *' are each independently a binding site with an adjacent atom.

16. The organometallic compound of claim 3, wherein the organometallic compound of Formula 1 is represented by one of Formulae 1-1 and 1-2:

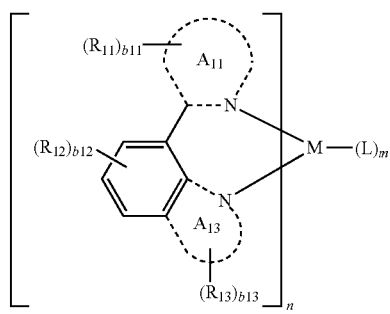

1-1

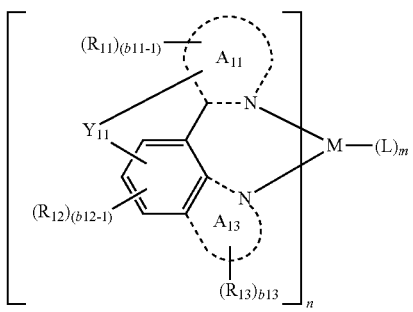

1-2 wherein, in Formulae 1-1 and 1-2,

M, $A_{11}$, $A_{13}$, $R_{11}$ to $R_{13}$, b11 to b13, n, L, and m are the same as in Formula 1; and $Y_{11}$ is selected from O, S, and groups represented by O, S and Formulae 8-1 to 8-5:

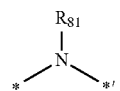

8-1

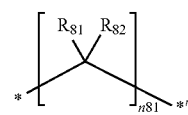

8-2

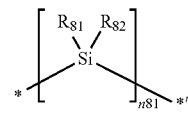

8-3

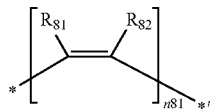

8-4

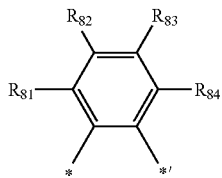

8-5 wherein, in Formulae 8-1 to 8-5, $R_{81}$ to $R_{84}$ are each independently selected from a hydrogen, a deuterium, —F, —Cl, —Br, —I, a hydroxyl group, a cyano group, a nitro group, an amino group, an amidino group, a hydrazine group, a hydrazone group, a a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a napthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, and an imidazopyridinyl group, each substituted with at least one of a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group and an imidazopyridinyl group;

n81 is selected from 1, 2, 3, 4, and 5; and

* and *' are each independently a binding site with an adjacent atom.

17. An organometallic compound selected from Compounds 2 to 30:

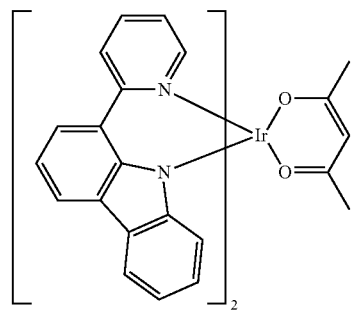

2

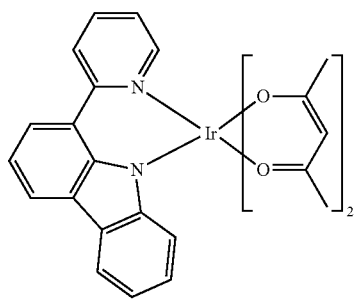

3

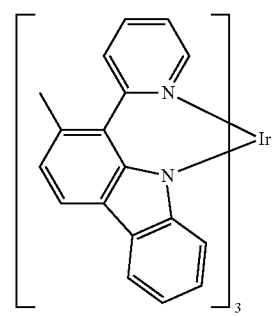

4

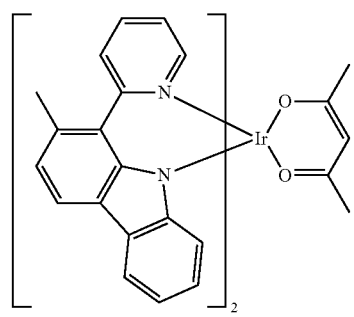

5

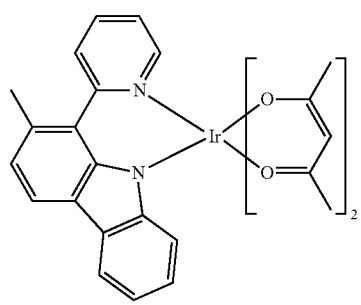
6
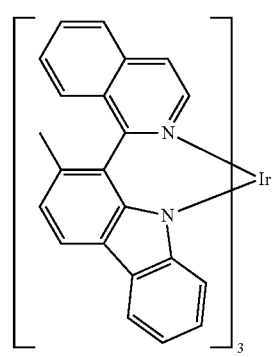
7
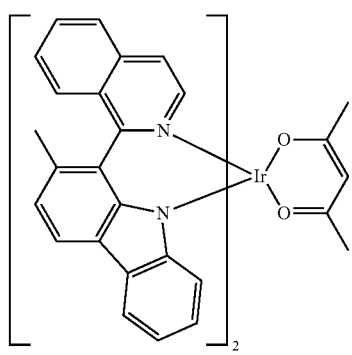
8
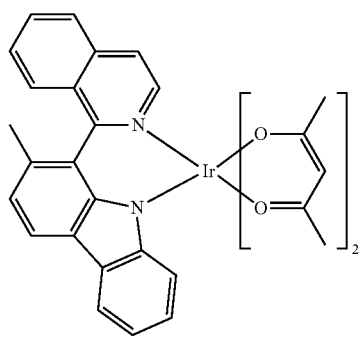
9
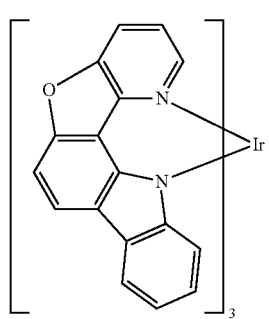
10
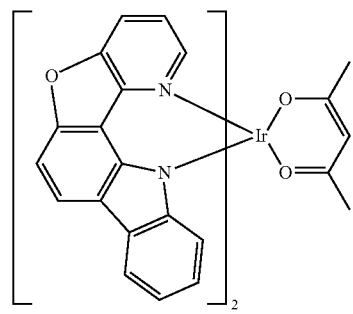
11
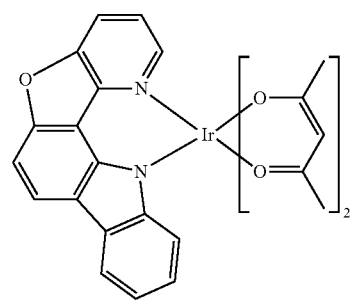
12
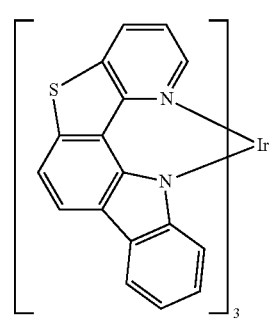
13
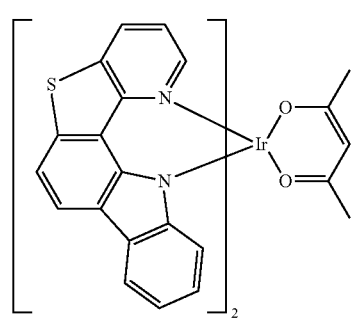
14
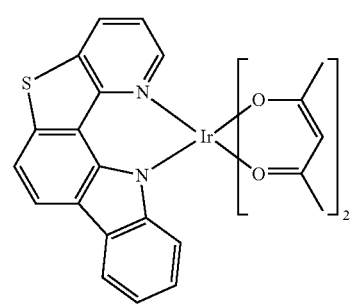
15

-continued
16
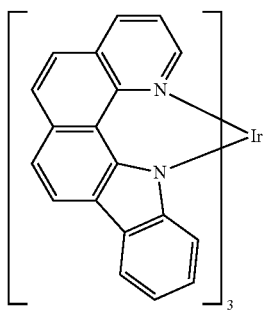
17
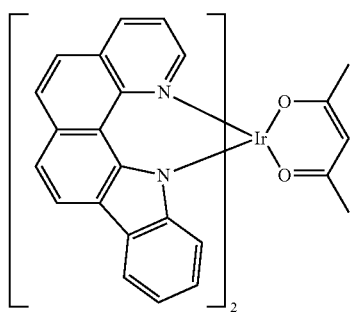
18
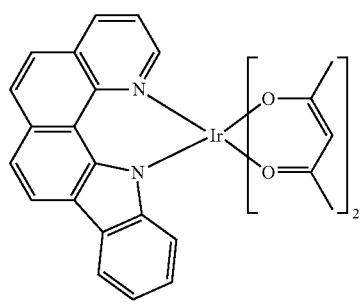
19
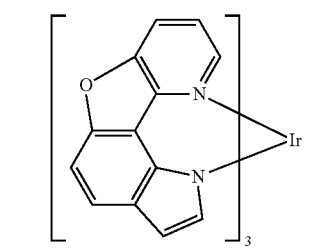
20
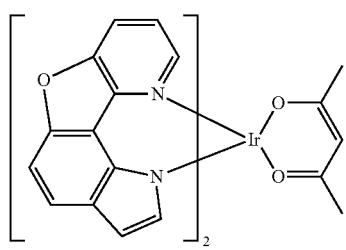
-continued
21
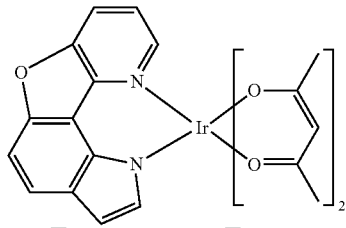
22
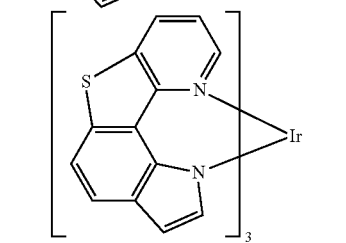
23
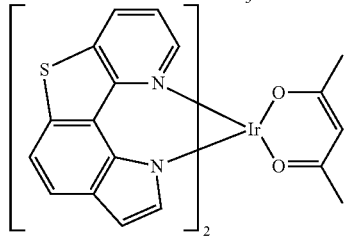
24
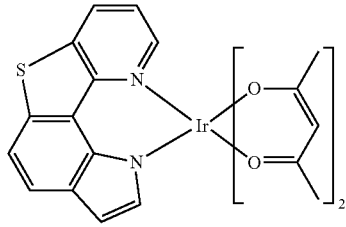
25
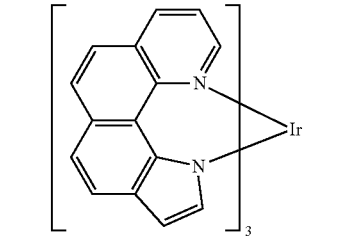
26
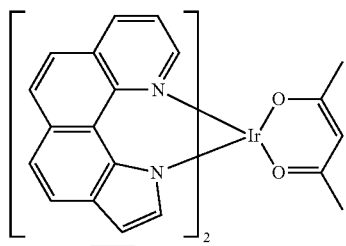
27
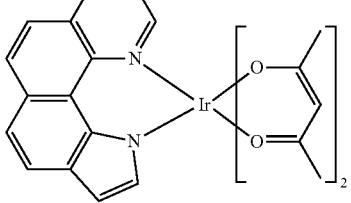

111
-continued

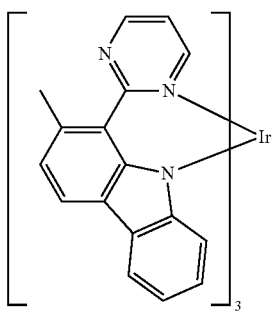

28

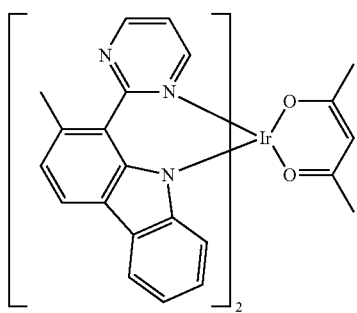

29

112
-continued

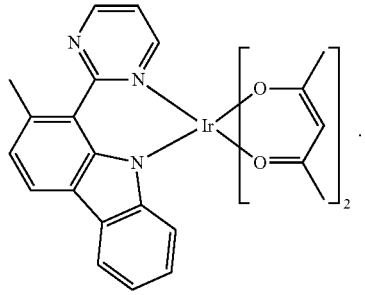

30

18. An organic light-emitting device comprising:
a first electrode;
a second electrode; and
an organic layer disposed between the first electrode and the second electrode,
wherein the organic layer comprises an emission layer and at least one organometallic compound of claim 3.

19. The organic light-emitting device of claim 18, wherein the emission layer comprises the at least one organometallic compound.

* * * * *